United States Patent
Chiu et al.

(10) Patent No.: US 11,221,336 B2
(45) Date of Patent: Jan. 11, 2022

(54) ENCODED CHROMOPHORIC POLYMER PARTICLES AND METHODS OF USE THEREOF

(71) Applicant: UNIVERSITY OF WASHINGTON THROUGH ITS CENTER FOR COMMERCIALIZATION, Seattle, WA (US)

(72) Inventors: Daniel T. Chiu, Seattle, WA (US); Changfeng Wu, Seattle, WA (US); Jiangbo Yu, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 93 days.

(21) Appl. No.: 16/556,006

(22) Filed: Aug. 29, 2019

(65) Prior Publication Data
US 2020/0011874 A1    Jan. 9, 2020

Related U.S. Application Data

(63) Continuation of application No. 15/100,056, filed as application No. PCT/US2014/067471 on Nov. 25, 2014, now Pat. No. 10,444,243.
(Continued)

(51) Int. Cl.
*G01N 33/58* (2006.01)
*C09K 11/06* (2006.01)
(Continued)

(52) U.S. Cl.
CPC .............. *G01N 33/58* (2013.01); *C09K 11/02* (2013.01); *C09K 11/06* (2013.01);
(Continued)

(58) Field of Classification Search
None
See application file for complete search history.

(56) References Cited

U.S. PATENT DOCUMENTS

| | | |
|---|---|---|
| 2006/0127369 A1 | 6/2006 | Christensen et al. |
| 2013/0234067 A1 | 9/2013 | Chiu et al. |

(Continued)

FOREIGN PATENT DOCUMENTS

| | | |
|---|---|---|
| CN | 103261087 A | 8/2013 |
| JP | 2011-506673 A | 3/2011 |

(Continued)

OTHER PUBLICATIONS

Notice of Reasons for Rejection (JP) dated Jul. 21, 2020, issued in corresponding Japanese Application No. 2016-534201, 21 pages.
(Continued)

*Primary Examiner* — Xiaoyun R Xu
(74) *Attorney, Agent, or Firm* — Christensen O'Connor Johnson Kindness PLLC

(57) ABSTRACT

The present disclosure provides encoded chromophoric polymer particles that are capable of, for example, optical and/or biomolecular encoding of analytes. The present disclosure also provides suspensions comprising a plurality of encoded chromophoric polymer particles. The present disclosure also provides methods of using the encoded chromophoric polymer particles and systems for performing multiplex analysis with encoded chromophoric polymer particles.

19 Claims, 23 Drawing Sheets

Related U.S. Application Data

(60) Provisional application No. 61/909,698, filed on Nov. 27, 2013.

(51) Int. Cl.
    *G01N 21/64*         (2006.01)
    *C09K 11/02*        (2006.01)

(52) U.S. Cl.
    CPC ..... *G01N 21/6408* (2013.01); *G01N 21/6428* (2013.01); *G01N 33/582* (2013.01); *G01N 33/587* (2013.01); *G01N 33/588* (2013.01); *C09K 2211/1007* (2013.01); *C09K 2211/1011* (2013.01); *C09K 2211/1044* (2013.01); *C09K 2211/1416* (2013.01); *C09K 2211/182* (2013.01); *G01N 2021/6417* (2013.01); *G01N 2021/6439* (2013.01); *G01N 2021/6441* (2013.01); *G01N 2201/12* (2013.01)

(56) References Cited

U.S. PATENT DOCUMENTS

| | | |
|---|---|---|
| 2013/0266957 A1 | 10/2013 | Chiu et al. |
| 2018/0156810 A1 | 6/2018 | Mao et al. |

FOREIGN PATENT DOCUMENTS

| | | |
|---|---|---|
| JP | 2017507191 A | 3/2017 |
| WO | 2004028682 A2 | 4/2004 |
| WO | 2009107859 A2 | 9/2009 |
| WO | 2011057295 A2 | 5/2011 |
| WO | 2012054525 A2 | 4/2012 |
| WO | 2013101902 A2 | 7/2013 |
| WO | 2013116614 A1 | 8/2013 |
| WO | 2014058903 A2 | 4/2014 |

OTHER PUBLICATIONS

Notice on Reexamination (CN) dated Mar. 25, 2020, issued in corresponding Chinese Application No. 201480074042.8, 35 pages.

European Examination Report dated Mar. 16, 2020, issued in corresponding European Application No. 19165950.7 filed Nov. 25, 2014, 4 pages.

Notice of Refusal dated Jun. 7, 2019, issued in corresponding Japanese Patent Application No. 2016-534201, filed Nov. 25, 2014, 2 pages.

Search Report by Registered Search Organization, dated Sep. 11, 2018, issued in corresponding Japanese Patent Application No. 2016-534201, filed Nov. 25, 2014, 18 pages.

Jin, et al. Near-infrared fluorescent dye-doped semiconducting polymer dots. ACS Nano. Feb. 22, 2011;5(2):1468-75. doi:10.1021/nn103304m. Epub Jan. 31, 2011.

Office action dated Oct. 4, 2018 for JP Application No. 2016-534201.

Wu, et al. Energy Transfer in a Nanoscale Multichromophoric System: Fluorescent Dye-Doped Conjugated Polymer Nanoparticles. Phys Chem C Nanomater Interfaces. Feb. 14, 2008; 112(6): 1772-1781.

CN 201480074042.8 Second Office Action dated Mar. 13, 2018 (w/ English translation).

EP14865362 Examination Report dated Jun. 6, 2018.

Extended European search report and opinion dated Aug. 25, 2017 for EP Application No. 14865362.9.

Wang, et al., A Fluorophore-Doped Polymer Nanomaterial for Referenced Imaging of pH and Temperature with Sub-Micrometer Resolution, Adv. Funct. Mater, 2012, 22, 4202-7.

Office action dated Jul. 7, 2017 for CN Application No. 201480074042.8.

Abdelrahman, et al. Lanthanide-containing polymer microspheres by multiplestage dispersion polymerization for highly multiplexed bioassays. J Am Chem Soc. Oct. 28, 2009; 131(42):15276-83. doi: 10.1021/ja9052009.

Chen, et al. Preparation of fluorescence tunable polymer nanoparticles by one-step mini-emulsion. Journal of Macromolecular Science, Part A: Pure and Applied Chemistry. 2010; 47(11):1135-1141.

International search report and written opinion dated Jan. 29, 2015 for PCT/US2014/067471.

Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.

Rong, Y. et al., "Multicolor Fluorescent Semiconducting Polymer Dots with Narrow Emissions and High Brightness," ACS Nano, 7(1):376-384, 2013 (published online Jan. 2, 2013).

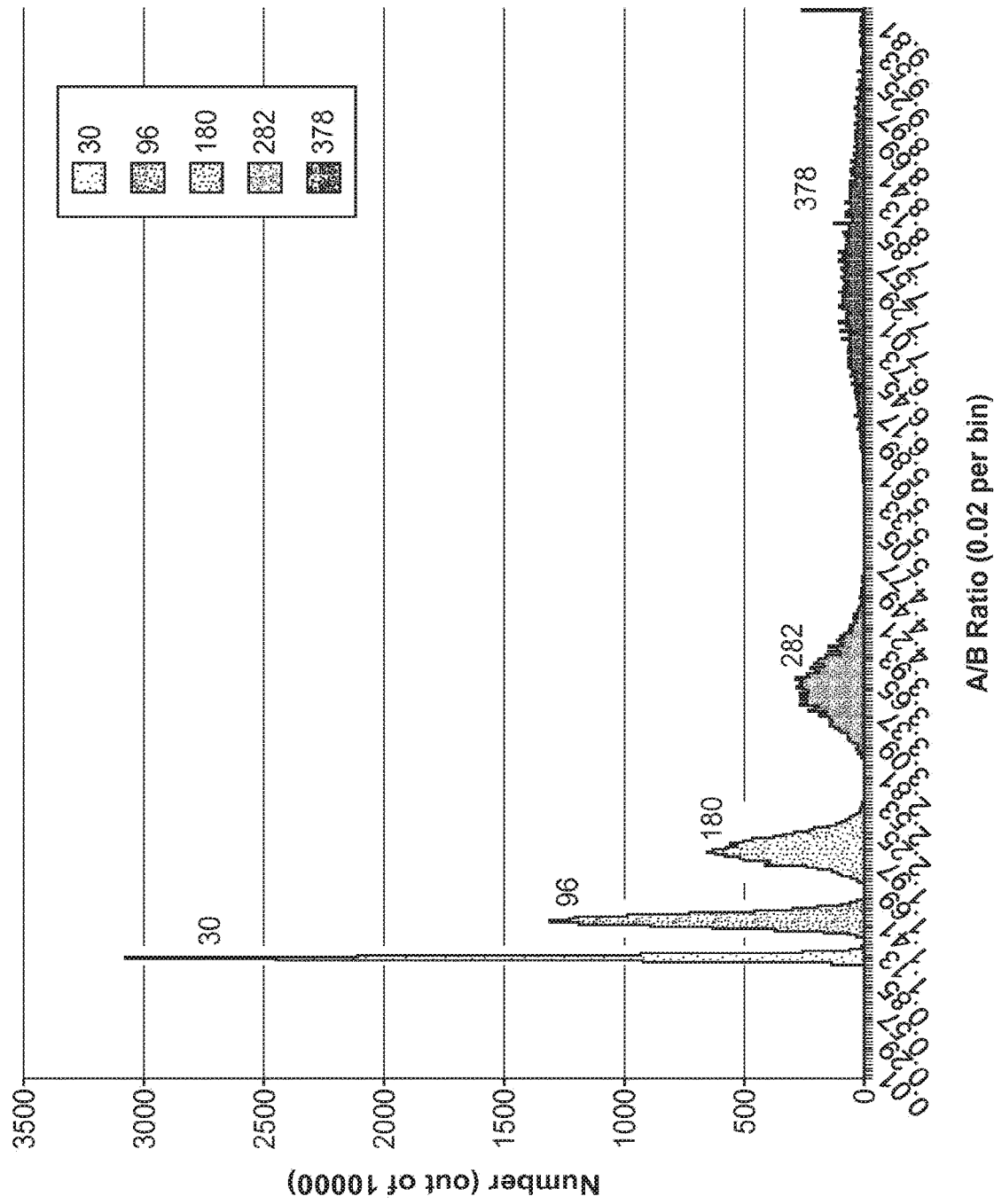

ENCODED CHROMOPHORIC POLYMER PARTICLES AND METHODS OF USE THEREOF

CROSS-REFERENCE(S) TO RELATED APPLICATION(S)

This application is a Continuation Application of U.S. application Ser. No. 15/100,056, filed May 27, 2016, which is a US National Phase Application under 35 U.S.C. § 371 of International Application no. PCT/US2014/067471, filed Nov. 25, 2014, which claims the benefit of U.S. Provisional Application No. 61/909,698, filed Nov. 27, 2013, which are incorporated herein by reference in their entirety.

BACKGROUND

There have been recent technological advances in bio-analytical science and bioengineering which have influenced many research areas such as flow cytometry, gene profiling, and clinical diagnostics. Among those, the development of genomics and proteomics generate a great deal of sequence data, therefore there is a need to develop new technologies to rapidly screen a large number of nucleic acids and proteins. Optical encoding provides a promising way to enable high throughput analysis. In a wavelength-and-intensity multiplexing, the number of codes increases exponentially with increasing number of color and intensity levels. A 3-color/10-intensity scheme yields approximately 1000 codes, whereas a 6-color/10-intensity scheme has a theoretical coding capacity of about one million. However, a major problem with the encoding approach is that no reliable technologies are currently available for massively parallel coding on the nanometer scale.

There is a need to provide improved compositions, systems, and methods for optical encoding. The present disclosure addresses this need and more.

SUMMARY

The present disclosure provides encoded chromophoric polymer particles and methods of use thereof.

In various aspects, the present disclosure provides an encoded chromophoric polymer particle comprising: a polymer matrix comprising a chromophoric polymer; and a plurality of distinct chromophores, wherein each chromophore of the plurality of distinct chromophores comprises a predetermined set of tunable optical coding parameters, thereby defining an optically detectable code for the polymer particle.

In various aspects, the present disclosure provides a suspension comprising a first plurality of encoded chromophoric polymer particles and a liquid.

In various aspects, the present disclosure provides a method of detecting an analyte comprising: contacting a sample comprising an analyte with an encoded chromophoric polymer particle or a suspension of encoded chromophoric polymer particles; and detecting an optically detectable code emitted by an encoded chromophoric polymer particle in the sample, wherein the detection of the optically detectable code indicates at least one of the presence of the analyte in the sample, the identity of the analyte, or the concentration of the analyte in the sample.

In various aspects, the present disclosure provides a kit for detecting analytes in a sample, comprising a suspension of encoded chromophoric polymer particles.

In various aspects, the present disclosure provides a system for multiplex analysis comprising: a suspension of encoded chromophoric polymer particles; a sample comprising an analyte; a source of electromagnetic radiation; a detector; and a computer comprising a processor and a memory device with executable instructions stored thereon, the instructions when executed causing the processor to: operate the detector to measure an emission property; store the measured emission property; and analyze the measured emission property.

In various aspects, the present disclosure provides an optical encoding system comprising: a first encoded chromophoric polymer particle; and a second encoded chromophoric polymer particle, wherein the first and second encoded chromophoric polymer particles have optically detectable codes that are distinguishable from each other.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIGS. 7A and 7B depict population distributions of fluorophore A relative to fluorophore B in encoded chromophoric polymer particles made from varying amounts of monomer A and dimer AB. Five distributions are shown in FIG. 7A and two distributions are shown in FIG. 7B.

FIG. 16A shows time-decay curves of emitted fluorescence of chromophoric Eu-PSMA particles with increasing Nile blue concentration. FIG. 16B shows time-decay curves of emitted fluorescence of chromophoric Eu-PSMA/PVK particles with increasing Nile blue concentration.

DETAILED DESCRIPTION

Figure 1:
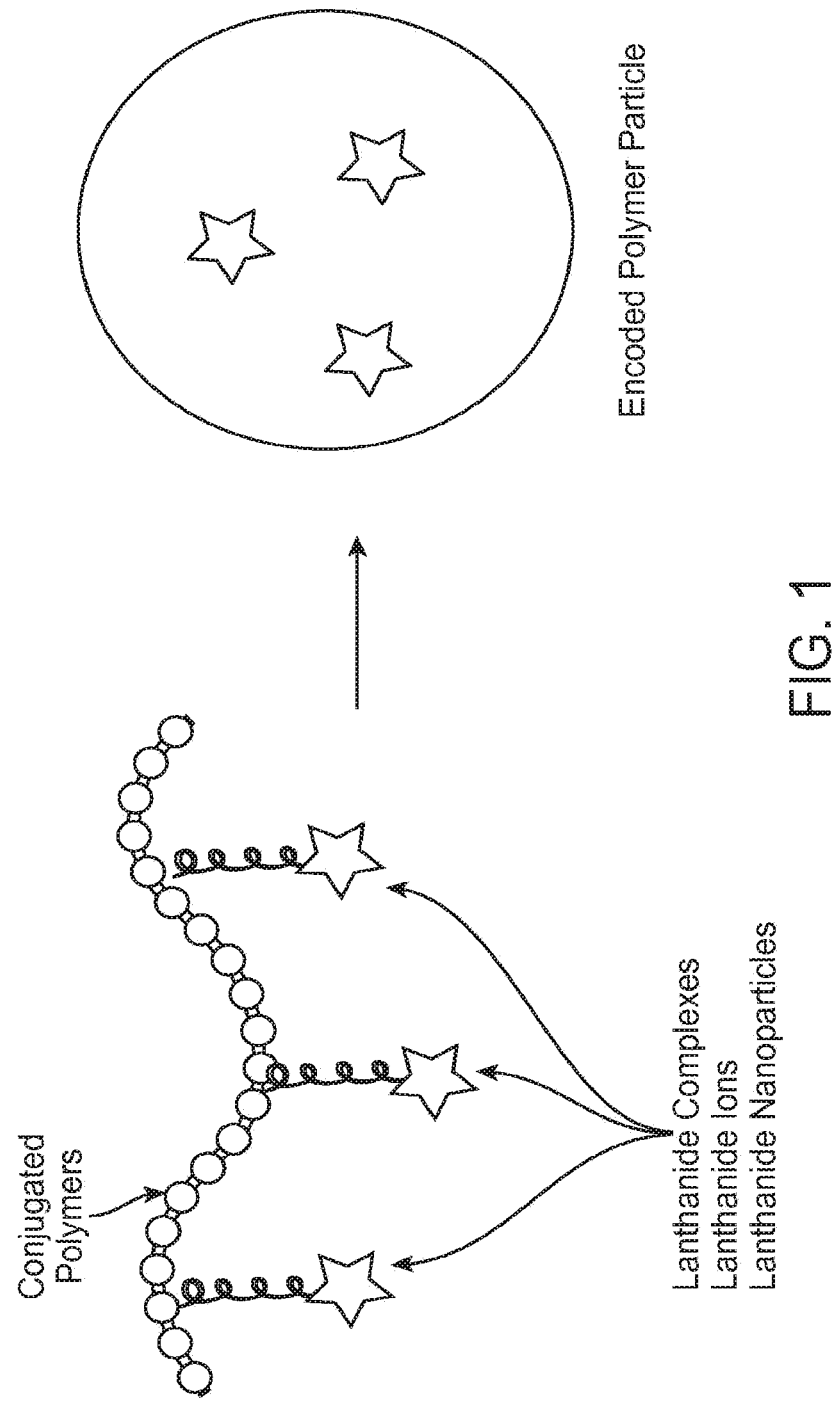
FIG. 1 depicts a schematic for designing encoded chromophoric polymer particles that include at least one type of conjugated polymer and at least one type of lanthanide species.

The present disclosure relates generally to compositions, systems, and methods for optical encoding. In some aspects, the present disclosure provides optically encoded chromophoric polymer particles having a plurality of distinct chromophores. Each distinct chromophore possesses with predetermined set of tunable optical coding parameters so as to define an optically detectable code for the polymer particle, e.g., based on emission wavelength, intensity, and/or lifetime. In certain aspects, a plurality of optical codes are produced by modulating the tunable optical coding parameters, e.g., by modifying the composition and/or structure of the chromophores. As the number of independently or semi-independently tunable optical parameters increases, the number of potential encoded chromophoric polymer particles increases exponentially, thereby creating the possibility of simultaneously identifying and quantifying a very large number of analytes.

For example, as described further herein, the present disclosure includes a variety of chromophoric polymer particles that exhibit multiple sets of emission peaks, wherein the intensity of these emission peaks are independently or semi-independently tunable in order to define distinguishable optical codes. These emission peaks can be tuned, e.g., by varying polymer structure and/or particle composition. Where the emission intensities are independently or semi-independently tunable, the particles can have unique or distinct emission spectra. A plurality of such particles with distinct emission spectra can be used to identify a plurality of analytes in complex samples. For instance, one subset of such encoded chromophoric polymer particles with one set of emission spectra can be configured to specifically associate with a particular set of analytes in a complex sample. By integrating molecular recognition and optical coding, each unique emission spectra, or code, can be considered a fingerprint that detects and analyzes a specific analyte in a complex mixture.

The encoded chromophoric polymer particles of the present disclosure provide a versatile platform capable of supporting a large number of distinguishable optical codes. Additionally, various encoded chromophoric polymer particles described herein exhibit improved characteristics, such as large extinction coefficients, high fluorescence quantum yield, fast emission rates, and excellent photostability. Furthermore, the encoded chromophoric polymers disclosed herein are capable of providing biomolecular encoding on the nanometer scale. While encoding in large micrometer size particles has been demonstrated, it is not optimal in certain situations. For example, fluorescent dye doped latex spheres, which are microns in diameter, are used for some bioanalytical applications. However, fluorescence quenching occurs when the dye doping concentration is above a few percent, therefore limiting the number of codes based on intensity levels. In some aspects, when the particle size is decreased to the nanometer range, this self-quenching places severe limits on encoding, because it limits the number of dyes that can be doped into a small nanoparticle. Inorganic quantum dots (Qdots) exhibit multicolor, narrow, and symmetric emission spectra that are desirable for encoding. However, in some aspects, it is difficult to integrate a sufficient number of Qdots into one nanometer sized particle to achieve independent color and intensity levels that can be distinguished at the single-particle level. The chromophoric polymer particles described herein enable integration of a wide variety of distinct chromophores, thereby allowing for a large number of distinct optical codes within a nanometer scale particle.

Various polymer compositions are suitable for use with the encoded chromophoric polymer particles described herein. In some aspects, a "polymer" is a molecule composed of at least two repeating structural units typically connected by covalent chemical bonds. The repeating structural unit may be one type of monomer, and the resulting polymer is a homopolymer. In some aspects, the polymers can include two different types of monomers, or three different types of monomers, or more types of monomers. One of ordinary skill in the art will appreciate that the different types of monomers can be distributed along a polymer chain in a variety of ways. For example, three different types of monomers can be randomly distributed along the polymer. It will similarly be appreciated that the distribution of monomers along the polymer can be represented in different ways. The number of repeating structural units (e.g., monomers) along the length of a polymer can be represented by "n." In some aspects, n can range, e.g., from at least 2, from at least 100, from at least 500, from at least 1000, from at least 5000, or from at least 10,000, or from at least 100,000, or higher. In certain aspects, n can range from 2 to 10000, from 20 to 10000, from 20 to 500, from 50 to 300, from 100 to 1000, or from 500 to 10,000.

In some aspects, polymers generally have extended molecular structures comprising backbones that optionally contain pendant side groups. The polymers provided herein can include, but are not limited to, linear polymers and branched polymers such as star polymers, comb polymers, brush polymers, ladders, and dendrimers. As described further herein, the polymers can include semiconducting polymers generally well known in the art.

In some aspects, a "polymer particle," "polymeric particle," or "Pdot" is a nanometer-sized entity, which represents a separate discontinuous phase surrounded by a continuous free-flowing medium. As used herein, the terms "polymer particle," "polymeric particle," or "Pdot" can be used interchangeably. The free flowing medium is usually a low-molecular-weight liquid, most often water.

In some aspects, the terms "polymer particle," "chromophoric polymer particle," "polymer dot," "chromophoric polymer dot," "fluorescent polymer dot," "chromophoric nanoparticle" and "Pdot" are used interchangeably to refer to structures comprising one or more polymers (e.g., semiconducting polymers, non-semiconducting polymers, or a combination thereof) that have been collapsed into a stable sub-micron-sized particle. Various methods are suitable for forming chromophoric polymer particles, as described further herein. The chromophoric polymer particles provided herein can be made up of a single polymer or can comprise blends of polymers. In certain aspects, the one or more polymers are collapsed, precipitated, and/or condensed to form a polymer matrix. In some aspects, the properties of the encoded chromophoric polymer particles are dependent on the polymer structures. Therefore, the polymer backbone (main chain), side chains, terminal units, and substituted groups can be varied to obtain specific properties. In some aspects, the optical properties of the chromophoric polymer particles can be tuned by varying the structures of the polymer backbone (main chain).

In certain aspects, the chromophoric polymer particles provided herein include one or more chromophores, also referred to herein as chromophoric units. In some aspects, the term "chromophore" or "chromophoric unit" is given its ordinary meaning in the art. A chromophore absorbs certain wavelengths of light, e.g., from the UV region to the near infrared region, and may be or may not be emissive. In some aspects, a chromophoric unit includes, but is not limited to, a unit of structures with delocalized pi-electrons, a unit of small organic dye molecules, and/or a unit of metal complexes. The chromophore can be part of the polymer matrix or be incorporated into the polymer matrix, e.g., by blending, crosslinking, and the like.

In certain aspects, the chromophoric polymer particles of the present disclosure include one or more chromophoric polymers. In some aspects, the term "chromophoric polymer" refers to a polymer in which at least a portion of the polymer absorbs certain wavelengths of light, e.g., ranging from UV to near infrared spectra. Chromophoric polymers according to the present disclosure may be or may not be emissive. In some aspects, a "chromophoric polymer" is a polymer in which at least a portion of the polymer includes chromophoric units. Examples of chromophoric polymers can include polymers comprising units of structures with delocalized pi-electrons such as semiconducting polymers, polymers comprising units of small organic dye molecules, polymers comprising units of metal complexes, and polymers comprising units of any combinations thereof. The chromophoric unit can be incorporated into the polymer backbone. The chromophoric unit can also be covalently attached to the side chain, or the terminal unit of the polymer. Chromophoric polymers can be made using standard synthesis methods generally well known in the art.

In certain aspects, the chromophoric polymer is a "conjugated polymer." The term "conjugated polymer" is recognized in the art. Electrons, holes, or electronic energy, can be conducted along the conjugated structure. In some aspects, a large portion of the polymer backbone can be conjugated. In some aspects, the entire polymer backbone can be conjugated. In some aspects, the polymer can include conjugated structures in their side chains or termini. In some aspects, the conjugated polymer can have conducting properties, e.g., the polymer can conduct electricity. In some aspects, the conjugated polymer can have semiconducting properties, e.g., the polymers can exhibit a direct band gap, leading to an efficient absorption or emission at the band edge.

In certain aspects, the encoded chromophoric polymer particles of the present disclosure include a single polymer or a plurality of polymers (e.g., forming a polymer matrix) that can be, e.g., chemically crosslinked and/or physically blended with various types of chromophores so as to modulate the optical properties of the encoded particle. Examples of chromophores suitable for use with the various aspects described herein include, but are not limited to, chromophoric polymers, lanthanide chromophores, chromophoric dyes (e.g., fluorescent and/or luminescent dyes), or combinations thereof. In some aspects, the chromophores provided herein exhibit narrow band emission properties (e.g., the full width at half maximum (FWHM) of the emission band is less than 70 nanometers). In some aspects, a "lanthanide chromophore" is a chromophore comprising an atom from the lanthanide group in the periodic table. More specifically, a lanthanide chromophore is a chromophore comprising an atom having an atomic number including or between 57 and 71.

In some aspects, the present disclosure provides encoded chromophoric polymer particles that are capable of optical multiplexing, e.g., wavelength-and-intensity multiplexing, wavelength-intensity-and-lifetime multiplexing, etc. In certain aspects, one or more chromophores having desirable optical properties are used to provide such multiplexing capabilities, such as chromophoric polymers, lanthanide chromophores, or chromophoric dyes. For example, the optical properties of chromophoric polymers include their superior characteristics such as large extinction coefficients, high fluorescence quantum yield, fast emission rates, and excellent photostability. In some aspects, this present disclosure utilizes the unique luminescent properties of lanthanide ions such as their narrow emission bandwidths, long lifetimes, and stable f-f transitions that are not substantially influenced by the environment. In addition, the polymer particles provide a flexible polymer matrix that can accommodate other fluorescent and/or luminescent materials. Therefore, different fluorescent and/or luminescent species (e.g., lanthanide complex molecules or lanthanide nanoparticles) can be integrated into the polymer matrix, while each species can maintain individual fluorescence and/or luminescence. Furthermore, various properties of each species, e.g., wavelength, intensity, lifetimes, etc., can be independently or semi-independently tuned. In some aspects, "independent" or "independently" have their usual meaning, and, "semi-independently" means that one property can be adjusted or manipulated without substantially affecting one or more other properties. These unique properties bring forward a new encoding technology, e.g., for a wide range of high-throughput bioanalytical applications.

As used herein and unless otherwise indicated, the terms "a" and "an" are taken to mean "one," "at least one" or "one or more". Unless otherwise required by context, singular terms used herein shall include pluralities and plural terms shall include the singular.

In some aspects, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together. As used herein, the term "heteroalkyl" refers to a straight or branched, saturated, aliphatic radical of carbon atoms, where at least one of the carbon atoms is replaced with a heteroatom, such as N, O or S. Additional heteroatoms can also be useful, including, but not limited to, B, Al, Si and P.

In some aspects, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

In some aspects, the term "alkoxy" refers to an alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

In some aspects, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

In some aspects, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

In some aspects, the term "alkyl amine" refers to an alkyl group as defined within, having one or more amino groups. The amino groups can be primary, secondary or tertiary. The alkyl amine can be further substituted with a hydroxy group. Alkyl amines can include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

In some aspects, the term "halogen" or "halide" refers to fluorine, chlorine, bromine and iodine. As used herein, the term "haloalkyl" refers to alkyl as defined above where some or all of the hydrogen atoms are substituted with halogen atoms. Halogen (halo) preferably represents chloro or fluoro, but may also be bromo or iodo. As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, and the like.

In some aspects, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

In some aspects, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

In some aspects, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —$S(O)_2$—.

In some aspects, the term "heterocycloalkylene" refers to a heterocycloalkyl group, as defined above, linking at least two other groups. The two moieties linked to the heterocycloalkylene can be linked to the same atom or different atoms of the heterocycloalkylene.

In some aspects, the term "aryl" refers to a monocyclic or fused bicyclic, tricyclic or greater, aromatic ring assembly containing 6 to 16 ring carbon atoms. For example, aryl may be phenyl, benzyl, azulenyl or naphthyl. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g., methylenedioxy or ethylenedioxy. Oxy-$C_2$-$C_3$-alkylene is also a divalent substituent attached to two adjacent carbon atoms of phenyl, e.g., oxyethylene or oxypropylene. An example for oxy-$C_2$-$C_3$-alkylene-phenyl is 2,3-dihydrobenzofuran-5-yl.

Aryl groups can include, but are not limited to, naphthyl, phenyl or phenyl mono- or disubstituted by alkoxy, phenyl, halogen, alkyl or trifluoromethyl, phenyl or phenyl-mono- or disubstituted by alkoxy, halogen or trifluoromethyl, and in particular phenyl.

In some aspects, the terms "alkoxy-aryl" refers to an aryl group, as defined above, where one of the moieties linked to the aryl is linked through an oxygen atom. Alkoxy-aryl groups include, but are not limited to, phenoxy ($C_6H_5O$—). The present disclosure also includes alkoxy-heteroaryl groups.

In some aspects, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g., alkyl, nitro or halogen. Similarly, aryl and heteroaryl groups described herein can be substituted or unsubstituted. Substituents for the aryl and heteroaryl groups are varied, such as alkyl, aryl, CN, amino, sulfide, aldehyde, ester, ether, acid, hydroxyl or halide. Substituents can be a reactive group, such as but not limited to chloro, bromo, iodo, hydroxyl, or amino. Substituents can be selected from: halogen, OR', OC(O)R', NR'R", SR', R', CN, $NO_2$, $CO_2R'$, CONR'R", C(O)R', OC(O)NR'R", NR"C(O)R', NR"C(O)$_2$R', NR'C(O)NR"R'", NHC($NH_2$)=NH, NR'C($NH_2$)=NH, NHC($NH_2$)=NR', S(O)R', S(O)$_2$R', S(O)$_2$NR'R", $N_3$, CH(Ph)$_2$, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

The groups described herein can be substituted or unsubstituted. Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups, such as alkyl, aryl, cyano (CN), amino, sulfide, aldehyde, ester, ether, acid, hydroxyl or halide. Substituents can be a reactive group, such as but not limited to chloro, bromo, iodo, hydroxyl, or amino. Suitable substituents can be selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Optical Properties of Encoded Chromophoric Polymer Particles

Certain aspects of the present disclosure provide chromophoric polymer particles suitable for use as an encoding platform. In some aspects, the present disclosure provides chromophoric polymer particles capable of optical encoding and/or biomolecular encoding, also referred to herein as "encoded chromophoric polymer particles" or "encoded polymer particles." In some aspects, an encoded chromophoric polymer particle has an optically detectable code, also referred to herein as an "optical code" or "optical encoding," which enables the particle to be optically distinguished from particles having a different code. Various types of optical encoding schemes are suitable for use with the encoded chromophoric polymer particles described herein. In certain aspects, the optically detectable code includes one or more optical properties of the polymer particle, such as a predetermined emission spectrum of the polymer particle (e.g., emission wavelength, emission intensity), a predetermined emission lifetime of the polymer particle, a predetermined emission rate, a predetermined absorption wavelength, or a combination thereof. Accordingly, an encoded chromophoric polymer particle can be uniquely identified by measuring its optical properties in order to determine the corresponding code.

In various aspects of the present disclosure, the optically detectable code is defined by the chromophores of the encoded chromophoric polymer particle. The encoded chromophoric polymer particle can include any suitable number and combination of the various chromophore compositions provided herein. For instance, exemplary chromophores suitable for use with the present disclosure include but are not limited to chromophoric polymers (e.g., one or more chromophoric polymers forming the polymer matrix of the particle, such as narrow-band chromophoric polymers), lanthanide chromophores (e.g., lanthanide ions, lanthanide complexes, lanthanide nanoparticles, or other lanthanide materials), or chromophoric dyes (e.g., fluorescent dyes, luminescent dyes), as described further herein.

In some aspects, because of the unique feature that chromophoric polymers are used as the polymer matrix, the present disclosure provides chromophoric particles for encoding where the entire particle is composed of chromophores (e.g., fluorescent and/or luminescent materials such as chromophoric polymers, lanthanide chromophores, or chromophoric dyes). In some aspects, up to 90% of the mass of each particle is composed of chromophores. In some aspects, up to 80% of the mass of each particle is composed of chromophores. In some aspects, up to 70% of the mass of each particle is composed of chromophores. In some aspects, up to 60% of the mass of each particle is composed of chromophores. In some aspects, up to 50% of the mass of each particle is composed of chromophores. In some aspects, up to 40% of the mass of each particle is composed of chromophores. In some aspects, up to 30% of the mass of each particle is composed of chromophores. In some aspects, up to 20% of the mass of each particle is composed of chromophores. In some aspects, up to 10% of the mass of each particle is composed of chromophores. In some aspects, the encoded chromophoric polymer particle includes a plurality of distinct chromophores and the combined mass of the plurality of distinct chromophores is between 1% and 99%, 10% and 99%, 20% and 99%, 30% and 99%, 40% and 99%, or 50% and 99% of the total mass of the polymer particle. In certain aspects, the chromophores can be chromophoric polymers alone. In other aspects, the chromophores can include chromophoric polymers physically blended or chemically cross-linked with other chromophore types, e.g., lanthanide materials such as lanthanide ions, lanthanide complexes, lanthanide nanoparticles, chromophoric dyes such as fluorescent dyes, or combinations thereof.

In some aspects, the encoded chromophoric polymer particle includes one or more distinct chromophores (e.g., chromophores having different structures, compositions, and/or properties) that are used to define the optically detectable code. The encoded chromophoric polymer particle can include any suitable number and combination of distinct chromophore types, such as only a single distinct chromophore, two or more distinct chromophores, three or more or more distinct chromophores, four or more distinct chromophores, five or more distinct chromophores, six or more distinct chromophores, seven or more distinct chromophores, eight or more distinct chromophores, nine or more distinct chromophores, ten or more distinct chromophores, twenty or more distinct chromophores, fifty or more distinct chromophores, or one hundred or more distinct chromophores. In some aspects, the encoded chromophoric polymer particle comprises a fixed mass ratio between any of the distinct chromophores in the plurality of distinct chromophores, such as a fixed mass ratio between two or more distinct chromophores, three or more or more distinct chromophores, four or more distinct chromophores, five or more distinct chromophores, six or more distinct chromophores, seven or more distinct chromophores, eight or more distinct chromophores, nine or more distinct chromophores, ten or more distinct chromophores, twenty or more distinct chromophores, fifty or more distinct chromophores, or one hundred or more distinct chromophores.

In certain aspects, distinct chromophores have one or more optical properties (e.g., emission spectra, emission intensities, emission wavelengths, emission lifetimes, emission rates, absorbance wavelengths, etc.) that are distinguishable from one another. For example, an encoded chromophoric polymer particle can include a polymer matrix (e.g., formed from at least one chromophoric polymer) and one or more chromophores (e.g., lanthanide chromophores) having optical properties that are distinguishable from the optical properties of the polymer matrix. In some aspects, an encoded chromophoric polymer particle includes two or more, three or more, four or more, five or more, six or more, seven or more, eight or more, nine or more, or ten or more distinct chromophores having emission spectra that are distinguishable from each other. In some aspects, the encoded chromophoric polymer particle includes two or more, three or more, four or more, five or more, six or more, seven or more, eight or more, nine or more, or ten or more distinct chromophores having emission intensities that are distinguishable from each other. In some aspects, the encoded chromophoric polymer particle includes two or more, three or more, four or more, five or more, six or more, seven or more, eight or more, nine or more, or ten or more distinct chromophores having emission wavelengths that are distinguishable from each other. In some aspects, the encoded chromophoric polymer particle includes two or more, three or more, four or more, five or more, six or more, seven or more, eight or more, nine or more, or ten or more distinct chromophores having emission lifetimes that are distinguishable from each other.

In certain aspects, distinct chromophores have one or more optical properties (e.g., emission spectra, emission intensities, emission wavelengths, emission lifetimes, etc.) that are independently or semi-independently controllable. In some aspects, the encoded chromophoric polymer particle includes two or more, three or more, four or more, five or more, six or more, seven or more, eight or more, nine or more, or ten or more distinct chromophores having emission spectra that are independently or semi-independently controllable. In some aspects, the encoded chromophoric polymer particle includes two or more, three or more, four or more, five or more, six or more, seven or more, eight or more, nine or more, or ten or more distinct chromophores having emission intensities that are independently or semi-independently controllable. In some aspects, the encoded chromophoric polymer particle includes two or more, three or more, four or more, five or more, six or more, seven or more, eight or more, nine or more, or ten or more distinct chromophores having emission wavelengths that are independently or semi-independently controllable. In some aspects, the encoded chromophoric polymer particle includes two or more, three or more, four or more, five or more, six or more, seven or more, eight or more, nine or more, or ten or more distinct chromophores having emission lifetimes that are independently or semi-independently controllable.

In certain aspects, various optical properties of the chromophores, which may be referred to herein as "optical coding parameters," are tunable so as to allow for a plurality of distinct optical codes (e.g., optical codes that are optically distinguishable from each other). As described further herein, the tunable optical coding parameters of a chromophore can include one or more optical properties of the chromophore, such as an emission peak intensity, an emission peak wavelength, an emission lifetime, an emission rate, an absorption peak wavelength, or combinations thereof. In certain aspects, the tunable optical coding parameters for each distinct chromophore are predetermined (e.g., have a value, profile, characteristic, etc. that is predetermined based on the structure and/or composition of the chromophore) in order to provide a defined optically detectable code for the polymer particle.

Various numbers and combinations of tunable optical coding parameters are suitable for use with the approaches described herein. In some aspects, a set of tunable optical coding parameters of a chromophore includes only a single tunable optical coding parameter. In other aspects, a set of tunable optical coding parameters includes at least two unique tunable optical coding parameters, at least three unique tunable optical coding parameters, at least four unique tunable optical coding parameters, at least five unique tunable optical coding parameters, at least six unique tunable optical coding parameters, at least seven unique tunable optical coding parameters, at least eight unique tunable optical coding parameters, at least nine unique tunable optical coding parameters, at least ten unique tunable optical coding parameters, at least twenty unique tunable optical coding parameters, at least fifty unique tunable optical coding parameters, or at least one hundred unique tunable optical coding parameters.

In certain aspects, each distinct chromophore is associated with a set of tunable optical coding parameters and at least some the sets of tunable optical coding parameters are independently or semi-independently tunable or modulatable. In some aspects, "tuned independently" means that one tunable optical coding parameter is not affected by another tunable optical coding parameter (e.g., one set of emission peaks is not affected by another set of emission peaks). In some aspects, "tuned semi-independently" means that one tunable optical coding parameter can be affected by another tunable optical coding parameter (e.g., one set of emission peaks can be affected by another set of emission peaks). Examples of optical coding parameters that are "tuned semi-independently" include cases where energy transfer is employed to adjust and tune the emission intensity of the polymer particles, where the polymer particles comprise donor molecules and acceptor molecules (e.g., Example 7 provided below). For example, in some aspects, the sets of tunable optical coding parameters of two or more distinct chromophores, three or more or more distinct chromophores, four or more distinct chromophores, five or more distinct chromophores, six or more distinct chromophores, seven or more distinct chromophores, eight or more distinct chromophores, nine or more distinct chromophores, ten or more distinct chromophores, twenty or more distinct chromophores, fifty or more distinct chromophores, or one hundred or more distinct chromophores are independently or semi-independently tunable or modulatable.

The optically detectable code of an encoded chromophoric polymer particle can be defined based on any suitable number and combination of tunable optical coding parameters. In some aspects, the optically detectable code is defined according to a single tunable optical coding parameter (e.g., emission peak wavelength only ("wavelength encoding"), emission peak intensity only ("intensity encoding"), emission lifetime only ("lifetime encoding"), etc.) In other aspects, the optically detectable code is defined according to two tunable optical coding parameters (e.g., emission peak wavelength and emission peak intensity ("wavelength-intensity encoding"), emission peak wavelength and emission lifetime ("wavelength-lifetime encoding"), emission peak intensity and emission lifetime ("intensity-lifetime encoding")). In alternative aspects, the optically detectable code is defined according to three tunable optical coding parameters (e.g., emission peak wavelength, emission peak intensity, and emission lifetime ("wavelength-intensity-lifetime encoding")). In some aspects, the optically detectable code is defined according to four tunable optical coding parameters, five tunable optical coding parameters, six tunable optical coding parameters, seven tunable optical coding parameters, eight tunable optical coding parameters, nine tunable optical coding parameters, ten tunable optical coding parameters, or more than ten tunable optical coding parameters.

In certain aspects, the optically detectable code includes a predetermined set of emission peaks of the encoded chromophoric polymer particle. In some aspects, the chemical composition and structure of the encoded chromophoric particle comprise at least two distinct chromophores (e.g., at least one type of chromophoric polymer and one type of lanthanide chromophore, at least one type of chromophoric polymer and one type of fluorescent dye) which are tuned to obtain at least two sets of emission peaks for the polymer particle. In some aspects, the encoded chromophoric polymer particles have at least two sets, at least three sets, at least four sets, at least five sets, at least six sets, at least seven sets, at least eight sets, at least nine sets, or at least ten sets of emission peaks generated by tuning a corresponding number of chromophores.

In one preferable aspect, the chromophoric polymer particle can have multiple, e.g., 2-10, sets of well-resolved emission peaks, in which any two neighboring emission peaks do not have spectral overlap. The intensity levels of each emission peak can be tuned independently by adjusting the particle composition and/or polymer structure. However, in certain aspects, the chromophoric polymer particle can have multiple emission peaks, and there may be some spectral overlap between two neighboring emission peaks. In some aspects, the overlapped area is less than 1% of the integrated area of any one of the two neighboring peaks. In some aspects, the overlapped area is less than 5% of the integrated area of any one of the two neighboring peaks. In some aspects, the overlapped area is less than 10% of the integrated area of any one of the two neighboring peaks. In some aspects, the overlapped area is less than 20% of the integrated area of any one of the two neighboring peaks. In some aspects, the overlapped area is less than 30% of the integrated area of any one of the two neighboring peaks. In some aspects, the overlapped area is less than 40% of the integrated area of any one of the two neighboring peaks.

In another preferable aspect, the encoded chromophoric polymer particle can have multiple, e.g., 2-10, sets of emission peaks, and each peak originates from one chromophore (e.g., a fluorescent species) in the particle. In certain aspects, the intensity levels of each emission peak can be tuned independently, e.g., by adjusting the particle composition and/or polymer structure. In certain aspects, the chromophoric polymer particle can have multiple emission peaks, but two or more than two emission peaks can originate from one chromophore species and the other emission peaks are from different species. The intensity levels of the emission peaks from one chromophore species can be correlated and tuned by adjusting the particle composition and polymer structure.

In some aspects, the chromophoric polymer particle shows multiple, e.g., 2-10, sets of emission peaks under one-wavelength excitation. In some aspects, the chromophoric polymer particle shows multiple sets of emission peaks under two-wavelength excitation. In some aspects, the chromophoric polymer particle shows multiple sets of emission peaks under three-wavelength excitation. In some aspects, the chromophoric polymer particle shows multiple sets of emission peaks under four—or more—wavelength excitation. However, the emission intensity of each set of emission peaks can be independently or semi-independently tuned by varying the particle composition and polymer structure, e.g., the relative intensity of one set of emission peak or peaks versus any of other peaks can be changed independently or semi-independently.

In certain aspects, the emission intensities and/or emission wavelengths of the set of emission peaks of an encoded chromophoric polymer particle can be modulated, thereby allowing for encoding based on peak wavelength and/or intensity. For example, in some aspects, a wavelength encoding scheme provides a plurality of optically detectable codes defined by varying the emission wavelength of the emission peaks of the encoded chromophoric polymer particle. The emission wavelength of the polymer particles can vary from the UV region to the near infrared region. In some aspects, the emission wavelength of each set of emission peak or peaks of the polymer particle is capable of being modulated independently or semi-independently. The emission intensity of each set of emission peak or peaks of the particle can be tuned and adjusted independently or semi-independently. In some aspects, the chromophoric polymer particles include two sets of emission peaks where their wavelengths can be independently or semi-independently tuned. In some aspects, the chromophoric polymer particles include three sets of emission peaks where their wavelengths can be independently or semi-independently tuned. In some aspects, the chromophoric polymer particles include four sets of emission peaks where their wavelengths can be independently or semi-independently tuned. In some aspects, the chromophoric polymer particles include five sets of emission peaks where their wavelengths can be independently or semi-independently tuned. In some aspects, the chromophoric polymer particles include six sets of emission peaks where their wavelengths can be independently or semi-independently tuned. In some aspects, the chromophoric polymer particles include more than six sets of emission peaks where their wavelengths can be independently or semi-independently tuned. In some aspects, the chromophoric polymer particles include up to ten sets of emission peaks where their wavelengths can be independently or semi-independently tuned. In some aspects, the chromophoric polymer particles include more than ten sets of emission peaks where their wavelengths can be independently or semi-independently tuned.

In some aspects, an intensity encoding scheme provides a plurality of optically detectable codes defined varying the emission intensity levels of the emission peaks of the encoded chromophoric polymer particle. In some aspects, the chromophoric polymer particles include two sets of emission peaks where their intensity levels can be independently or semi-independently tuned. In some aspects, the chromophoric polymer particles include three sets of emission peaks where their intensity levels can be independently or semi-independently tuned. In some aspects, the chromophoric polymer particles include four sets of emission peaks where their intensity levels can be independently or semi-independently tuned. In some aspects, the chromophoric polymer particles include five sets of emission peaks where their intensity levels can be independently or semi-independently tuned. In some aspects, the chromophoric polymer particles include six sets of emission peaks where their intensity levels can be independently or semi-independently tuned. In some aspects, the chromophoric polymer particles include more than six sets of emission peaks where their intensity levels can be independently or semi-independently tuned. In some aspects, the chromophoric polymer particles include up to ten sets of emission peaks where their intensity levels can be independently or semi-independently tuned. In some aspects, the chromophoric polymer particles include more than ten sets of emission peaks where their intensity levels can be independently or semi-independently tuned.

In some aspects, a wavelength-intensity encoding scheme provides a plurality of optically detectable codes by varying the emission wavelength and the emission intensity level of the emission peaks of the encoded chromophoric polymer particle. The wavelength-intensity encoding scheme can be any suitable combination of the wavelength encoding schemes and intensity encoding schemes provided herein.

In some aspects, the present disclosure provides encoded chromophoric polymer particles that are capable of lifetime encoding, e.g., have optically detectable codes defined based on the emission lifetime of the polymer particle. In some aspects, the fluorescence lifetime is defined as the average time the molecule (or the particle) stays in its excited state before emitting a photon. Fluorescence lifetime can be experimentally determined from the time constant of a single exponential decay function or the average time constant of a multiexponential decay function of the fluorophore. In certain aspects, the encoded chromophoric polymer particles are capable of wavelength-intensity-lifetime encoding, also known as wavelength-intensity-lifetime multiplexing. As the color and intensity coding can be limited by spectral overlap and background interference, the lifetime coding provides an additional coding dimension. Distinguishable lifetime codes can be generated by varying the compositions of the encoded chromophoric polymer particles. For each single-color emission band, a large number of encoded chromophoric polymer particles can be generated and used as lifetime codes with distinct lifetimes ranging from 10 picoseconds to 1 millisecond.

In some aspects, the encoded chromophoric polymer particles have multiple, e.g., 2-10, sets of emission peaks, and each set of emission peak or peaks have a fluorescence or luminescence lifetime different from others. The lifetime can vary from 10 picoseconds to 1 millisecond. In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond.

In some aspects, the encoded chromophoric polymer particle can include at least one type of chromophoric polymer with distinct lifetimes ranging from 10 picoseconds to 1 millisecond. In some aspects, the encoded chromophoric polymer particle can include at least one type of chromophoric polymer and at least one type of dye molecule, with either the chromophoric polymer or the dye molecules having distinct lifetimes ranging from 10 picoseconds to 1 millisecond. In some aspects, the encoded chromophoric polymer particle can include at least one type of chromophoric polymer and at least two types of dye molecules, either the chromophoric polymer or the dye molecules have distinct lifetimes ranging from 10 picoseconds to 1 millisecond. In some aspects, the encoded chromophoric polymer particle can include at least one type of chromophoric polymer and at least one type of lanthanide material (e.g., lanthanide chromophore), either the chromophoric polymer or the lanthanide material have distinct lifetimes ranging from 10 picoseconds to 1 millisecond. In some aspects, the encoded chromophoric polymer particle can include at least one type of chromophoric polymer, at least one type of dye molecule, and at least one type of lanthanide material. Any of the chromophoric polymer, the dye molecule, and the lanthanide material can have distinct lifetimes ranging from 10 picoseconds to 1 millisecond.

In some aspects, the encoded chromophoric polymer particle can include at least one type of chromophoric polymer for lifetime encoding. The monomer structure, monomer species, and concentration can be varied to tune the lifetimes of the encoded chromophoric polymer particles. The encoded chromophoric polymer particles can include two or more types of chromophoric polymers to generate multiple emission colors and each emission color can be independently used to produce lifetime codes. Energy transfer between the chromophoric polymers can be used to tune the lifetimes of the encoded chromophoric polymer particles.

In some aspects, the encoded chromophoric polymer particle can include at least one type of chromophoric polymer and at least one type of chromophoric dye for lifetime encoding. Either the polymer's emission or the dye's emission can be used independently to produce lifetime codes ranging from 10 picoseconds to 1 millisecond. Energy transfer between the chromophoric polymers and the dye molecules can be used to tune the lifetimes of the encoded chromophoric polymer particles. The dye molecules can be physically associated or chemically linked with the chromophoric polymer. The structure, composition, and concentration of the dyes and the polymers can be varied to tune the lifetimes of the encoded chromophoric polymer particles. The encoded chromophoric polymer particles can include two or more types of dye molecules to generate multiple emission colors and each emission color can be independently used to produce lifetime codes.

For each single-color emission band, a number of chromophoric polymer particles can be generated and used as lifetime codes with distinct lifetimes ranging from 10 picoseconds to 1 millisecond. In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond. Example 5 shows that the dye doped chromophoric polymer particles can be used to produce a number of lifetime codes.

In yet another aspect, the present disclosure provides encoded chromophoric polymer particles with controlled inter-particle energy transfer. Because each particle possesses multiple sets of emission peaks from different fluorescent or luminescent materials, it is desirable in some aspects to control the inter-particle energy transfer so that the intensity levels of each peak or set of peaks can be tuned. In some aspects, the inter-particle energy transfer is completely prevented so that each set of emission peaks can be independently tuned. In some aspects, the inter-particle energy transfer is partially allowed to produce different emission colors and intensity levels.

In some aspects, there is less than 50%, less than 40%, less than 30%, less than 20%, less than 10%, less than 5%, less than 4%, less than 3%, less than 2%, or less than 1% energy transfer between two or more distinct chromophores of the encoded chromophoric polymer particle. In some aspects, there is substantially no energy transfer between two or more distinct chromophores of the encoded chromphoric polymer particle. In some aspects, there is less than 50% percent energy transfer between any of the chromophores present. In some aspects, there is less than 40% percent energy transfer between any of the chromophores present. In some aspects, there is less than 30% percent energy transfer between any of the chromophores present. In some aspects, there is less than 20% percent energy transfer between any of the chromophores present. In some aspects, there is less than 10% percent energy transfer between any of the chromophores present. In some aspects, there is less than 5% percent energy transfer between any of the chromophores present. In some aspects, there is less than 4% percent energy transfer between any of the chromophores present. In some aspects, there is less than 3% percent energy transfer between any of the chromophores present. In some aspects, there is less than 2% percent energy transfer between any of the chromophores present. In some aspects, there is less than 1% percent energy transfer between any of the chromophores present. In some aspects, there is substantially no energy transfer between any of the chromophores present. In some aspects, there is no detectable energy transfer between any of the chromophores present.

In some aspects, the encoded chromophoric polymer particles comprise at least one type of chromophoric polymer for biomolecular encoding. The encoded chromophoric polymer particles can comprise one or more types of conjugated polymers (e.g., semiconducting polymers). The encoded chromophoric polymer particles have at least two sets of emission peaks. The emission wavelength of the polymer particles can vary from UV to near infrared region. The emission intensity of each set of emission peak or peaks of the particle can be tuned and adjusted independently or semi-independently. Exemplary chromophoric polymer compositions are described further herein.

In some aspects, the encoded chromophoric polymer particles include two sets of emission peaks; one set of emission peaks is from the energy donor and the other set of emission peaks is from the energy acceptor, and their intensity levels can be semi-independently tuned by energy transfer. In some aspects, the emission intensities of the donor are greater than those of the acceptor. In some aspects, the emission intensities of the donor are less than those of the acceptor.

In certain aspects, the encoded chromophoric polymer particle can be characterized by their stability. The optical properties (e.g., emission spectrum, emission band width, fluorescence or luminescence quantum yield, fluorescence or luminescence lifetime, emission intensity at a particular wavelength) are stable for over 1 day, or 1 week, or 2 weeks, or 1 month, or 2 months, or 3 months, or 6 months, or 1 year, or longer. The stable fluorescence or luminescence quantum yield means that the fluorescence or luminescence quantum yield of the particles does not change by more than 5%, or 10%, or 20%, or 50%, or higher. The stable emission spectrum means that intensity ratio of the each peak relative to other emission peaks doesn't change by more than 5%, or 10%, or 20%, or 50%, or higher.

In some aspects, the encoded chromophoric polymer particle possess some or all of the following characteristics: (1) multiple sets of, e.g., 2-10, well-resolved emission peaks with minimal spectral overlap; (2) intensity levels of each sets of emission peaks is tuned by adjusting the particle composition and polymer structure; (3) high fluorescence or luminescence quantum yield that is greater than 5%, preferably greater than 10%, preferably greater than 20%, greater than 30%, greater than 40%, greater than 50%, greater than 60%, greater than 70%, greater than 80%, or greater than 90%; (3) each set of emission peaks has a fluorescence or luminescence lifetime different from others; (4) have high stability over at least 2 weeks, preferably 1 month, 2 month, 3 month, 6 months, 1 year, or longer.

As described further herein, the encoded chromophoric polymer particles exhibit multiple sets of emission peaks with their emission intensities tuned independently or semi-independently by varying the compositions of the polymer and lanthanide materials (lanthanide ions, lanthanide complexes, or lanthanide nanoparticles). In some aspects, the mass concentration of the lanthanide materials relative to the entire particle mass is higher than 10%. In some aspects, the mass concentration of the lanthanide materials is higher than 20%. In some aspects, the mass concentration of the lanthanide materials is higher than 30%. In some aspects, the mass concentration of the lanthanide materials is higher than 40%. In some aspects, the mass concentration of the lanthanide materials is higher than 50%. In some aspects, the mass concentration of the lanthanide materials is higher than 60%. In some aspects, the mass concentration of the lanthanide materials is higher than 70%. In some aspects, the mass concentration of the lanthanide materials is higher than 80%. In some aspects, the mass concentration of the lanthanide materials is higher than 90%.

In some aspects, the emission peak(s) of the one or more lanthanide chromophores have shorter wavelengths than the emission peak(s) of the polymer matrix. In some aspects, the emission peak(s) of the one or more lanthanide chromophores have longer wavelengths than the emission peak(s) of the polymer matrix.

In some aspects, the encoded chromophoric polymer particles exhibit multiple sets of emission peaks with their emission lifetime (e.g., fluorescence or luminescence emission lifetime) tuned independently or semi-independently by varying the compositions of the polymer and lanthanide materials (lanthanide ions, lanthanide complexes, or lanthanide nanoparticles). Each set of emission peak or peaks have an emission lifetime different from others. The lifetime can vary from 10 picoseconds to 1 millisecond. In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond. Based on these properties, the encoded chromophoric polymer particles can be used for wavelength-intensity-lifetime encoding. For example, we can separate the chromophoric polymers' fluorescence from the lanthanides' luminescence with time-gated detection or imaging.

In some aspects, the encoded chromophoric polymer particle can include at least one type of chromophoric polymer and at least one type of lanthanide materials for lifetime encoding. The lanthanide materials include lanthanide complexes, lanthanide ions, and lanthanide nanoparticles. Either the polymer's emission or the lanthanide's emission can be used independently to produce lifetime codes ranging from 10 picoseconds to 1 millisecond. Energy transfer between the chromophoric polymers and the lanthanide materials can be used to tune the lifetimes of the encoded chromophoric polymer particles. Energy transfer between different lanthanide ions can also be used to tune the lifetimes of the encoded chromophoric polymer particles. Energy transfer inside lanthanide nanoparticles can also be used to tune the lifetimes of the encoded chromophoric polymer particles. The lanthanide materials can be physically associated or chemically linked with the chromophoric polymer. The structure, composition, and concentrations of the lanthanide materials and the polymers can be varied to tune the lifetimes of the encoded chromophoric polymer particles. The encoded chromophoric polymer particles can include two or more types of lanthanide materials to generate multiple emission colors and each emission color can be independently used to produce lifetime codes. For each single-color emission band, a number of chromophoric polymer particles can be generated and used as lifetime codes with distinct lifetimes ranging from 10 picoseconds to 1 millisecond.

In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond.

In some aspects, the encoded chromophoric polymer particle can include at least one type of chromophoric polymer, at least one type of dye molecules, and at least one type of lanthanide materials for lifetime encoding. The lanthanide materials include lanthanide complexes, lanthanide ions, and lanthanide nanoparticles. Either the polymer's emission, or the dye's emission, or the lanthanide's emission can be used independently to produce lifetime codes ranging from 10 picoseconds to 1 millisecond. Energy transfer between the chromophoric polymers and the lanthanide materials can be used to tune the lifetimes of the encoded chromophoric polymer particles. Energy transfer between the polymers and the dyes can also be used to tune the lifetimes of the encoded chromophoric polymer particles. Energy transfer between the lanthanide materials and the dyes can also be used to tune the lifetimes of the encoded chromophoric polymer particles. Energy transfer inside lanthanide nanoparticles can also be used to tune the lifetimes of the encoded chromophoric polymer particles. The dye molecules, lanthanide materials, and chromophoric polymers can be physically associated or chemically linked with each other. The structure, composition, and concentrations of the polymers, the dyes, and lanthanide materials can be varied to tune the lifetimes of the encoded chromophoric polymer particles. The encoded chromophoric polymer particles can include two or more types of lanthanide materials and two or more types of dyes to generate multiple emission colors and each emission color can be independently used to produce lifetime codes.

For each single-color emission band, a number of chromophoric polymer particles can be generated and used as lifetime codes with distinct lifetimes ranging from 10 picoseconds to 1 millisecond. In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond. Example 6 shows that the encoded chromophoric polymer particles comprising dye molecules and lanthanide complexes can be used to produce a number of lifetime codes.

In some aspects, other tunable optical properties of the encoded chromophoric polymer particle can be used as a basis for optical encoding. For example, the optically detectable code can be based on the overall fluorescence or luminescence quantum yield of the polymer particle. The overall fluorescence or luminescence quantum yield of the encoded chromophoric polymer particle at a given wavelength of excitation can vary from 100% to 1%. In some aspects, the quantum yield is greater than about 90%. In some aspects, the quantum yield is greater than about 80%. In some aspects, the quantum yield is greater than about 70%. In some aspects, the quantum yield is greater than about 60%. In some aspects, the quantum yield is greater than about 50%. In some aspects, the quantum yield is greater than about 40%. In some aspects, the quantum yield is greater than about 30%. In some aspects, the quantum yield is greater than about 20%. In some aspects, the quantum yield is greater than about 10%. In some aspects, the quantum yield is greater than about 5%. In some aspects, the quantum yield is greater than about 1%.

In other aspects, the optically detectable code can be based on the emission rate of a chromophore of the encoded chromophoric polymer particle. In certain aspects, the emission rate of a chromophore ranges from about 10 picoseconds to about 100 picoseconds, from about 100 picoseconds to about 1 nanosecond, from about 1 nanosecond to about 10 nanoseconds, or from about 10 nanoseconds to about 100 nanoseconds.

In other aspects, the optically detectable code can be based on the absorption properties of the encoded chromophoric polymer particle. The absorption peak can shift from the UV region to near infrared region. In some aspects, the encoded chromophoric polymer particle has one absorption peak. In some aspects, the encoded chromophoric polymer particle has two absorption peaks. In some aspects, the encoded chromophoric polymer particle has three absorption peaks. In some aspects, the encoded chromophoric polymer particle has more than three absorption peaks. The absorption peak of the encoded chromophoric polymer particle can be tuned to a certain laser wavelength. In some aspects, for example, the absorption peak is around 266 nanometers. In some aspects the absorption peak is around 355 nanometers. In some aspects, the absorption peak is around 405 nanometers. In some aspects, the absorption peak is around 450 nanometers. In some aspects, the absorption peak is around 488 nanometers. In some aspects, the absorption peak is around 532 nanometers. In some aspects, the absorption peak is around 560 nanometers. In some aspects, the absorption peak is around 635 nanometers. In some aspects, the absorption peak is around 655 nanometers. In some aspects, the absorption peak is around 700 nanometers. In some aspects, the absorption peak is around 750 nanometers. In some aspects, the absorption peak is around 800 nanometers. In some aspects, the absorption peak is around 900 nanometers. In some aspects, the absorption peak is around 980 nanometers. In some aspects, the absorption peak is around 1064 nanometers.

In some aspects, the encoded chromophoric polymer particle has an absorption peak between about 200 nanometers and about 300 nanometers. In some aspects, the encoded chromophoric polymer particle has an absorption peak between about 300 nanometers and about 400 nanometers. In some aspects, the encoded chromophoric polymer particle has an absorption peak between about 400 nanometers and about 500 nanometers. In some aspects, the encoded chromophoric polymer particle has an absorption peak between about 500 nanometers and about 600 nanometers. In some aspects, the encoded chromophoric polymer particle has an absorption peak between about 600 nanometers and about 700 nanometers. In some aspects, the encoded chromophoric polymer particle has an absorption peak between about 700 nanometers and about 800 nanometers. In some aspects, the encoded chromophoric polymer particle has an absorption peak between about 800 nanometers and about 900 nanometers. In some aspects, the encoded chromophoric polymer particle has an absorption peak between about 900 nanometers and about 1000 nanometers. In some aspects, the encoded chromophoric polymer particle has an absorption peak between about 1000 nanometers and about 1100 nanometers. In some aspects, the encoded chromophoric polymer particle has an absorption peak between about 1100 nanometers and about 1200 nanometers.

Chromophoric Polymer Compositions of Encoded Chromophoric Polymer Particles

Various types of chromophoric polymer particles are suitable for use as a platform for the optical encoding and/or biomolecular encoding approaches of the present disclosure. It shall be understood that any description herein referring to chromophoric polymer particles is applicable to the encoded chromophoric polymer particles of the present disclosure. Encoded chromophoric polymer particles can adopt a variety of configurations, including but not limited to, a monolithic polymer particle having a uniform, homogenous composition or a polymer particle having a distinct core and cap structure. The encoded chromophoric polymer particles provided herein may be formed by any method known in the art, including, without limitation, methods relying on precipitation, methods relying on the formation of emulsions (e.g., mini or micro emulsion), and methods relying on condensation. Examples of chromophoric polymer particles suitable for use with the techniques described herein can be found in, for example, PCT application numbers PCT/US2010/056079, PCT/US2012/071767, PCT/US2011/056768, PCT/US2013/024300, and PCT/US2013/063917 and in U.S. patent application Ser. No. 13/687,813, each of which is incorporated herein by reference.

Any suitable number and combination of chromophoric polymer types can be incorporated in the encoded chromophoric polymer particles described herein, such at one or more chromophoric polymers, two or more chromophoric polymers, three or more chromophoric polymers, four or more chromophoric polymers, five or more chromophoric polymers, six or more chromophoric polymers, seven or more chromophoric polymers, eight or more chromophoric polymers, nine or more chromophoric polymers, ten or more chromophoric polymers, fifty or more chromophoric polymers, or one hundred or more chromophoric polymers. The mass concentration of the chromophoric polymers relative to the entire encoded chromophoric polymer particle mass can be varied from 1% to 99%, more preferably between 10% and 99%, more preferably between 20% and 99%, more preferably between 30% and 99%, more preferably between 40% and 99%, and more preferably between 50% and 99%.

In some aspects, the encoded chromophoric polymer particles described herein include a polymer matrix formed from one or more chromophoric polymers. The chromophoric polymer can be a homopolymer or a heteropolymer. In various aspects, the chromophoric polymer can be a semiconducting polymer, a non-semiconducting polymer, or a combination thereof. For example, a number of semiconducting polymers are suitable for use in encoded chromophoric polymer particles according to the present disclosure. Semiconducting polymers have been developed with emission wavelengths ranging from UV to infrared, including the entire visible spectrum. Example of semiconducting polymers include but are not limited to: polyfluorene polymers, including but not limited to poly(9,9-dihexylfluorenyl-2,7-diyl) (PDHF) and poly(9,9-dioctylfluorenyl-2,7-diyl) (PFO); fluorene-based copolymers, including but not limited to, poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2, 1,3}-thiadiazole)] (PFBT), poly[(9,9-dioctylfluorenyl-2,7-diyl)-co-(4,7-Di-2-thienyl-2,1,3-benzothiadiazole)] (PFTBT), and poly[(9,9-dioctylfluorenyl-2,7-diyl)-co-(4,7-Di-2-thienyl-2,1,3-benzothiadiazole)] (PF-0.1TBT); phenylene vinylene polymers, including but not limited to, poly[2-methoxy-5-(2-ethylhexyloxy)-1,4-phenylenevinylene] (MEH-PPV) and poly[2-methoxy-5-(2-ethylhexyloxy)-1,4-(1-cyanovinylene-1,4-phenylene)] (CN-PPV); phenylene ethynylene polymers, including but not limited to, poly(2,5-di(3',7'-dimethyloctyl)phenylene-1,4-ethynylene (PPE); or a combination thereof.

A wide variety of chromophoric polymer structures are suitable for use in accordance with various aspects of the present disclosure. In some aspects, the chromophoric polymer can be a linear polymer. In other aspects, the chromophoric polymer can be a branched polymer. In certain aspects, the chromophoric polymer can be a dendrimer. In certain aspects, the chromophoric polymer can be a brush polymer. In certain aspects, the chromophoric polymer can be a star polymer.

In some aspects, encoded chromophoric polymer particles can be used that contain a polystyrene-based, comb-like polymer. Non-limiting examples of polystyrene based comb-like polymers include polystyrene graft acrylic acid, polystyrene graft ethylene oxide, polystyrene graft butyl alcohol, and the like.

In some aspects, encoded chromophoric polymer particles can be used that contain poly(methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide, and the like.

In some aspects, encoded chromophoric polymer particles can be used that contain a comb-like polymer comprising carboxyl, amine, thiol, ester, succinimidyl ester, azide, alkyne, cyclooctyne, or phosphine groups.

In some aspects, encoded chromophoric polymer particles can be used that contain a polymer functionalized on the terminal monomeric unit, for example with a carboxyl, amine, thiol, ester, succinimidyl ester, azide, alkyne, cyclooctyne, phosphine, or similar functional group. Examples of polymers that can be used include, without limitation, poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

In some aspects, encoded chromophoric polymer particles can be used that contain a copolymer having one or more functionalized monomeric units, for example an amphiphilic polymer, including but not limited to: poly((meth)acrylic acid)-based copolymers such as: poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid); polydiene-based copolymers such as: poly(butadiene(1,2 addition)-b-ethylene oxide), poly(butadiene (1,2 addition)-b-methylacrylic acid, poly(butadiene(1,4 addition)-b-acrylic acid), poly(butadiene(1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly (isoprene-b-ethylene oxide), and poly(isoprene-b-N-methyl 2-vinyl pyridinium iodide); poly(ethylene oxide)-based copolymers such as: poly(ethylene oxide-b-acrylic acid), poly(ethylene oxide-b-acrylamide), poly(ethylene oxide-b-butylene oxide), poly(ethylene oxide-b-c-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline); polyisobutylene-based copolymers such as poly(isobutylene-b-acrylic acid), poly(isobutylene-b-ethylene oxide), poly(isobutylene-b-methacrylic acid); polystyrene based copolymers such as poly(styrene-b-acrylamide), poly(styrene-b-acrylic acid), poly(styrene-b-cesium acrylate), poly (styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate) poly(styrene-b-sodium methacrylate), polyp-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate); polysiloxane-based copolymers such as poly(dimethylsiloxane-b-acrylic acid), poly(dimethylsiloxane-b-ethylene oxide), poly(dimethylsiloxane-b-methacrylic acid); poly(ferrocenyldimethylsilane) based copolymers such as poly(ferrocenyldimethylsilane-b-ethylene oxide); poly(2-vinyl naphthalene)-based copolymers such as poly(2-vinyl naphthalene-b-acrylic acid), poly (vinyl pyridine and N-methyl vinyl pyridinium iodide)-based copolymers such as poly(2-vinyl pyridine-b-ethylene oxide), poly(2-vinyl pyridine-b-methyl acrylic acid), poly (N-methyl 2-vinyl pyridinium iodide-b-ethylene oxide), poly(N-methyl 4-vinyl pyridinium iodide-b-methyl methacrylate), poly(4-vinyl pyridine-b-ethylene oxide) PEO end functional OH; and poly(vinyl pyrrolidone)-based copolymers such as poly(vinyl pyrrolidone-b-D/L-lactide); and the like.

In some aspects of the present disclosure, encoded chromophoric polymer particles used for detection can comprise the polymer, CN-PPV, which is a bright, compact, and orange-emitting semiconducting polymer particle also known as, poly[2-methoxy-5-(2-ethylhexyloxy)-1,4-(1-cyanovinylene-1,4-phenylene)]. CN-PPV has superior fluorescence properties, such as a large absorption cross-section, high quantum yield, and a fast emission rate.

In some aspects, the encoded chromophoric polymer particle used for detecting proteins and peptides can comprise a polymer that consists essentially of CN-PPV. In some aspects, the nanoparticle includes CN-PPV and at least one other material. For example, the CN-PPV can be mixed with a copolymer or other material that provides an additional functionality.

In some aspects, the encoded chromophoric polymer particle used for the detection of proteins and peptides can include a semiconducting copolymer having at least two different chromophoric units. For example, a conjugated copolymer can contain both fluorene and benzothiazole chromophoric units present at a given ratio. Typical chromophoric units used to synthesize semiconducting copolymers include, but are not limited to fluorene unit, phenylene vinylene unit, phenylene unit, phenylene ethynylene unit, benzothiazole unit, thiophene unit, carbazole fluorene unit, boron-dipyrromethene unit, and derivatives thereof. The different chromophoric units can be segregated, as in a block copolymer, or intermingled. In some aspects, a chromophoric copolymer is represented by writing the identity of the major chromophoric species. For example, PFBT is a chromophoric polymer containing fluorene and benzothiazole units at a certain ratio. In some cases, a dash is used to indicate the percentage of the minor chromophoric species and then the identity of the minor chromophoric species. For example, PF-0.1 BT is a chromophoric copolymer containing 90% PF and 10% BT.

In certain aspects, the encoded chromophoric polymer particle can include a blend of semiconducting polymers. The blends can include any combination of homopolymers, copolymers, and oligomers. Polymer blends used to form encoded chromophoric polymer particles may be selected in order to tune the properties of the resulting polymer particles, for example, to achieve a desired excitation or emission spectra for the polymer particle.

For some assays, semiconducting encoded chromophoric polymer particles offer improved detection sensitivity in part because they exhibit higher quantum yields than other fluorescent reporters. In some aspects, the quantum yield of the chromophoric polymer particle used is more than 20%, more than 30%, more than 40%, more than 50%, more than 60%, more than 70%, more than 80%, or more than 90%.

For some assays, semiconducting encoded chromophoric polymer particles offer improved detection sensitivity in part because they exhibit faster emission rates than other fluorescent reporters. In certain aspects, the emission rate of the encoded chromophoric polymer particle used is between about 100 picoseconds and about 50 nanoseconds.

In some aspects, the encoded chromophoric polymer particle used comprises polymers bearing units of small organic dye molecules, metal complexes, photochromic dye, and any combinations thereof, for example, optically inactive polymers such as polystyrene covalently linked or grafted with small organic dye, metal complexes, photochromic dyes and any combination thereof. These dyes or metal complexes may have protein sensing capability.

In some aspects, the encoded chromophoric polymer particles comprise semiconducting polymers covalently linked with small organic dye molecules, metal complexes, photochromic dyes, and any combinations thereof as emissive units. Such emissive units can tune the emission color, increase the quantum yield, and improve the photostability of the chromophoric polymer particle.

In some aspects, the small organic dyes, or metal complexes can have sensing functions, and therefore add additional functionalities to the encoded chromophoric polymer particle, such as protein sensing capability.

In some aspects, the encoded chromophoric polymer particle may comprise a semiconducting polymer physically mixed or chemically cross-linked with other chromophoric polymers such as optically inactive polymer covalently linked or grafted with small organic dye, metal complexes, photochromic dyes and any combination thereof, to have additional functionalities such as protein sensing.

In some aspects, the chromophoric polymer particle may comprise semiconducting polymers physically mixed or chemically cross-linked with other components such as fluorescent dyes, inorganic luminescent materials, magnetic materials, metal materials, and the like in order to tune emission color, improve quantum yield and/or photostability, and/or provide additional functionalities such as magnetic functions, plasmon resonance functions, and the like.

The optical properties, such as absorption wavelength, for a given chromophoric polymer particle can be tuned by modifying its composition and geometry. Semiconducting polymers have been developed with absorption wavelengths ranging from UV to infrared, including the entire visible spectrum. In some aspects, encoded chromophoric polymer particles having a peak absorption wavelength between about 200 nanometers and about 300 nanometers, about 250 nanometers and about 350 nanometers, about 300 nanometers and about 400 nanometers, about 350 nanometers and about 450 nanometers, between about 400 nanometers and about 500 nanometers, about 450 nanometers and about 550 nanometers, about 500 nanometers and about 600 nanometers, about 550 nanometers and about 650 nanometers, about 600 nanometers and about 700 nanometers, about 650 nanometers and about 750 nanometers, about 700 nanometers and about 800 nanometers, about 750 nanometers and about 850 nanometers, about 800 nanometers and about 900 nanometers, about 850 nanometers and about 950 nanometers, or about 900 nanometers and about 1000 nanometers are used.

Semiconducting polymers have been developed with emission wavelengths ranging from UV to infrared, including the entire visible spectrum. In some aspects, encoded chromophoric polymer particles having a peak emission wavelength between about 200 nanometers and about 300 nanometers, about 250 nanometers and about 350 nanometers, about 300 nanometers and about 400 nanometers, about 350 nanometers and about 450 nanometers, about 400 nanometers and about 500 nanometers, about 450 nanometers and about 550 nanometers, about 500 nanometers and about 600 nanometers, about 550 nanometers and about 650 nanometers, about 600 nanometers and about 700 nanometers, about 650 nanometers and about 750 nanometers, about 700 nanometers and about 800 nanometers, about 750 nanometers and about 850 nanometers, about 800 nanometers and about 900 nanometers, about 850 nanometers and about 950 nanometers, about 900 nanometers and about 1000 nanometers, about 950 nanometers and about 1050 nanometers, about 1000 nanometers and about 1100 nanometers, about 1150 nanometers and about 1250 nanometers, or about 1200 nanometers and about 1300 nanometers are used.

In some aspects, the present disclosure provides encoded chromophoric polymer particles with narrow-band emissions. Narrow-band emissions are advantageous for certain applications, including but not limited to multiplexing applications. The emission wavelength of the polymer particles can vary from ultraviolet to near infrared region. In some aspects, the full width at half maximum (FWHM) of the emission band is less than 70 nanometers. In some aspects, the FWHM is less than about 65 nanometers. In some aspects, the FWHM is less than about 60 nanometers. In some aspects, the FWHM is less than about 55 nanometers. In some aspects, the FWHM is less than about 50 nanometers. In some aspects, the FWHM is less than about 45 nanometers. In some aspects, the FWHM is less than about 40 nanometers. In some aspects, the FWHM is less than about 35 nanometers. In some aspects, the FWHM is less than about 30 nanometers. In some aspects, the FWHM is less than about 25 nanometers. In some aspects, the FWHM is less than about 20 nanometers. In some aspects, the FWHM is less than about 10 nanometers. In some aspects, the FWHM of the polymer particles described herein can range between about 5 nanometers to about 70 nanometers, from about 10 nanometers to about 60 nanometers, from about 20 nanometers to about 50 nanometers, or from about 30 nanometers to about 45 nanometers.

In some aspects, the variety of encoded chromophoric polymer particles of the present disclosure can include polymers that have a narrow band emissive unit (e.g., a narrow band monomer and/or a narrow band unit). For example, the present disclosure can include a homopolymer or heteropolymer including a narrow band monomer, such as BODIPY and/or BODIPY derivative monomer, a squaraine and/or squaraine derivative monomer, a metal complex and/or metal complex derivative monomer, a porphyrin and/or porphyrin derivative monomer, a metalloporphyrin and/or metalloporphyrin derivative monomer, a phthalocyanine and/or phthalocynanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer. A narrow band unit can be, e.g., a narrow band monomer or a fluorescent nanoparticle embedded in or attached to the polymer particle. The fluorescent nanoparticle can be, e.g., a quantum dot. A narrow band unit can also include a polymer or fluorescent dye molecule that gives a narrow emission in a polymer particle of the present disclosure.

As will be appreciated by one of ordinary skill in the art, the various chemical terms defined herein can be used for describing chemical structures of the polymers and monomers of the present disclosure. For example, a variety of the monomer derivatives (e.g., BODIPY derivatives) can include a variety of the chemical substituents and groups described herein. For example, in some aspects, derivatives of the various monomers can be substituted with hydrogen, deuterium, alkyl, aralkyl, aryl, alkoxy-aryl, N-dialkyl-4-phenyl, N-diphenyl-4-phenyl, N-dialkoxyphenyl-4-phenyl, amino, sulfide, aldehyde, ester, ether, acid, and/or hydroxyl.

In some aspects, the narrow-band emissive polymers for making chromophoric polymer particles include boron-dipyrromethene (4,4-difluoro-4-bora-3a,4a-diaza-s-indacene, BODIPY) and or their derivatives, and/or other boron-containing monomers and their derivatives, as narrow-band monomers. BODIPY and other boron containing monomers and their derivatives include but are not limited to their alkyl derivatives, aryl derivatives, alkyne derivatives, aromatic derivatives, alkoxide derivatives, aza derivatives, BODIPY extended systems and other BODIPY derivatives. The narrow-band emissive polymers can also include any other monomers. The BODIPY based-monomers can be energy acceptors and other monomers can be energy donors so that the final chromophoric polymer particles can exhibit narrow-band emissions. The narrow-band emissive chromophoric polymers in good solvents may exhibit broad emissions or narrow emissions. A comprehensive description of chromophoric polymer particles with narrow-band emissions, including BODIPY and other boron containing monomers and their derivatives, is described in PCT/US2012/071767, which is herein incorporated by reference in its entirety.

A variety of other BODIPY derivatives can be used for the present disclosure. BODIPY and BODIPY derivatives can be polymerized to form polymers (e.g., homopolymers or heteropolymers) and/or can be attached (e.g., covalently attached) to a polymer backbone, sidechain and/or terminus.

In some aspects, the encoded chromophoric polymer particles of the present disclosure include a polymer that includes a narrow-band monomer having the structure of Formula (I):

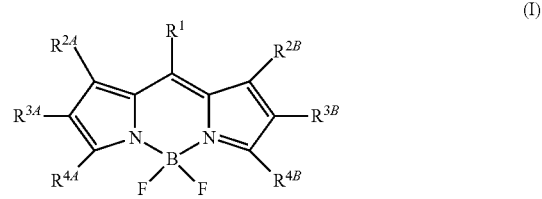

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and $-(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer)

and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, or a combination thereof.

In some aspects, the encoded chromophoric polymer particles of the present disclosure include a polymer that includes a narrow-band monomer having the structure of Formula (II):

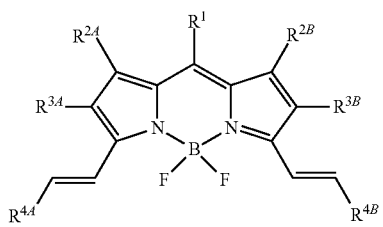

(II)

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, or a combination thereof. The monomer can, for example, integrate with the backbone of the polymer by attachment to the $R^{3A}$ and $R^{3B}$ groups.

In some aspects, the encoded chromophoric polymer particles of the present disclosure include a polymer that includes a narrow-band monomer having the structure of Formula (III):

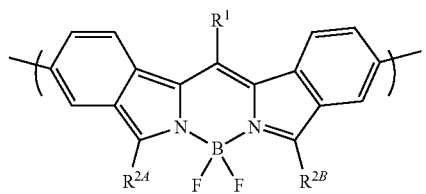

(III)

wherein each of $R^1$, $R^{2A}$ and $R^{2B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-) substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment, e.g., to $R^1$, $R^{2A}$, $R^{2B}$, or a combination thereof. The parentheses indicate points of attachment of the monomer to the backbone of the polymer.

In some aspects, the encoded chromophoric polymer particles of the present disclosure include a polymer that includes a narrow-band monomer having the structure of Formula (IV):

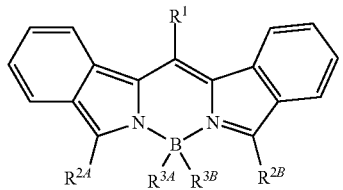

(IV)

wherein each of $R^1$, $R^{2A}$, $R^{2B}$, $R^{3A}$, and $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, and $R^{3B}$ or a combination thereof.

In some aspects, the encoded chromophoric polymer particles of the present disclosure include a polymer that includes a narrow-band monomer having the structure of Formula (V):

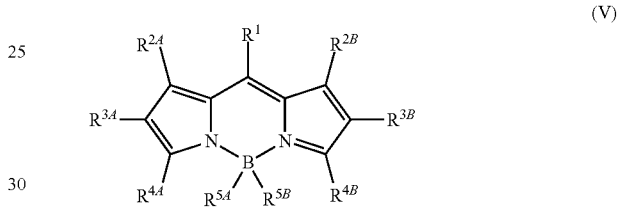

(V)

wherein each of $R^1$, $R^{2A}$, $R^{2B}$, $R^{3A}$, $R^{3B}$, $R^{4A}$, $R^{4B}$, $R^{5A}$, and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, $R^{5A}$, $R^{5B}$, or a combination thereof. In certain aspects, the narrow-band monomers can be integrated into the backbone by attachment to the $R^{5A}$ and $R^{5B}$ groups.

In some aspects, the encoded chromophoric polymer particles of the present disclosure include a polymer that includes a narrow-band monomer having the structure of Formula (VI):

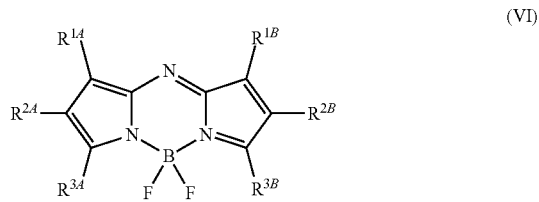

(VI)

wherein each of $R^{1A}$, $R^{1B}$, $R^{2A}$, $R^{2B}$, $R^{3A}$ and $R^{3B}$ is independently selected from the group consisting of, but not limited to, hydrogen (H), deuterium (D), halogen, direct or branched alkyl, heteroalkyl, heterocycloalkyl, heterocloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkylalkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkylalkoxy-, aryl-, fluoroalkyl-, fluoroaryl-) substituted tripyridyl, furyl, alkylalkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkylalkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkylalkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkylalkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkylalkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^{1A}$, $R^{1B}$, $R^{2A}$, $R^{2B}$, $R^{3A}$, $R^{3B}$, or a combination thereof.

In some aspects, the encoded chromophoric polymer particles of the present disclosure include a polymer that includes a narrow-band monomer having the structure of Formula (VII):

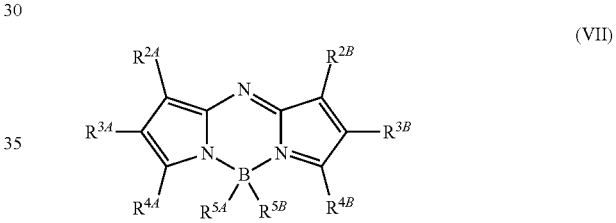

(VII)

wherein each of $R^{2A}$, $R^{2B}$, $R^{3A}$, $R^{3B}$, $R^{4A}$, $R^{4B}$, $R^{5A}$ and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl The narrow-band monomer can be integrated into a backbone of the polymer (e.g., polymerized in the polymer) and/or covalently attached to the backbone, a terminus, or a sidechain of the polymer) through at least one attachment to $R^{2A}$, $R^{2B}$, $R^{3A}$, $R^{3B}$, $R^{4A}$, $R^{4B}$, $R^{5A}$, $R^{5B}$, or a combination thereof.

In some aspects, the encoded chromophoric polymer particles of the present disclosure include a polymer that includes a narrow-band monomer having the structure of Formula (VIII):

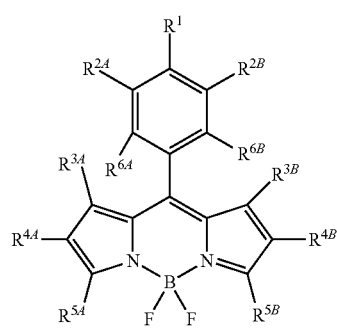

(VIII)

wherein each of $R^{1A}$, $R^{1B}$, $R^{2A}$, $R^{2B}$, $R^{3A}$, $R^{3B}$, $R^{4A}$ and $R^{4B}$, is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-) substituted pyridyl, bipyridyl, alkyl-(alkoxy-, aryl-, fluoroalkyl-, fluoroaryl-)substituted bipyridyl tripyridyl, alkylalkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkylalkoxy-, aryl-, fluoroalkyl-, fluoroaryl-)substituted oxazolyl, thiazolyl, alkylalkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkylalkoxy-, aryl-, fluoroalkyl-, fluoroaryl-)substituted benzothiadizolyl, fluorenyl, alkylalkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl, and wherein each of $R^{5A}$, $R^{5B}$, $R^{6A}$ and $R^{6B}$ are independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —(OCH$_2$CH$_2$)$_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-) substituted pyridyl, bipyridyl, alkyl-(alkoxy-, aryl-, fluoroalkyl-, fluoroaryl-) substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkylalkoxy-, aryl-, fluoroalkyl-, fluoroaryl-)substituted pyrazolyl, oxazolyl, alkylalkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkylalkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkylalkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9- dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer) through at least one attachment to $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$ or a combination thereof.

In some aspects, the encoded chromophoric polymer particles of the present disclosure include a polymer that includes a narrow-band monomer having the structure of Formula (IX):

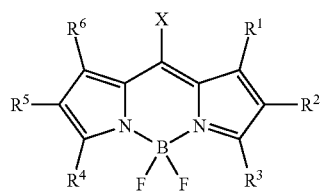
(IX)

wherein X has the structure of any one of Formulae (X), (XI), (XII), and (XIII) or their derivatives:

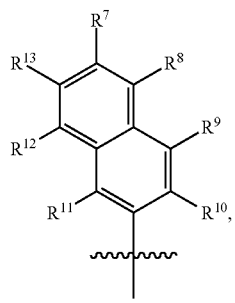
(X)

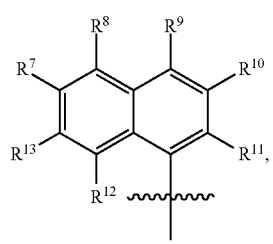
(XI)

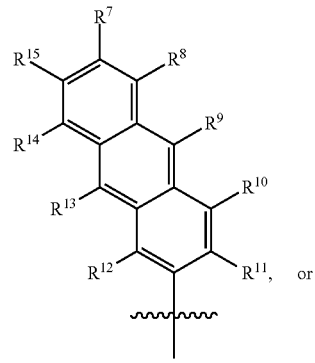
(XII)

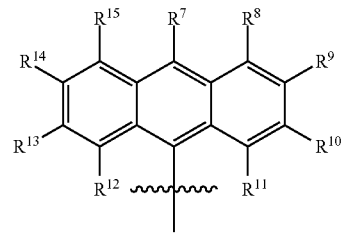
(XIII)

and wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in Formulae (X), (XI), (XII), and (XIII) is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —$(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkylalkoxy-, aryl-, fluoroalkyl-, fluoroaryl-) substituted tripyridyl, furyl, alkylalkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkylalkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkylalkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkylalkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. When X represents naphthalene and its derivatives, the narrow-band monomer can be integrated into a backbone (e.g., polymerized in the polymer) and/or covalently attached to the backbone, a terminus, or a sidechain of the polymer) of the polymer through at least one attachment to $R^7$, $R^8$, $R^9$, $R^{10}$, $R^{11}$, $R^{12}$ or a combination thereof. When X represents anthracene and its derivatives, the narrow-band monomer can be integrated into a backbone of the polymer and/or covalently attached to the backbone, a terminus, or a sidechain of the polymer through at least one attachment to $R^7$, $R^8$, $R^9$, $R^{10}$, $R^{11}$, $R^{12}$, $R^{13}$, $R^{14}$, $R^{15}$ or a combination thereof.

Narrow band monomers of the present disclosure can further include dipyrrin derivatives. Dipyrrin and dipyrrin derivatives can be polymerized to form polymers (e.g., homopolymers or heteropolymers) and/or can be attached (e.g., covalently attached) to a polymer backbone, sidechain and/or terminus. For example, the chromophoric polymer particles of the present disclosure can include a polymer that includes a narrow-band monomer having the structure of Formula (XIV):

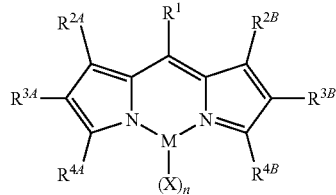

(XIV)

wherein M is a metal. Examples of M can be, but not limited to, Na, Li, Zn, Co, or Si. X can include substituents such as, but not limited to, halogen, alkyl, phenyl, alkylphenyl, thiophenyl, alkylthiophenyl, alkoxyl, alkoxylphenyl, alkylthiophenyl, ester, or hydroxyl. The number of X groups (n) can be 1 or more than 1, and n can be 0, 1, 2, 3, 4. Each of $R^1$, $R^{2A}$, $R^{2B}$, $R^{3A}$, $R^{3B}$, $R^{4A}$, $R^{4B}$, $R^{5A}$, and $R^{5B}$ can be independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and —$(OCH_2CH_2)_n$OH, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer) through at least one attachment to $R^1$, $R^{2A}$, $R^{2B}$, $R^{3A}$, $R^{3B}$, $R^{4A}$, $R^{4B}$, $R^{5A}$, $R^{5B}$, or a combination thereof.

In some aspects, the narrow-band emissive polymers for making encoded chromophoric polymer particles include squaraine and squaraine derivatives as narrow-band monomers. Squaraine derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The squaraine and their derivatives can be energy acceptors and other monomers can be energy donors so that the final chromophoric polymer particles can exhibit narrow-band emissions. The narrow-band emissive chromophoric polymers in good solvents may exhibit broad emissions or narrow emissions. However, in some aspects, their nanoparticle form gives narrow-band emissions. In some aspects, the emission FWHM of the above chromophoric polymer particles is less than 70 nm. In certain aspects, the FWHM is less than 60 nm, less than 50 nm, less than 40 nm, less than 30 nm, or less than 20 nm.

Suitable squaraine derivatives for use in the present disclosure can include the following structures described below. Squaraine and squaraine derivatives can be polymerized to form polymers (e.g., homopolymers or heteropolymers) and/or can be attached (e.g., covalently attached) to a polymer backbone, sidechain and/or terminus. Encoded chromophoric polymer particles of the present disclosure can include a polymer that includes a narrow-band monomer having the structure of Formula (XV):

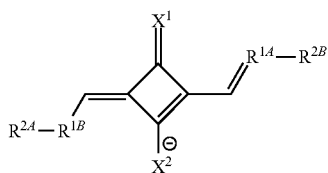

(XV)

wherein each of $X^1$ and $X^2$ is independently selected from the group consisting of oxygen, sulfur and nitrogen; each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; and each of $R^{2A}$ and $R^{2B}$ is a reactive group independently selected from the group consisting of, but not limited to, a halide, hydroxyl, and amino. Other reactive groups can be used. In some aspects, the halide is a chloro, a bromo, or an iodo group. The reactive group can be used to integrate the monomer into a polymer, e.g. along the backbone of the polymer (e.g., by polymerizing in the polymer) and/or to attach the monomer by covalent attachment to the backbone, a terminus, or a sidechain of the polymer. The narrow-band monomer can be integrated into a backbone of the polymer (e.g., polymerized in the polymer) and/or covalently attached to the backbone, a terminus, or a sidechain of the polymer) through at least one attachment to $R^{1A}$, $R^{1B}$, $R^{2A}$, $R^{2B}$, or a combination thereof.

The present disclosure can include oxygen-containing squaraine derivatives. Encoded chromophoric polymer particles of the present disclosure can include a polymer that includes a narrow-band monomer having the structure of Formula (XVI):

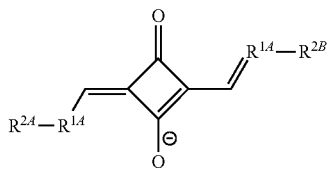

(XVI)

wherein each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; and each of $R^{2A}$ and $R^{2B}$ is a reactive group independently selected from the group consisting of, but not limited to, a halide, hydroxyl, and amino. Other reactive groups can be used. In some aspects, the halide is a chloro, a bromo, or an iodo group. The reactive group can be used to integrate the monomer into a polymer (e.g. along the backbone of the polymer by polymerizing in the polymer) and/or to attach the monomer by covalent attachment to the backbone, a terminus, or a sidechain of the polymer.

Encoded chromophoric polymer particles of the present disclosure can include a polymer that includes a narrow-band monomer having the structure of Formula (XVII):

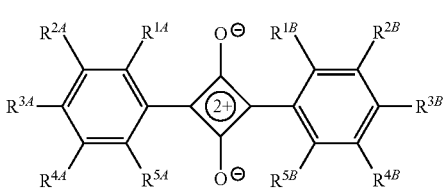

(XVII)

wherein each of $R^{1A}$ and $R^{1B}$ is independently selected from the group consisting of, but not limited to, hydrogen, methyl, alkyl, phenyl, araalkyl, and alkoxy-phenyl; each of $R^{2A}$ and $R^{2B}$ is independently selected from the group consisting of, but not limited to, hydrogen, methyl, alkyl, phenyl, araalkyl, and alkoxy-phenyl; each of $R^{3A}$ and $R^{3B}$ is a reactive group independently selected from the group consisting of, but not limited to, chloro, bromo, iodo, and hydroxyl; each of $R^{4A}$ and $R^{4B}$ is independently is selected from a group consisting of, but not limited to, hydroxyl, hydrogen, alkyl, phenyl, araalkyl, and alkoxy-phenyl; and each of $R^{5A}$ and $R^{5B}$ is independently selected from the group consisting of, but not limited to, hydrogen, methyl, alkyl, phenyl, araalkyl, and alkoxy-phenyl. Other reactive groups can be used. The reactive group can be used to integrate the monomer into a polymer (e.g. along the backbone of the polymer by polymerizing in the polymer) and/or to attach the monomer by covalent attachment to the backbone, a terminus, or a sidechain of the polymer.

Encoded chromophoric polymer particles of the present disclosure can include a polymer that includes a narrow-band monomer having the structure of Formula (XVIII):

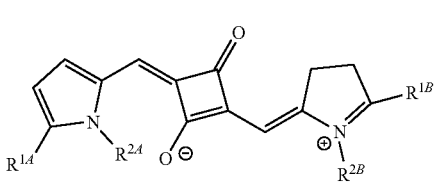

(XVIII)

wherein each of $R^{1A}$ and $R^{1B}$ is a reactive group independently selected from the group consisting of, but not limited to, chloro, bromo, iodo, and hydroxyl; and each of $R^{2A}$ and $R^{2B}$ is selected from the group consisting of, but not limited to, hydrogen, methyl, alkyl, phenyl, araalkyl, and alkoxy-phenyl. Other reactive groups can be used. The reactive group can be used to integrate the monomer into a polymer (e.g. along the backbone of the polymer by polymerizing in the polymer) and/or attach the monomer by covalent attachment to the backbone, a terminus, or a sidechain of the polymer.

Encoded chromophoric polymer particles of the present disclosure can include a polymer that includes a narrow-band monomer having the structure of Formula (XIX):

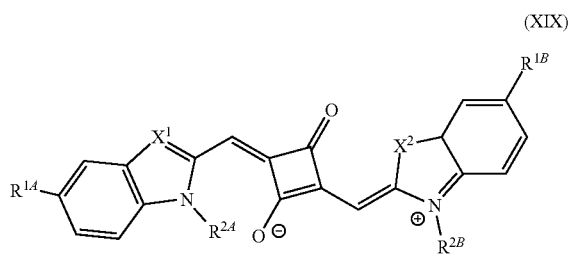

(XIX)

wherein each of $X^1$ and $X^2$ is independently selected from the group consisting of carbon, sulfur, and selenium; each of $R^{1A}$ and $R^{1B}$ is a reactive group independently selected from the group consisting of, but not limited to, chloro, bromo, iodo, and hydroxyl; and each of $R^{2A}$ and $R^{2B}$ is independently selected from the group consisting of, but not limited to, hydrogen, methyl, alkyl, phenyl, araalkyl, alkoxy-phenyl, N-dialkyl-4-phenyl, N-diphenyl-4-phenyl, and N-dialkoxylphenyl-4-phenyl. Other reactive groups can be used. The reactive group can be used to integrate the monomer into a polymer (e.g. along the backbone of the polymer by polymerizing in the polymer) and/or attach the monomer by covalent attachment to the backbone, a terminus, or a sidechain of the polymer.

Encoded chromophoric polymer particles of the present disclosure can include a polymer that includes a narrow-band monomer having the structure of Formula (XX):

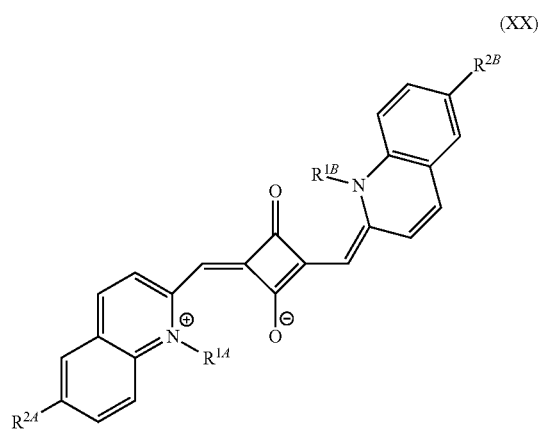

(XX)

wherein each of $R^{2A}$ and $R^{2B}$ is a reactive group independently selected from the group consisting of, but not limited to, chloro, bromo, iodo, and hydroxyl; and each of $R^{1A}$ and $R^{1B}$ is selected from the group consisting of, but not limited to, hydrogen, methyl, alkyl, phenyl, araalkyl, alkoxy-phenyl, N-dialkyl-4-phenyl, N-diphenyl-4-phenyl, and N-dialkoxylphenyl-4-phenyl. Other reactive groups can be used. The reactive group can be used to integrate the monomer into a polymer (e.g. along the backbone of the polymer by polymerizing in the polymer) and/or attach the monomer by covalent attachment to the backbone, a terminus, or a sidechain of the polymer.

The present disclosure can include sulfur-containing squaraine derivatives. Encoded chromophoric polymer particles of the present disclosure can include a polymer that includes a narrow-band monomer having the structure of Formula (XXI):

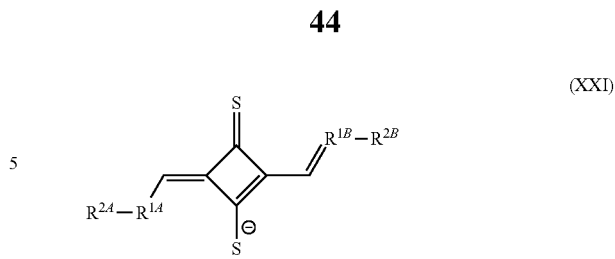

(XXI)

wherein each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; and each of $R^{2A}$ and $R^{2B}$ is a reactive group independently selected from the group consisting of, but not limited to, a halide, hydroxyl, and amino. In some aspects, the halide is a chloro, a bromo, or an iodo group. Other reactive groups can be used. The reactive group can be used to integrate the monomer into a polymer (e.g. along the backbone of the polymer by polymerizing in the polymer) and/or attach the monomer by covalent attachment to the backbone, a terminus, or a sidechain of the polymer.

Encoded chromophoric polymer particles of the present disclosure can include a polymer that includes a narrow-band monomer having the structure of Formula (XXII):

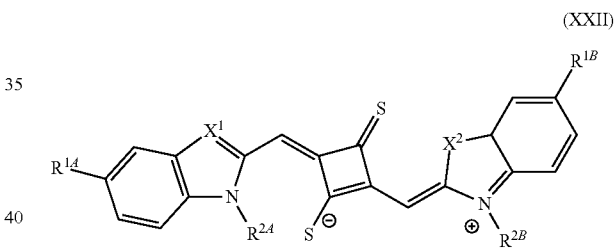

(XXII)

wherein each of $X^1$ and $X^2$ is independently selected from the group consisting of carbon, sulfur, and selenium; each of $R^{1A}$ and $R^{1B}$ is a reactive group independently selected from the group consisting of, but not limited to, chloro, bromo, iodo, and hydroxyl; and each of $R^{2A}$ and $R^{2B}$ is independently selected from the group consisting of, but not limited to, hydrogen, methyl, alkyl, phenyl, araalkyl, alkoxy-phenyl, N-dialkyl-4-phenyl, N-diphenyl-4-phenyl, and N-dialkoxylphenyl-4-phenyl. Other reactive groups can be used. In some aspects, the halide is a chloro, a bromo, or an iodo group. The reactive group can be used to integrate the monomer into a polymer (e.g. along the backbone of the polymer by polymerizing in the polymer) and/or attach the monomer by covalent attachment to the backbone, a terminus, or a sidechain of the polymer.

The present disclosure can include nitrogen-containing squaraine derivatives. Encoded chromophoric polymer particles of the present disclosure can include a polymer that includes a narrow-band monomer having the structure of Formula (XXIII):

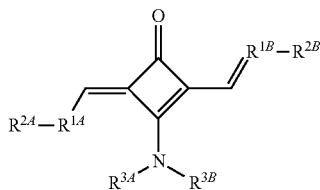

(XXIII)

wherein each of $R^{1A}$ and $R^{1B}$ is independently selected from the group consisting of, but not limited to, alkylene, alkenylene, arylene, heteroarylene, phenylene, azulene, cycloalkylene, and heterocycloalkylene; each of $R^{2A}$ and $R^{2B}$ is a reactive group independently selected from the group consisting of, but not limited to, a halide, hydroxyl, and amino; and each of $R^{3A}$ and $R^{3B}$ is independently selected from the group consisting of hydrogen, methyl, alkyl, phenyl, aralkyl, and alkoxy-phenyl. Other reactive groups can be used. In some aspects, the halide is a chloro, a bromo, or an iodo group. The reactive group can be used to integrate the monomer along into a polymer (e.g. along the backbone of the polymer by polymerizing in the polymer) and/or attach the monomer by covalent attachment to the backbone, a terminus, or a sidechain of the polymer.

Encoded chromophoric polymer particles of the present disclosure can include a polymer that includes a narrow-band monomer having the structure of Formula (XXIV):

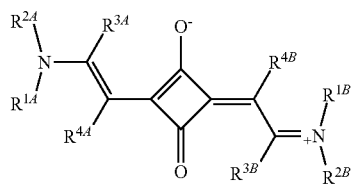

(XXIV)

wherein each of $R^{1A}$, $R^{1B}$, $R^{2A}$ and $R^{2B}$ are independently selected from the group consisting of, but not limited to, hydrogen, deuterium, alkyl, aryl, acetyl, and hydroxyl; and each of $R^{3A}$, $R^{3B}$, $R^{4A}$ and $R^{4B}$ are independently selected from the group consisting of, but not limited to, hydrogen, deuterium, alkyl, aryl, amino, sulfide, aldehyde, ester, ether, acid, hydroxyl, and halide. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{4A}$, $R^{4B}$ or a combination thereof.

Encoded chromophoric polymer particles of the present disclosure can include a polymer that includes a narrow-band monomer having the structure of Formula (XXV):

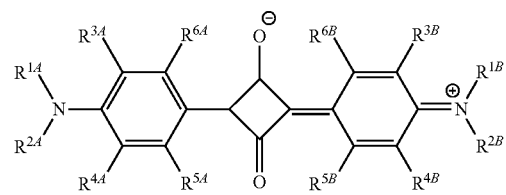

(XXV)

wherein each of $R^{1A}$, $R^{1B}$, $R^{2A}$ and $R^{2B}$ are independently selected from the group consisting of, but not limited to, hydrogen, deuterium, alkyl, aryl, acetyl, and hydroxyl; and each of $R^{3A}$, $R^{3B}$, $R^{4A}$, $R^{4B}$, $R^{5A}$, $R^{5B}$, $R^{6A}$ and $R^{6B}$ are independently selected from the group consisting of, but not limited to, hydrogen, deuterium, alkyl, aryl, amino, sulfide, aldehyde, ester, ether, acid, hydroxyl, and halide. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$ or a combination thereof.

Encoded chromophoric polymer particles of the present disclosure can include a polymer that includes a narrow-band monomer having the structure of Formula (XXVI):

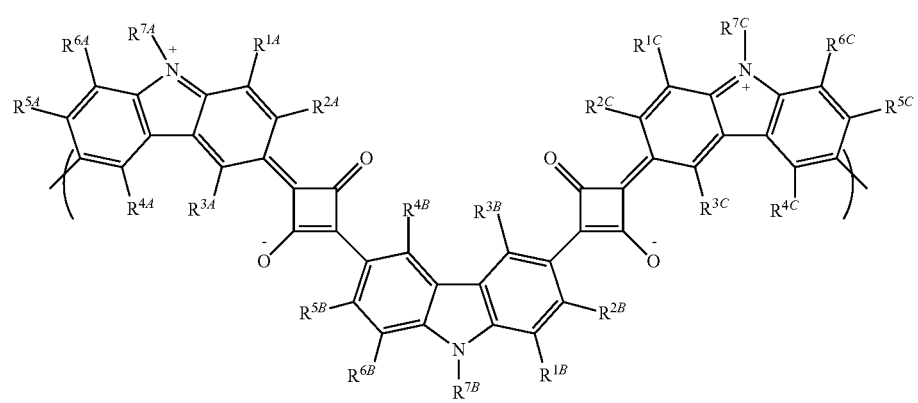

(XXVI)

wherein each of $R^{1A}$, $R^{1B}$, $R^{1C}$, $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, and $R^{6C}$ are independently selected from the group consisting of, but not limited to, hydrogen, deuterium, alkyl, aryl, amino, sulfide, aldehyde, ester, ether, acid, hydroxyl, and halide, and each of $R^{7A}$, $R^{7B}$, and $R^{7C}$ is independently selected from the group consisting of, but not limited to, hydrogen, deuterium, alkyl, aryl and acetyl. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{1A}$, $R^{1B}$, $R^{1C}$, $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, $R^{6C}$, $R^{7A}$, $R^{7B}$ or a combination thereof. Alternatively, as shown here, the monomer described herein can be integrated with the polymer by attachment as shown by the parentheses.

Encoded chromophoric polymer particles of the present disclosure can include a polymer that includes a narrow-band monomer having the structure of Formula (XXVII):

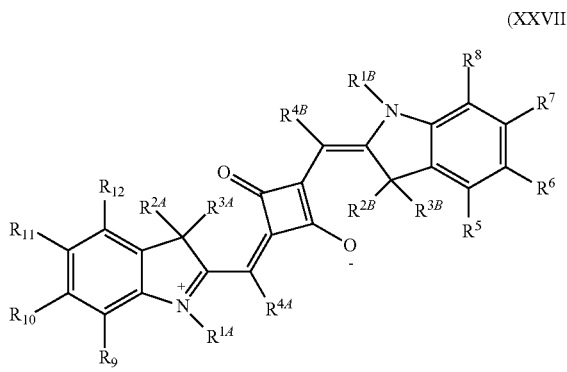

(XXVII)

wherein each of $R^{1A}$ and $R^{1B}$ is independently selected from the group consisting of, but not limited to, hydrogen, deuterium, alkyl and aryl; and each of $R^{2A}$, $R^{2B}$, $R^{3A}$, $R^{3B}$, $R^{4A}$, $R^{4B}$, $R^5$, $R^6$, $R^7$, $R^8$, $R^9$, $R^{10}$, $R^{11}$ and $R^{12}$ are independently selected from the group consisting of, but not limited to, hydrogen, deuterium, alkyl, aryl, cyano, amino, sulfide, aldehyde, ester, ether, acid, hydroxyl, and halide. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{1A}$, $R^{1B}$, $R^{2A}$, $R^{2B}$, $R^{3A}$, $R^{3B}$, $R^{4A}$, $R^{4B}$, $R^5$, $R^6$, $R^7$, $R^8$, $R^9$, $R^{10}$, $R^{11}$, $R^{12}$ or a combination thereof.

Encoded chromophoric polymer particles of the present disclosure can include a polymer that includes a narrow-band monomer having the structure of Formula (XXVIII):

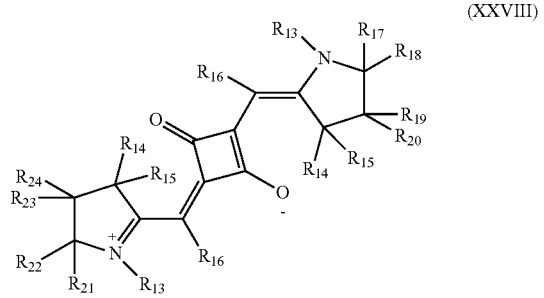

(XXVIII)

wherein each of $R^{13}$ is independently selected from the group consisting of, but not limited to, hydrogen, deuterium, alkyl and aryl; and $R^{14}$, $R^{15}$, $R^{16}$, $R^{17}$, $R^{18}$, $R^{19}$, $R^{20}$, $R^{21}$, $R^{22}$, $R^{23}$ and $R^{24}$ are independently selected from the group consisting of, but not limited to, hydrogen, deuterium, alkyl, aryl, cyano, amino, sulfide, aldehyde, ester, ether, acid, hydroxyl, and halide. The narrow-band monomer can be integrated into a backbone of the polymer (e.g. along the backbone of the polymer by polymerizing in the polymer) and/or attached by covalent attachment to the backbone, a terminus, or a sidechain of the polymer through at least one attachment to $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$ or a combination thereof.

In some aspects, the narrow-band emissive polymers for making encoded chromophoric polymer particles include metal complexes and their derivatives as narrow-band monomers. Metal complexes and their derivatives include but are not limited to their alkyl derivatives, aryl derivatives, alkyne derivatives, aromatic derivatives, alkoxide derivatives, aza derivatives, their extended systems and analogues. The narrow-band emissive polymers can also include any other monomers. The metals can be any metal such as Na, Li, Zn, Mg, Fe, Mn, Co, Ni, Cu, In, Si, Ga, Al, Pt, Pd, Ru, Rh, Re, Os, Ir, Ag, Au and so on. The metal complexes can be energy acceptors and other monomers can be energy donors so that the final chromophoric polymer particles can exhibit narrow-band emissions. The narrow-band emissive chromophoric polymers in good solvents may exhibit broad emissions or narrow emissions. However, in some aspects, their nanoparticle form gives narrow-band emissions. In some aspects, the emission FWHM of the above chromophoric polymer particles is less than 70 nm. In certain aspects, the FWHM is less than 60 nm, less than 50 nm, less than 40 nm, less than 30 nm, or less than 20 nm. Metal complexes and metal complex derivatives can be polymerized to form polymers (e.g., homopolymers or heteropolymers) and/or can be attached (e.g., covalently attached) to a polymer backbone, sidechain and/or terminus.

In some aspects, the narrow-band emissive polymers for making encoded chromophoric polymer particles include porphyrin, metalloporphyrin, and their derivatives as narrow-band monomers. Porphyrin, metalloporphyrin, and their derivatives can be polymerized to form polymers (e.g., homopolymers or heteropolymers) and/or can be attached (e.g., covalently attached) to a polymer backbone, sidechain and/or terminus. Porphyrin, metalloporphyrin, and their derivatives include but are not limited to their alkyl derivatives, aryl derivatives, alkyne derivatives, aromatic derivatives, alkoxide derivatives, aza derivatives, their extended systems and analogues. The metals in the metalloporphyrins can be any metal such as Na, Li, Zn, Mg, Fe, Mn, Co, Ni, Cu, In, Si, Ga, Al, Pt, Pd, Ru, Rh, Re, Os, Ir, Ag, Au and so on. The narrow-band emissive polymers can also include any other monomers. The porphyrin, metalloporphyrin and their derivatives can be energy acceptors and other monomers can be energy donors so that the final chromophoric polymer particles can exhibit narrow-band emissions. The narrow-band emissive chromophoric polymers in good solvents may exhibit broad emissions or narrow emissions. However, in some aspects, their nanoparticle form gives narrow-band emissions. In some aspects, the emission FWHM of the above chromophoric polymer particles is less than 70 nm. In certain aspects, the FWHM is less than 60 nm, less than 50 nm, less than 40 nm, less than 30 nm, or less than 20 nm.

In some aspects, the narrow-band emissive polymers for making chromophoric polymer particles include phthalocyanine and its derivatives as monomers. Phthalocyanine and its derivatives as monomers can be polymerized to form polymers (e.g., homopolymers or heteropolymers) and/or can be attached (e.g., covalently attached) to a polymer backbone, sidechain and/or terminus. Phthalocyanine derivatives include but are not limited to their alkyl derivatives, aryl derivatives, alkyne derivatives, aromatic derivatives, alkoxide derivatives, aza derivatives, their extended systems and analogues. The metals in the phthalocyanine derivatives can be any metal such as Na, Li, Zn, Mg, Fe, Mn, Co, Ni, Cu, In, Si, Ga, Al, Pt, Ru, Rh, Re, Os, Ir, Ag, Au or Pd. The narrow-band emissive polymers can also include any other monomers. The phthalocyanine derivatives can be energy acceptors so that the final chromophoric polymer particles can exhibit narrow-band emissions. The narrow-band emissive chromophoric polymers in good solvents may exhibit broad emissions or narrow emissions. However, in some aspects, their nanoparticle form gives narrow-band emissions. In some aspects, the emission FWHM of the above chromophoric polymer particles is less than 70 nm. In certain aspects, the FWHM is less than 60 nm, less than 50 nm, less than 40 nm, less than 30 nm, or less than 20 nm.

A wide variety of chromophoric polymer particles can be used for encoding, such as the examples described herein as well as others that are disclosed, e.g., in PCT/US2010/056079 and PCT/US2012/071767, each of which is incorporated by reference herein it its entirety and specifically with regard to the particular chromophoric polymer particle compositions and the respective methods of making them as described therein. As provided, e.g., in PCT/US2010/056079, the polymers in the chromophoric polymer particles can be physically blended or chemically bonded (or chemically crosslinked). For example, the physically blended polymer particles can include polymers that are blended in the chromophoric polymer particle and held together by non-covalent interactions. Chemically bonded chromophoric polymer particles can include polymers that are covalently attached to each other in the polymer particle. The chemically bonded polymers can be covalently attached to each other prior to formation of the polymer particles.

In some aspects, the encoded chromophoric polymer particle is a nanoparticle. In some aspects, the sizes of the nanoparticles provided herein are defined in terms of a "critical dimension," which refers to the smallest dimension of the nanoparticle. Many nanoparticles are roughly spherical in shape, which results in the critical dimension being the diameter of the spherical particle. While typical nanoparticles, such as nanospheres and nanocubes, are completely nanoscopic in size, not every dimension of a nanoparticle needs to be at the nanoscale. For example, a nano-cylinder may have a diameter on the nano-scale but a length on the micro-scale.

In some aspects, the typical size of an encoded chromophoric polymer particle is fewer than 100 nanometers. In certain aspects, most colloidal polymer nanoparticles are composed of a lyophobic polymer interior, but polyelectrolytes can also be forced to form nanoparticles. In certain aspects, the encoded chromophoric polymer particle comprises at least one chromophoric polymer and at least one other chromophore (e.g., lanthanide material) that have been formed into a stable particle. The particle size can vary from 5 nanometers to 500 nanometers. In some aspects, the critical dimension (e.g., diameter) of the particle is less than 500 nanometers. In some aspects, the critical dimension of the particle is less than 400 nanometers. In some aspects, the critical dimension of the particle is less than 300 nanometers. In some aspects, the critical dimension of the particle is less than 200 nanometers. In some aspects, the critical dimension of the particle is less than 100 nanometers. In some aspects, the critical dimension of the particle is less than 50 nanometers. In some aspects, the critical dimension of the particle is less than 40 nanometers. In some aspects, the critical dimension of the particle is less than 30 nanometers. In some aspects, the critical dimension of the particle is less than 20 nanometers. In some aspects, the critical dimension of the particle is less than 10 nanometers.

The possible shape of the nanoparticle is essentially unlimited. However, in certain aspects, the shape is selected from a sphere, a cylinder, an ellipsoid, a polyhedron, a prism, a rod, and a wire. The shape of the nanoparticle can contribute to the optical properties, as will be appreciated by those of skill in the art (e.g., nano-rods may have different optical properties than nano-spheres).

In some aspects, the nanoscale size of the nanoparticle is beneficial in order to bypass issues presented by large particle sizes. For example, when attaching nanoparticles to a target analyte molecule (e.g., a protein) for photoluminescence imaging, relatively large particles have more surface area available for non-specific binding to molecules other than the target analyte, or adsorption to a surface.

Lanthanide Compositions of Encoded Chromophoric Polymer Particles

In some aspects of the present disclosure, the encoded chromophoric polymer particles described herein include one or more lanthanide materials. The lanthanide materials can be lanthanide ions, lanthanide complexes, or lanthanide nanoparticles. In certain aspects, the lanthanide materials are lanthanide chromophores. In some aspects, the present disclosure utilizes the unique luminescent properties of lanthanide ions such as their narrow emission bandwidths, long lifetimes, and stable f-f transitions that are not easily influenced by the environment. Therefore, when integrating into conjugated polymer nanoparticles or other types of chromophoric polymer particles, lanthanide ions maintain their individual luminescence and their emission intensity can be independently or semi-independently tuned. Based on these unique properties, the present disclosure provides an improved encoding technology for high throughput bioanalysis.

In certain aspects, the lanthanide chromophores described herein have narrow emission properties, long luminescence lifetime, and distinct luminescence mechanisms as compared to organic fluorophores. For example, in a principle luminescence mechanism of lanthanide (III) ions (such as Ce (III), Pr(III), Nd(III), Pm(III), Sm(III), Eu(III), Gd(III), Tb(III), Dy(III), Ho(III), Er(III), Tm(III), or Yb(III)), whose 4f shells are not empty and not fully filled by electrons, transitions within the f shells can yield luminescence ranging from the UV region to near infrared region. In some aspects, because the inner shell f orbital electrons are shielded from the environment by the filled 5s5p sub-shells, their luminescence does not vary much with the environment. In some aspects, lanthanide ions exhibit Stokes luminescence, i.e., a short-wavelength photon excitation generates a long-wavelength photon emission. In certain aspects, one photon excitation can generate two or more photon emission (quantum cutting), e.g., the energy of one photon can be split to have two or more photon emission. In some aspects, lanthanide ions exhibit anti-Stokes luminescence (upconversion luminescence), e.g., two or more long-wavelength photons excitation generates a short-wavelength photon emission.

Various types of lanthanide chromophores are suitable for use with the present disclosure. A lanthanide chromophore can include any suitable type of lanthanide material, such as lanthanide ions, lanthanide complexes, lanthanide nanoparticles, or combinations thereof. In some aspects, a lanthanide chromophore includes a lanthanide selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), Lu(III), or a combination thereof. In some aspects, the lanthanide chromophores of the present disclosure are lanthanide derivatives, e.g., lanthanide derivatives selected from an alkyl derivative, aryl derivative, alkyne derivative, aromatic derivative, alkoxide derivative, aza derivative, an extended system thereof, or an analogue thereof. In certain aspects, the lanthanide chromophores are doped in an inorganic host material such as lanthanide oxide, lanthanide fluoride and related materials. The lanthanide ion can also coordinate with organic chromophores to form lanthanide chromophore complexes.

In some aspects, a lanthanide chromophore includes a rare earth metal selected from Sc, Y, La, Ce, Pr, Nd, Pm, Sm, Eu, Gd, Tb, Dy, Ho, Er, Tm, Yb, Lu, or a combination thereof. In certain aspects, the lanthanide chromophore includes a rare earth metal (e.g., a rare earth metal ion) that is used as a non-luminescent host material (e.g., Sc, Y, La, Gd, Lu, or a combination thereof) and one or more luminescent rare earth metal ions that are doped in the host (e.g., Eu(III), Tb(III), Ho(III), Er(III), Tm(III), Yb(III), or combinations thereof). In various aspects, the lanthanide chromophore includes at least one doped lanthanide ion that is preferable for downconversion luminescence, such as Pr(III), Sm(III), Eu(III), Tb(III), Dy(III), Yb(III), or a combination thereof. In various aspects, the lanthanide chromophore includes at least one doped lanthanide ion that is preferable for upconversion luminescence, such as Ho(III), Er(III), Tm(III), Yb(III), or a combination thereof. Any suitable number and combination of ions can be simultaneously doped into a single host material, such as two or more ions, three or more ions, four or more ions, five or more ions, six or more ions, seven or more ions, eight or more ions, nine or more ions, or ten or more ions.

In certain aspects, the encoded chromophoric polymer particles of the present disclosure can include at least one type of chromophoric polymer as described herein and at least one type of lanthanide chromophore, such as lanthanide ions, lanthanide complexes, or lanthanide nanoparticles. The optical properties of the chromophoric polymer and/or lanthanide chromophore can be varied as desired. In some aspects, the chromophoric polymer is fluorescent so that both the polymer fluorescence and lanthanide chromophore luminescence can be used for encoding. In some aspects, the chromophoric polymer is weakly fluorescent or significantly quenched so that only the lanthanide materials are used for encoding. In certain aspects, the peak emission wavelength of the lanthanide chromophore is longer than the peak emission wavelength of the chromophoric polymer. In other aspects, the peak emission wavelength of the lanthanide chromophore is shorter than the peak emission wavelength of the chromophoric polymer.

In some aspects, the encoded chromophoric polymer particle provides a flexible polymer matrix (e.g., formed from one or more chromophoric polymers) that can accommodate the lanthanide materials. Accordingly, in certain aspects, an encoded chromophoric polymer particle includes a polymer matrix and at least one lanthanide chromophore incorporated in the polymer matrix. Any suitable number and combination of lanthanide chromophore types can be incorporated in the polymer matrix, such at one or more lanthanide chromophores, two or more lanthanide chromophores, three or more lanthanide chromophores, four or more lanthanide chromophores, five or more lanthanide chromophores, six or more lanthanide chromophores, seven or more lanthanide chromophores, eight or more lanthanide chromophores, nine or more lanthanide chromophores, ten or more lanthanide chromophores, at fifty or more lanthanide chromophores, or one hundred or more lanthanide chromophores. The mass concentration of the lanthanide materials relative to the entire encoded chromophoric polymer particle mass can be varied from 1% to 99%, more preferably between 10% and 99%, more preferably between 20% and 99%, more preferably between 30% and 99%, more preferably between 40% and 99%, and more preferably between 50% and 99%.

In certain aspects, at least some of the lanthanide chromophores are distinct lanthanide chromophores (e.g., having different structures, compositions, and/or properties). For example, some or all of the lanthanide chromophores can have optical properties (e.g., emission spectra, emission wavelengths, emission intensities, emission lifetimes) that are distinguishable from one another. The concentrations of the lanthanide chromophores in the encoded chromophoric polymer particle can be varied as desired. In some aspects, the encoded chromophoric polymer particle comprises a first concentration of a first lanthanide chromophore and a second concentration of a second lanthanide chromophore. In certain aspects, the encoded chromophoric polymer particle comprises two or more lanthanide chromophores in a fixed ratio (e.g., fixed mass ratio) to each other.

In various aspects, the optical properties of the polymer matrix and one or more lanthanide chromophores incorporated in the polymer matrix are designed to generate the desired optical encoding for the chromophoric polymer particle. In some aspects, the optical properties (e.g., emission spectra) of the polymer matrix and the one or more lanthanide chromophores are distinguishable from one another. For example, in certain aspects, the emission peak(s) of the one or more lanthanide chromophores have longer wavelengths than the emission peak(s) of the polymer matrix. In other aspects, the emission peak(s) of the one or more lanthanide chromophores have shorter wavelengths than the emission peak(s) of the polymer matrix. In various aspects, the intensities of the emission peaks of the one or more lanthanide chromophores and the polymer matrix are independently or semi-independently controllable. In certain aspects, there is energy transfer between the polymer matrix and the one or more lanthanide chromophores. In alternative aspects, there is substantially no energy transfer between the polymer matrix and the one or more lanthanide chromophores.

In some aspects, the lanthanide chromophore incorporated in the polymer matrix is physically embedded or integrated into the polymer matrix. In some aspects, the lanthanide chromophore is chemically crosslinked and/or physically blended with the polymer matrix. In some aspects, a first lanthanide chromophore is crosslinked to the polymer matrix at a first concentration and a second lanthanide chromophore is crosslinked to the polymer matrix at a second concentration that is different from the first concentration. In some aspects, a first lanthanide chromophore is physically blended with the polymer matrix at a first concentration and a second lanthanide chromophore is physically blended with the polymer matrix at a second concentration that is different from the first concentration.

In some aspects, the encoded chromophoric polymer particles include at least one type of chromophoric polymer physically blended or chemically cross-linked with a lanthanide chromophore, such as luminescent lanthanide complexes. Exemplary luminescent lanthanide (III) complexes include La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) complexes. Because the majority of lanthanide complexes show luminescence from f-f transitions sensitized by the organic ligands, energy transfer from the chromophoric polymer to the lanthanide complexes can be controlled by varying the structure and/or composition of the polymer and/or the lanthanide complexes. In some aspects, the energy transfer from the polymers to the lanthanide complexes can be prevented or minimized. In some aspects, the energy transfer from the polymer to the lanthanide complexes can be allowed. The optical properties (e.g., emission intensities, emission wavelengths, emission lifetimes) of each set of emission peaks of the particle can be tuned and adjusted independently or semi-independently.

In some aspects, the encoded chromophoric polymer particle includes one type of chromophoric polymer physically blended or chemically cross-linked with at least one type of luminescent lanthanide complex such as terbium (Tb) complexes. In some aspects, the Tb complexes generally show bright green luminescence. The energy transfer from the chromophoric polymers to the Tb complexes can be controlled by varying the structure and/or composition of the polymers and/or the Tb complexes. In some aspects, the energy transfer from the polymers to the Tb complexes is prevented or minimized. In some aspects, the energy transfer from the polymers to the Tb complexes is allowed. Therefore the optical properties (e.g., emission intensities, emission wavelengths, emission lifetimes) of the Tb and the chromophoric polymer inside the particle can be tuned and adjusted independently or semi-independently.

In some aspects, the encoded chromophoric polymer particle includes at least one type of chromophoric polymer physically blended or chemically cross-linked with one type of luminescent lanthanide complex such as europium (Eu) complexes. In some aspects, the Eu complexes generally show bright red luminescence. The energy transfer from chromophoric polymers to the Eu complexes can be controlled by varying the structure and/or composition of the polymer and/or the Eu complexes. In some aspects, the energy transfer from the polymer to the Eu complexes is prevented or minimized. In some aspects, the energy transfer from the polymer to the Eu complexes is allowed. Therefore the optical properties (e.g., emission intensities, emission wavelengths, emission lifetimes) of the Eu and the chromophoric polymer inside the particle can be tuned and adjusted independently or semi-independently.

FIG. 1 shows a schematic for designing encoded chromophoric polymer particles that include at least one type of conjugated polymer and at least one type of lanthanide species. The lanthanide species can be lanthanide complexes, lanthanide ions, or lanthanide nanoparticles. The star represents one type of lanthanide species selected from La(III), Ce(III), Pr(III), Nd(III), Pm(III), Sm(III), Sm(II) Eu(III), Eu(II), Gd(III), Tb(III), Dy(III), Ho(III), Er(III), Tm(III), Yb(III), Yb(II), or Lu(III) species. In some aspects, the conjugated polymer is a chromophoric polymer. The lanthanide species can be physically blended or chemically cross-linked with the conjugated polymers in the encoded chromophoric polymer particles. The structures and/or the compositions of the encoded chromophoric polymer particles can be adjusted and varied to tune the optical properties (e.g., emission intensities, emission wavelengths, emission lifetimes) of the conjugated polymer and the lanthanide species. The optical properties (e.g., emission intensities, emission wavelengths, emission lifetimes) of each set of emission peaks of the particle can be tuned and adjusted independently or semi-independently. The mass concentration of the lanthanide materials relative to the entire polymer nanoparticle mass can be varied from 1% to 99%; more preferably between 10% and 99%, more preferably between 20% and 99%, more preferably between 30% and 99%, more preferably between 40% and 99%, and more preferably between 50% and 99%.

In some aspects, the encoded chromophoric polymer particle includes at least one type of chromophoric polymer physically blended or chemically cross-linked with at least two types of lanthanide complex which are selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) complexes. The energy transfer from chromophoric polymers to the lanthanide complexes can be controlled by varying the structure and/or composition of the polymer and/or the lanthanide complexes. In some aspects, the energy transfer from the polymer to the lanthanide complexes is prevented or minimized. In some aspects, the energy transfer from the polymer to the lanthanide complexes is allowed. Therefore the optical properties (e.g., emission intensities, emission wavelengths, emission lifetimes) of the lanthanide complexes and the chromophoric polymer inside the particles can be tuned and adjusted independently or semi-independently.

In some aspects, the encoded chromophoric polymer particle includes at least one type of chromophoric polymer physically blended or chemically cross-linked with at least two types of lanthanide complex such as Tb and Eu complexes. The energy transfer from chromophoric polymers to the lanthanide complexes can be controlled by varying the structure and/or composition of the polymer and/or the lanthanide complexes. In some aspects, the energy transfer from the polymer to the lanthanide complexes is prevented or minimized. In some aspects, the energy transfer from the polymer to the lanthanide complexes is allowed. Therefore the optical properties (e.g., emission intensities, emission wavelengths, emission lifetimes) of the Tb, the Eu, and the chromophoric polymer inside the particles can be tuned and adjusted independently or semi-independently.

Figure 2:
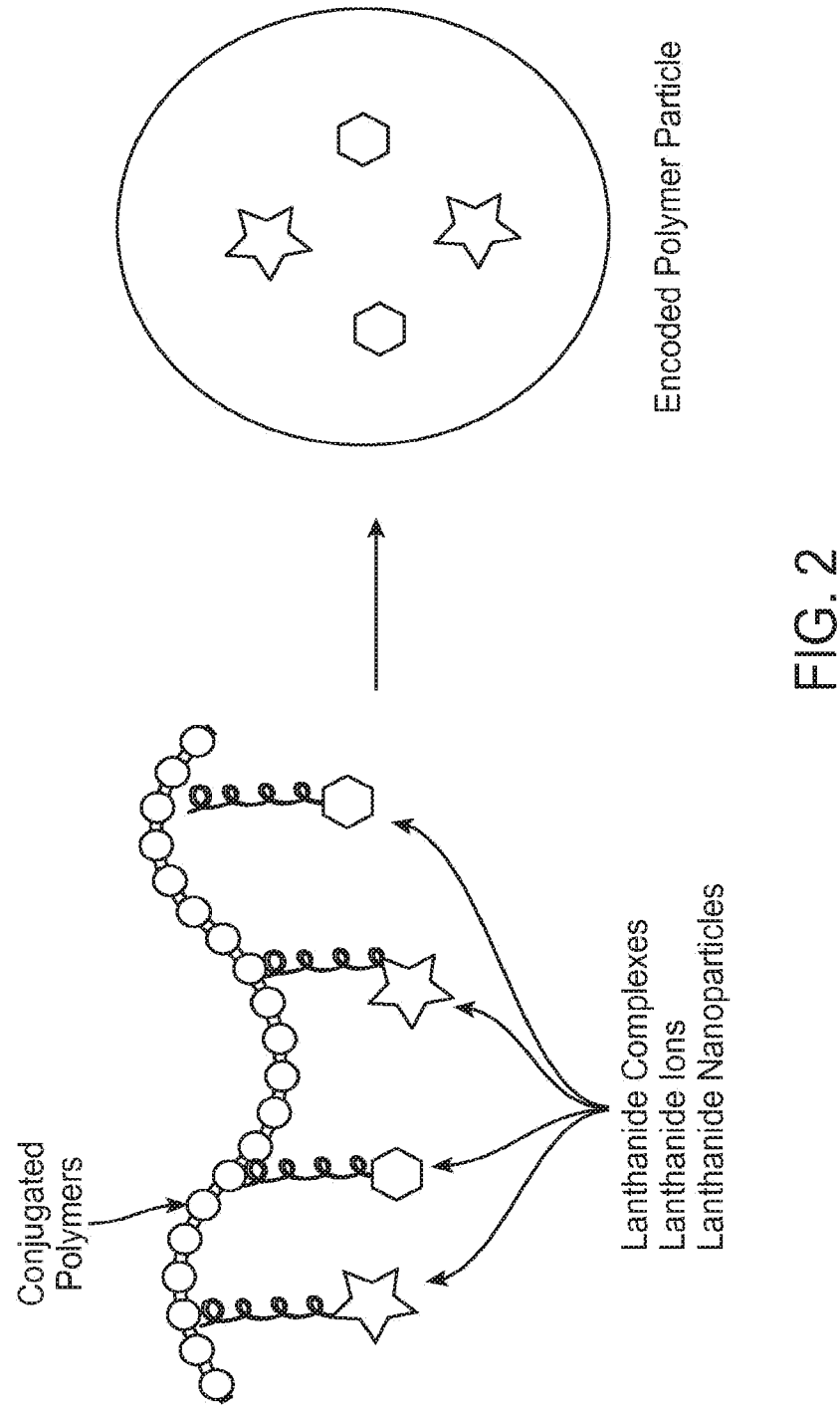
FIG. 2 depicts a schematic for designing encoded chromophoric polymer particles that include at least one type of conjugated polymer and at least two types of lanthanide species.

FIG. 2 shows the schematics for designing encoded chromophoric polymer particles that include at least one type of conjugated polymer and at least two types of lanthanide species. The lanthanide species can be lanthanide complexes, lanthanide ions, or lanthanide nanoparticles. The star and hexagon represent different lanthanide species selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) species. The lanthanide species can be physically blended or chemically cross-linked with the conjugated polymers in the encoded chromophoric polymer particles. The structures and/or the compositions of the encoded chromophoric polymer particles can be adjusted and varied to tune the optical properties (e.g., emission intensities, emission wavelengths, emission lifetimes) of the conjugated polymer and each lanthanide species. The optical properties (e.g., emission intensities, emission wavelengths, emission lifetimes) of each set of emission peaks of the particle can be tuned and adjusted independently or semi-independently. The mass concentration of the lanthanide materials relative to the entire polymer nanoparticle mass can be varied from 1% to 99%; more preferably between 10% and 99%, more preferably between 20% and 99%, more preferably between 30% and 99%, more preferably between 40% and 99%, and more preferably between 50% and 99%.

In some aspects, the encoded chromophoric polymer particle includes at least one type of chromophoric polymer physically blended or chemically cross-linked with at least three types of lanthanide complexes which are selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) complexes. The energy transfer from chromophoric polymers to the lanthanide complexes can be controlled by varying the structure and/or composition of the polymer and/or the lanthanide complexes. In some aspects, the energy transfer from the polymer to the lanthanide complexes is prevented or minimized. In some aspects, the energy transfer from the polymer to the lanthanide complexes is allowed. Therefore the optical properties (e.g., emission intensities, emission wavelengths, emission lifetimes) of each species inside the particle can be tuned and adjusted independently or semi-independently.

Figure 3:
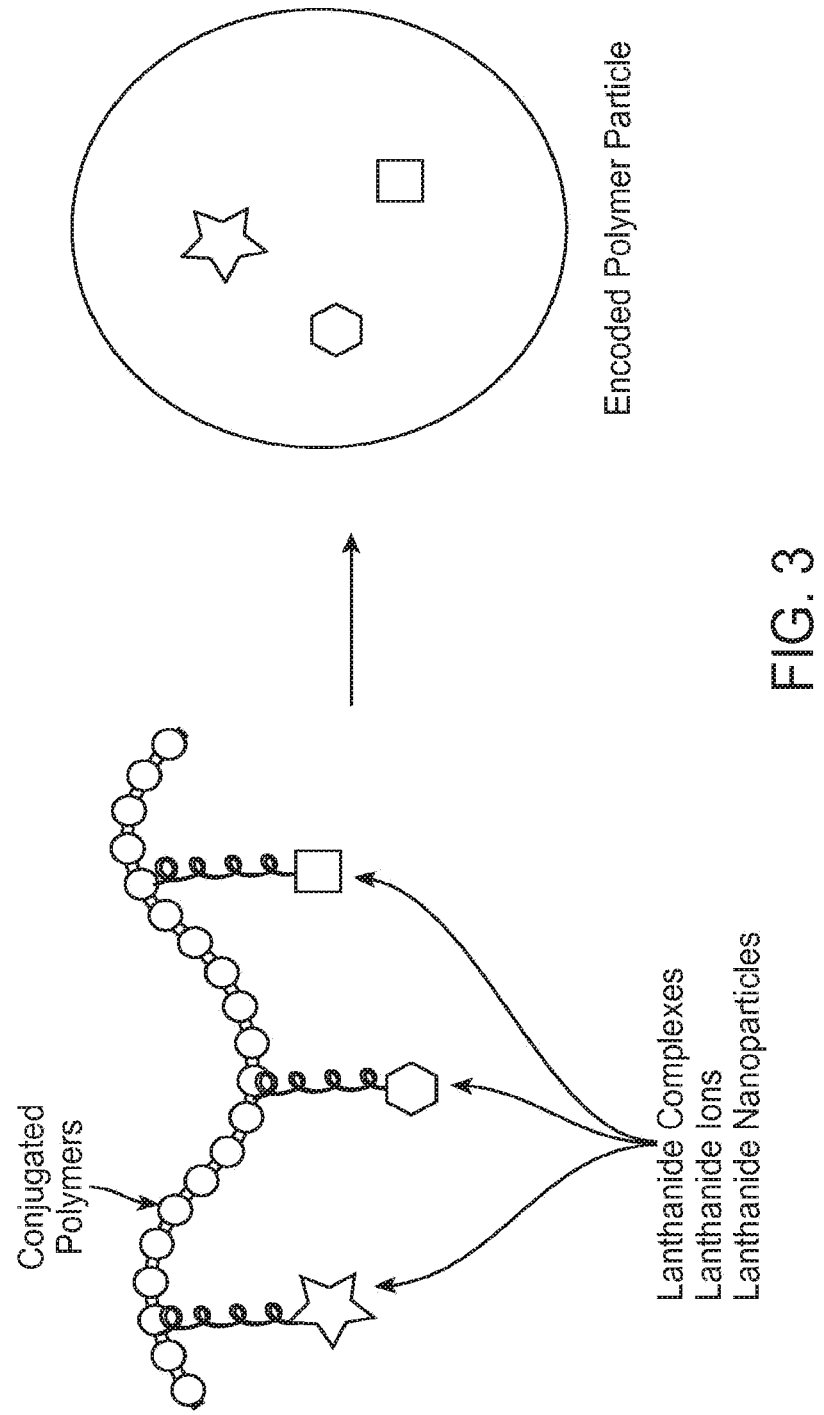
FIG. 3 depicts a schematic for designing encoded chromophoric polymer particles that include at least one type of conjugated polymer and at least three types of lanthanide species.

FIG. 3 shows the schematics for designing encoded chromophoric polymer particles that include at least one type of conjugated polymer and at least three types of lanthanide species. The lanthanide species can be lanthanide complexes, lanthanide ions, or lanthanide nanoparticles. The star, hexagon, and square represent different lanthanide species selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) species. The lanthanide species can be physically blended or chemically cross-linked with the conjugated polymers in the encoded chromophoric polymer particles. The structures and/or the compositions of the encoded chromophoric polymer particles can be adjusted and varied to tune the optical properties (e.g., emission intensities, emission wavelengths, emission lifetimes) of the conjugated polymer and each lanthanide species. The optical properties (e.g., emission intensities, emission wavelengths, emission lifetimes) of each set of emission peaks of the particle can be tuned and adjusted independently or semi-independently. The mass concentration of the lanthanide materials relative to the entire polymer nanoparticle mass can be varied from 1% to 99%; more preferably between 10% and 99%, more preferably between 20% and 99%, more preferably between 30% and 99%, more preferably between 40% and 99%, and more preferably between 50% and 99%.

In some aspects, the chromophoric polymer particle includes at least one type of chromophoric polymer physically blended or chemically cross-linked with at least four types of lanthanide complexes which are selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) complexes. The energy transfer from chromophoric polymers to the lanthanide complexes can be controlled by varying the structure and/or composition of the polymer and/or the lanthanide complexes. In some aspects, the energy transfer from the polymer to the lanthanide complexes is prevented or minimized. In some aspects, the energy transfer from the polymer to the lanthanide complexes is allowed. Therefore the optical properties (e.g., emission intensities, emission wavelengths, emission lifetimes) of each species inside the particle can be tuned and adjusted independently or semi-independently.

Figure 4:
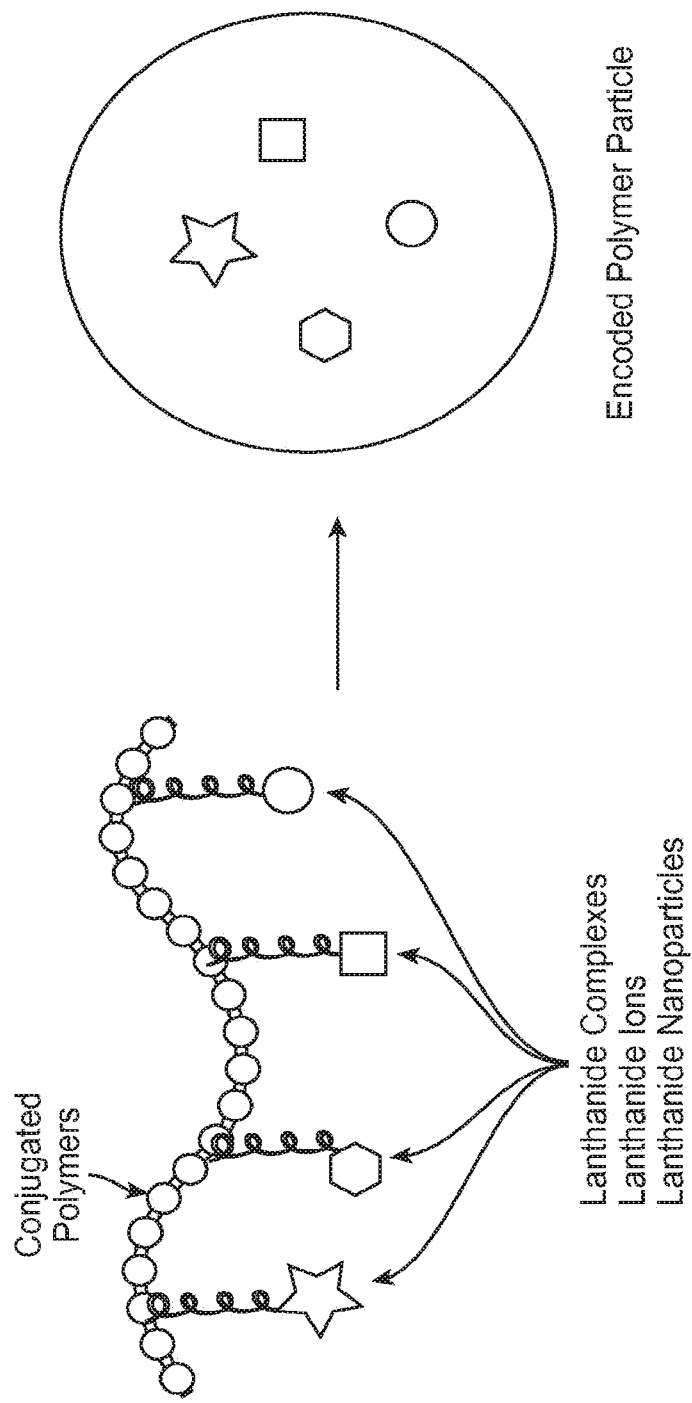
FIG. 4 depicts a schematic for designing encoded chromophoric polymer particles that include at least one type of conjugated polymer and at least four types of lanthanide species.

FIG. 4 shows the schematics for designing encoded chromophoric polymer particles that include at least one type of conjugated polymer and at least four types of lanthanide species. The lanthanide species can be lanthanide complexes, lanthanide ions, or lanthanide nanoparticles. The star, hexagon, square, and circle represent different lanthanide species selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) species. The lanthanide species can be physically blended or chemically cross-linked with the conjugated polymers in the encoded chromophoric polymer particles. The structures and/or the compositions of the encoded chromophoric polymer particles can be adjusted and varied to tune the optical properties (e.g., emission intensities, emission wavelengths, emission lifetimes) of the conjugated polymer and each lanthanide species. The optical properties (e.g., emission intensities, emission wavelengths, emission lifetimes) of each set of emission peaks of the particle can be tuned and adjusted independently or semi-independently. The mass concentration of the lanthanide materials relative to the entire polymer nanoparticle mass can be varied from 1% to 99%; more preferably between 10% and 99%, more preferably between 20% and 99%, more preferably between 30% and 99%, more preferably between 40% and 99%, and more preferably between 50% and 99%.

In some aspects, the chromophoric polymer particle includes at least one type of chromophoric polymer physically blended or chemically cross-linked with five or more types of lanthanide complexes which are selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) complexes. The energy transfer from chromophoric polymers to the lanthanide complexes can be controlled by varying the structure and/or composition of the polymer and/or the lanthanide complexes. In some aspects, the energy transfer from the polymer to the lanthanide complexes is prevented or minimize. In some aspects, the energy transfer from the polymer to the lanthanide complexes is allowed. Therefore the optical properties (e.g., emission intensities, emission wavelengths, emission lifetimes) of each species inside the particle can be tuned and adjusted independently or semi-independently.

In some aspects, the encoded chromophoric polymer particle includes at least one type of chromophoric polymer that is associated with lanthanide ions selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) ions. The lanthanide ions can coordinate with the backbone, side chains, or terminal groups of the chromophoric polymer. The resulting encoded chromophoric polymer particles therefore include the luminescent ions. In some aspects, the encoded particles include one type of lanthanide ions. In some aspects, the encoded particles include two types of lanthanide ions. In some aspects, the encoded particles include three types of lanthanide ions. In some aspects, the encoded particles include three types of lanthanide ions. In some aspects, the encoded particles include four types of lanthanide ions. In some aspects, the encoded particles include five types of lanthanide ions. In some aspects, the encoded particles include more than six types of lanthanide ions. The energy transfer from chromophoric polymers to the lanthanide ions can be controlled by varying the structure and composition of the polymer and the lanthanide ions. In some aspects, the energy transfer from the polymer to the lanthanide ions is prevented or minimized. In some aspects, the energy transfer from the polymer to the lanthanide ions is allowed. Therefore the optical properties (e.g., emission intensities, emission wavelengths, emission lifetimes) of each species inside the particle can be tuned and adjusted independently or semi-independently.

In some aspects, the chromophoric polymer particle includes at least one type of chromophoric polymer physically blended or chemically cross-linked with at least one type of lanthanide nanoparticles. In certain aspects, a lanthanide nanoparticle is a nanoparticle comprising one or more lanthanide chromophores. The lanthanide nanoparticles of the present disclosure can be lanthanide ion-doped inorganic nanoparticles such as oxides, fluorides, sulfides, aluminates, silicates, phosphates, molybdates, titanates, bismuthates, other metal salts, or a combination thereof. In some aspects, the lanthanide ion-doped inorganic nanoparticles comprise one or more metal salts.

In one aspect, the lanthanide nanoparticles are doped with one type of lanthanide ions selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) ions. In some aspects, the lanthanide nanoparticles are co-doped by two or more types of lanthanide ions, and therefore the resulting chromophoric polymer particles include two or more types of luminescent ions. The doped lanthanide ions can be any combinations selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) ions. The energy transfer from chromophoric polymers to the lanthanide nanoparticles can be controlled by varying the structure and composition of the polymer and the lanthanide nanoparticles. In some aspects, the energy transfer from the polymer to the lanthanide nanoparticles can be prevented or minimized. In some aspects, the energy transfer from the polymer to the lanthanide nanoparticles can be allowed. Therefore the optical properties (e.g., emission intensities, emission wavelengths, emission lifetimes) of each species inside the particle can be tuned and adjusted independently or semi-independently.

In some aspects, the encoded chromophoric polymer particle includes at least one type of chromophoric polymer physically blended or chemically cross-linked with at least one type of lanthanide upconversion nanoparticles. The lanthanide upconversion nanoparticles describe the nanoparticles that exhibit short-wavelength luminescence emissions by long-wavelength multiple-photon excitations. The lanthanide upconversion nanoparticles can be lanthanide ions doped inorganic nanoparticles such as oxides, fluorides, sulfides, aluminates, silicates, phosphates, molybdates, titanates, bismuthates, other metal salts, or a combination thereof. In certain aspects, the lanthanide upconversion nanoparticles are lanthanide-doped fluoride nanoparticles such as $NaYF_4$, $NaGdF_4$, $NaYbF_4$ or $NaLuF_4$ nanoparticles. In some aspects, the doped lanthanide ions for upconversion nanoparticle can be any combination selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) ions. In some aspects, the lanthanide upconversion nanoparticles are co-doped with Yb(III) and Er(III) ions. In some aspects, the lanthanide upconversion nanoparticles are co-doped with Yb(III) and Tm(III) ions. In some aspects, the lanthanide upconversion nanoparticles are co-doped with Yb(III) and Ho(III) ions. In some aspects, the lanthanide upconversion nanoparticles are co-doped with Yb(III) and Nd(III) ions. In some aspects, the lanthanide upconversion nanoparticles are co-doped with Yb(III) and Eu(III) ions. In some aspects, the lanthanide upconversion nanoparticles are co-doped with Yb(III) and Tb(III) ions. The energy transfer from chromophoric polymers to the lanthanide upconversion nanoparticles can be controlled by varying the structure and/or composition of the polymer and/or the lanthanide upconversion nanoparticles. In some aspects, the energy transfer from the polymer to the lanthanide upconversion nanoparticles can be prevented or minimized. In some aspects, the energy transfer from the polymer to the lanthanide upconversion nanoparticles is allowed. Therefore the optical properties (e.g., emission intensities, emission wavelengths, emission lifetimes) of each species inside the particle can be tuned and adjusted independently or semi-independently.

In some aspects, the lanthanide ion-doped inorganic nanoparticle comprises one or more compounds or molecules having the structure of Formula (XXIX):

$$(AM)\text{-}(RE)\text{-}(F_4) \quad\quad (XXIX)$$

wherein RE is a rare earth metal selected from Sc, Y, La, Ce, Pr, Nd, Pm, Sm, Eu, Gd, Tb, Dy, Ho, Er, Tm, Yb, Lu, or a combination thereof, and AM is an alkali metal selected from Li, Na, K, Rb, Cs, Fr, or a combination thereof. In certain aspects, RE is selected from Y, La, Eu, Gd, Ho, Tb, Er, Tm, Yb, Lu, or a combination thereof. In certain aspects, AM is selected from Li, Na, K, or a combination thereof. The compound of Formula (XXIX) can include two or more luminescent ions simultaneously doped into a non-luminescent host material (e.g., Sc, Y, Gd, Lu, or a combination thereof). In certain aspects, RE is a combination of different rare earth metal ions, such as two or more different rare earth metal ions, three or more different rare earth metal, four or more different rare earth metal ions, five or more different rare earth metal ions, six or more different rare earth metal ions, seven or more different rare earth metal ions, eight or more different rare earth metal ions, nine or more different rare earth metal ions, or ten or more different rare earth metal ions. An example of a compound having the structure of Formula (XXIX) is a Yb, Er-codoped $NaYF_4$ nanocrystal. The doping concentration of such compounds can be varied as desired (e.g., $Na(Y_{0.78}, Yb_{0.2}, Er_{0.02})F_4$. Another example of a compound having the structure of Formula (XXIX) is a Yb, Tm-codoped $NaYF_4$ nanocrystal. The doping concentration of such compounds can be varied as desired (e.g., $Na(Y_{0.79}, Yb_{0.2}, Em_{0.01})F_4$.

In some aspects, organic ligands are used as light-harvesting antennae in coordination with lanthanide ions. The energy absorbed by the organic ligand is first transferred from the singlet state to the triplet state (intersystem crossing) of the ligand, and then is transferred (or is directly transferred from the singlet state of the organic ligand) to the 4f excited states of the lanthanide ions by the resonant energy transfer process. In some aspects, lanthanide complexes that can be used with the present disclosure have the structure of Formula (XXX):

$$(L_1^-)_n\text{-}(LN^+)\text{-}(L_2)_m \quad\quad (XXX)$$

wherein $L_1$ is a first ligand, $L_2$ is a second ligand, LN is a lanthanide selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), Lu(III), or a combination thereof, n=0, 1, 2, 3 or more, and m=0, 1, 2, 3 or more.

In Formula (XXX), LN is a lanthanide ion (e.g., a lanthanide ion) that has an unfilled inner shell and can accept energy from the organic ligands or general polymers to give luminescence. Any suitable lanthanide can be used according to the present disclosure. In various aspects, LN can be selected without limitation from, e.g., La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III), and the like.

In Formula (XXX) above, $L_1$ and $L_2$ represent ligands that can be bound to $LN^+$. The ligands can be the same or different and each ligand can be present or absent (e.g., n, m=0, 1, 2 or 3 in Formula (XXX) above). Any suitable ligand can be used according to the present disclosure. In some aspects, each of $L_1$ and $L_2$ can independently be organic or inorganic ligands. In various aspects, there can be a plurality of ligands. For example, in some aspects there can be a plurality of ligand $L_1$ and/or a plurality of ligand $L_2$. In certain aspects, $L_1$ and $L_2$ are independently monodentate, bidentate, or polydentate ligands.

In some aspects, $L_1$ can be an anionic organic ligand coordinated with $LN^+$. In certain aspects, $L_1$ includes chelated O atoms, chelated N atoms, chelated S atoms, chelated P atoms, or a combination thereof. In some aspects, the anionic ligand $L_1$ of Formula (XXX) can be a halogen ion (e.g., $Cl^-$, etc.), $NO_3^-$, $SO_4^{2-}$, $CF_3SO_3^-$, and/or other inorganic radicals coordinated with $LN^+$. The total valences of $L_i$ and $LN^+$ can be equal to finally form a neutral lanthanide complex. $L_1$ can be monodentate, bidentate or polydentate and there can be one or more ligands $L_1$ in the lanthanide complex. In some aspects, $L_1$ is a bridged ligand and can be coordinated with $LN^+$ to form binuclear, trinuclear and polynuclear lanthanide complexes. Some of bridged $L_1$ can form cryptands and can be coordinated to $LN^+$ to synthesize lanthanide cryptate.

In some aspects, $L_1$ is selected from derivatives of: β-diketone, pyrazolone, isoxazolone, carboxylic acid, phthalocyanine, 8-hydroxyquinoline, pyrazol borate, porphyrin, a Schiff base, salicylaldehyde, phenylsalicylaldehyde, adenine, purine, 2-(2-hydroxyphenyl)benzothiadiazole, 2-(2-hydroxyphenyl)quinolone, 1-naphthol-2-carboxaldehyde, hydroxybenzophenone, 1,2-dihydroxybenzene, dihydroxynaphthalene, droxylfluorenone, 7-hydroxyinden-1-one, 7-hydroxy-3-phenylinden-1-one, 2-hydroxydimethylbenzene-1,3-diamide, 1,8-bis(4-methyl-2-hydroxybenzamido)-3,6-dioxaoctane, 2-hydroxy-N-methylbenzamide, bis (2-hydroxy-N-methylbenzamide), tri(2-hydroxy-N-methylbenzamide), 8-hydroxyquinazoline, 8-hydroxyquinoxaoline, hydroxybenzoxazole, hydroxy-2-phenyl benzoxazole, hypoxanthine, or a combination thereof.

Listed without limitation below are example chemical structures of organic anion ligands ($L_1$) to coordinate with lanthanide (III) ions and form lanthanide complexes.

In some aspects, the anionic ligand $L_1$ of Formula (XXX) can be a beta-diketone with the structure of Formula (XXXI):

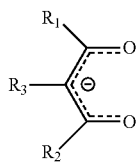

(XXXI)

In some aspects, the anionic ligand $L_1$ of Formula (XXX) can be a pyrazolone with the structure of Formula (XXXII):

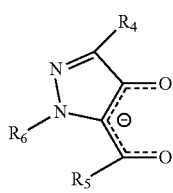

(XXXII)

In some aspects, the anionic ligand $L_1$ of Formula (XXX) can be an isoxazolone with the structure of Formula (XXXIII):

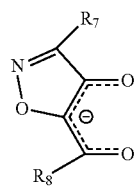

(XXXIII)

In some aspects, the anionic ligand $L_1$ of Formula (XXX) can be a carboxylic acid with the structure of Formula (XXXIV):

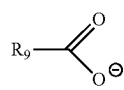

(XXXIV)

In some aspects, the anionic ligand $L_1$ of Formula (XXX) can be a phthalocyanine with the structure of Formula (XXXV):

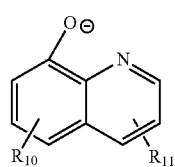

(XXXV)

In some aspects, the anionic ligand $L_1$ of Formula (I) can be an 8-hydroxyquinoline with the structure of Formula (XXXVI):

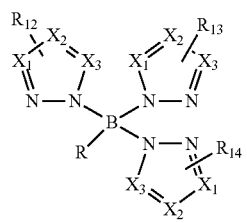

(XXXVI)

$R = C_nH_{2n+1}(n = 0\text{-}6)$,
$C_nH_{2n+1}(n = 0\text{-}6)$,
phenyl;
$X_1, X_2$ and $X_3 = O, N, S$ In some aspects, the anionic ligand $L_1$ of Formula (XXX) can be a porphyrin with the structure of Formula (XXXVII):

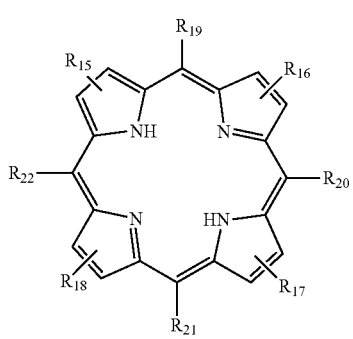

(XXXVII)

In some aspects, the anionic ligand $L_1$ of Formula (XXX) can be other macrocyclic ligands.

In some aspects, $L_2$ can be a neutral ligand coordinates with $LN^+$. In certain aspects, $L_1$ includes chelated O atoms, chelated N atoms, chelated S atoms, chelated P atoms, or a combination thereof. There can be a plurality of ligands $L_2$. $L_2$ can be the same or different. $L_2$ can be monodentate, bidentate or polydentate and there can be one or more ligands $L_2$ in the lanthanide complex. In some aspects, $L_2$ can be a bridged ligand and be coordinated with $LN^+$ to form binuclear, trinuclear and polynuclear lanthanide complexes. In some aspects, $L_2$ can be a cryptand. Some of bridged $L_2$ can form cryptands and can be coordinated to $LN^+$ to synthesize lanthanide cryptate.

In some aspects, $L_2$ is selected from substituted or unsubstituted pyridine, substituted or unsubstituted bipyridine, substituted or unsubstituted tripyridine, substituted or unsubstituted 1,10-phenanthroline, substituted or unsubstituted phosphine oxide, substituted or unsubstituted bi-(phosphine oxide), substituted or unsubstituted tri-(phosphine oxide), substituted or unsubstituted 4-(4,6-di(1H-pyrazol-1-yl)-1,3,5-triazin-2-yl)-N,N'-dimethylbenzenamine, or a combination thereof.

Listed without limitation below are example chemical structures of neutral ligands ($L_2$) to form lanthanide complexes.

In some aspects, the neutral ligand $L_2$ of Formula (XXX) can be a pyridine with the structure of Formula (XXXVIII):

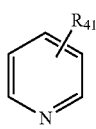

(XXXVIII)

In some aspects, the neutral ligand $L_2$ of Formula (I) can be a bipyridine with the structure of Formula (XXXIX):

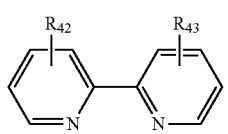

(XXXIX)

In some aspects, the neutral ligand $L_2$ of Formula (XXX) can be a tripyridine with the following Formula (XL):

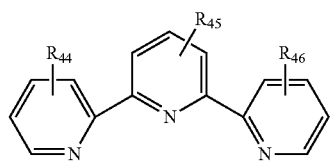

(XL)

In some aspects, the neutral ligand $L_2$ of Formula (XXX) can be a 1,10-phenanthroline with the following Formula (XLI):

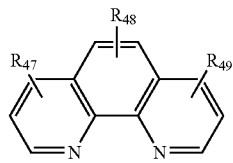

(XLI)

In some aspects, the neutral ligand $L_2$ of Formula (XXX) can be a 1,10-phenanthroline based derivative containing N atoms which can coordinate with lanthanide(III) metal ions.

In some aspects, the neutral ligand $L_2$ of Formula (XXX) can be a 4-(4,6-di(1H-pyrazol-1-yl)-1,3,5-triazin-2-yl)-N,N-dimethylbenzenamine with the following Formula (XLII):

(XLII)

In some aspects, the neutral ligand $L_2$ of Formula (XXX) can be a phosphine oxide with the following Formula (XLIII):

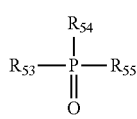

(XLIII)

In some aspects, the neutral ligand $L_2$ of Formula (XXX) can be a bi-(phosphine oxide) with the following Formula (XLIV):

(XLIV)

In some aspects, the neutral ligand $L_2$ of Formula (XXX) can be a tri-(phosphine oxide) with the following Formula (XLV):

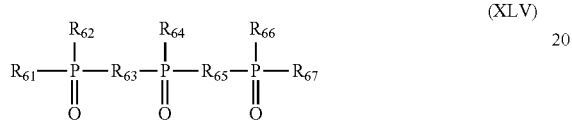
(XLV)

In some aspects, lanthanide complexes that can be used with the present disclosure can be described with the following Formula (XLVI):

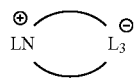
(XLVI)

In Formula (XLVI), LN is a lanthanide ion that has an unfilled inner shell and can accept energy from the organic ligands or general polymers to give luminescence. Any suitable lanthanide can be used according to the present disclosure. In various aspects, LN can be selected without limitation from, e.g., La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), Lu(III) and the like, or a combination thereof.

In Formula (XLVI) above, $L_3$ represents ligands that can be bound to LN. Any suitable ligand can be used according to the present disclosure. In some aspects, $L_3$ can be an organic or an inorganic ligand. In various aspects, there can be a plurality of ligands. For example, in some aspects there can be a plurality of ligand $L_3$. In some aspects, $L_3$ is a macrocyclic ligand.

In some aspects, $L_3$ is a neutral ligand. In other aspects, $L_3$ is an anionic ligand. In certain aspects of ligand $L_3$, in addition to acting as an anionic ligand like $L_1$, it can include additional groups to act as a neutral ligand like $L_2$ to be coordinated with LN. $L_3$ can act as an anion ligand and as a neutral ligand. There can be a plurality of ligands $L_3$. $L_3$ can be the same or different. $L_3$ can be monodentate, bidentate, or polydentate and there can be one or more ligands $L_3$ in the lanthanide complex.

Listed without limitation below are example chemical structures of anion-neutral ligands ($L_3$) to form lanthanide complexes. The anion-neutral ligands contain anion groups and some atoms to coordinate with lanthanide ions as neutral ligands.

In some aspects, the anion-neutral ligand $L_3$ of Formula (XLVI) can be a 1,4,7,10-tetraazacyclododecane ring based derivative with the structure of Formula (XLVII):

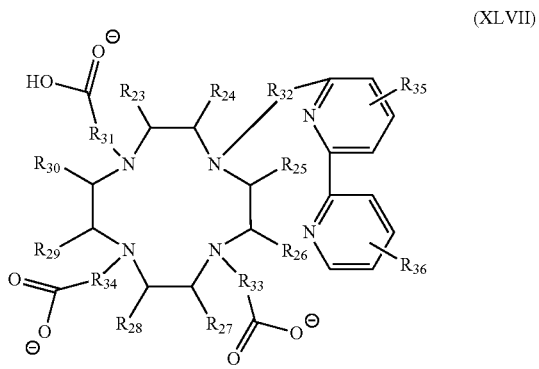
(XLVII)

In some aspects, the anion-neutral ligand $L_3$ of Formula (XLVI) can have the structure of the following Formula (XLVIII):

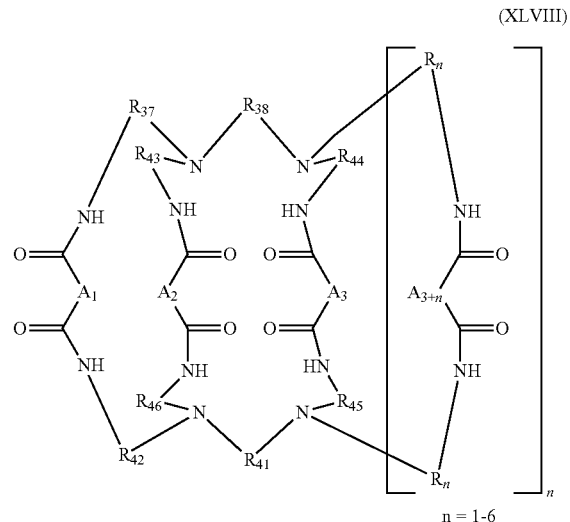
(XLVIII)

n = 1-6

$A_1, A_2, A_3$ and $A_4$ =

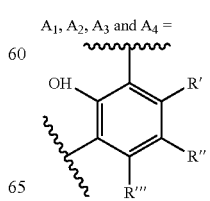

In some aspects, the structure presented in Formula (XLVI) has n=1 as in the following Formula (XLIX):
(XLIX)
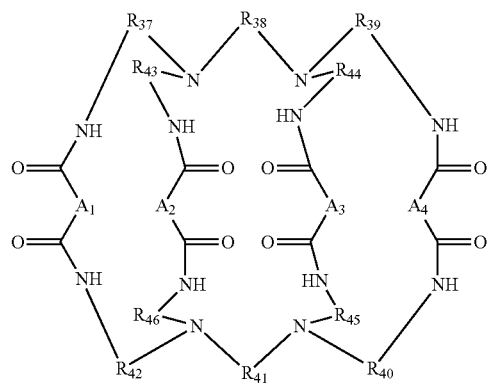
In some aspects, the structure presented in Formula (XLVI) has n=2 as in the following Formula (L):
(L)
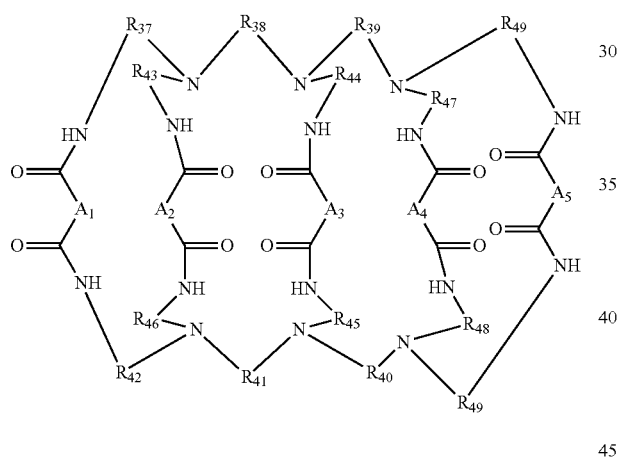
Compounds 1-48 below are exemplary substituents for use as groups $R_1$-$R_{49}$ in Formulae (XXX)-(L) above:
1
$C_nH_{2n+1}$;
2
$C_nF_{2n+1}$;
3
;
4
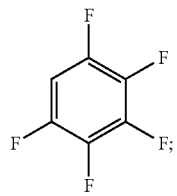
5
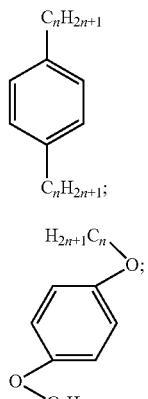
6
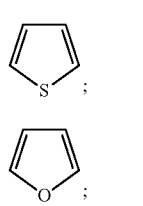
7
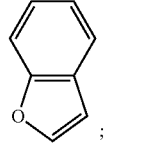
;
8
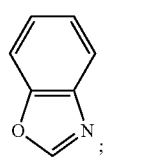
;
9
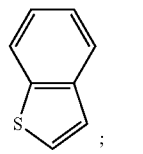
;
10
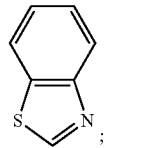
;
11
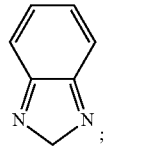
;
12
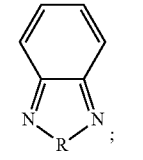
;
13
14-17
;
R = O, 14; S, 15; Se, 16; Te, 17;

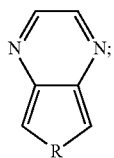
R = O, 18; S, 19; Se, 20; Te, 21;
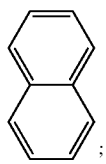
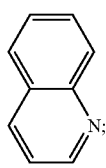
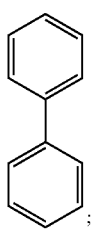
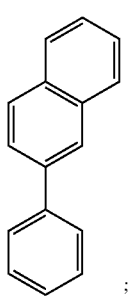
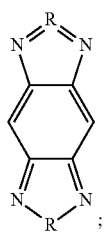
R = O, 26; S, 27; Se, 28; Te, 29;
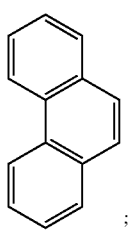
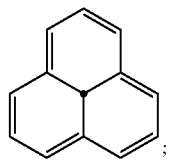
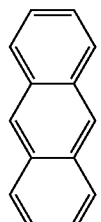
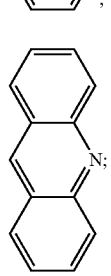
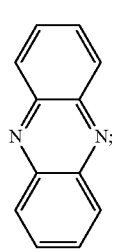
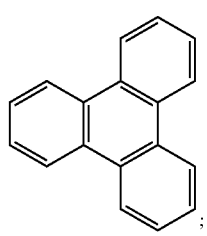
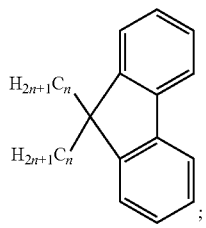
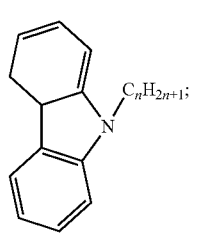

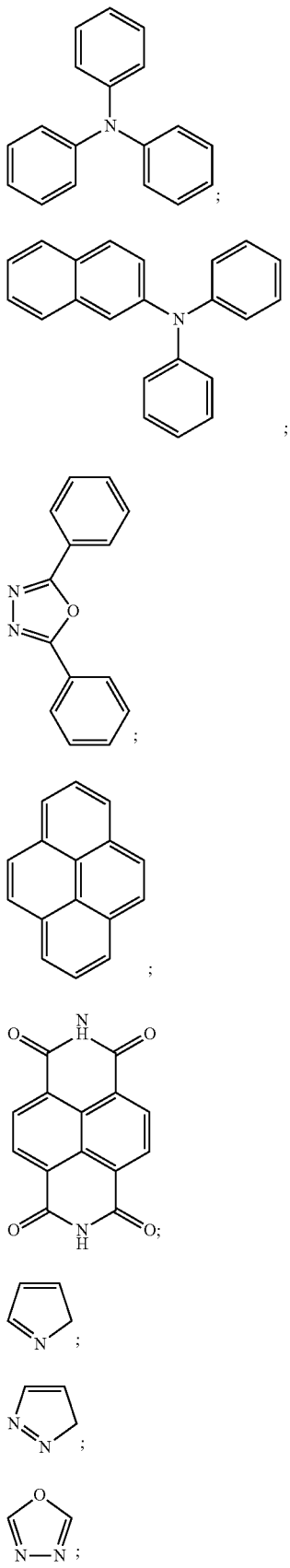

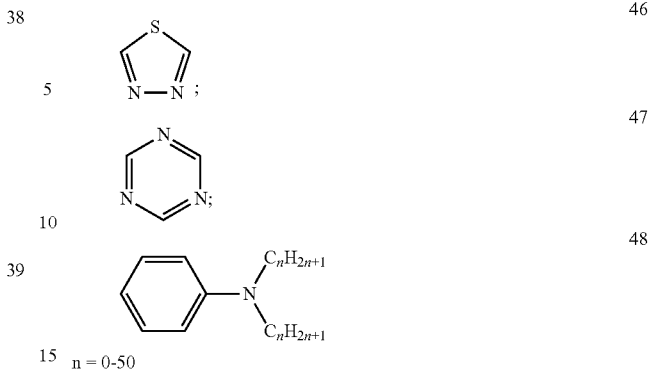

n = 0-50

In some aspects, each of the substituted groups $R_1$-$R_{49}$ depicted in Formulae (XXX)-(L) are independently selected from but not limited to: hydrogen (H), deuterium (D), halogen, direct or branched alkyl, fluorinated direct or branched alkyl, aromatic ring, and fluorinated aromatic ring. The fluorinated alkyl and aromatic ring groups can be selected from alkyl, alkoxy, aryl, alkyl ketone, alkylester, arylester, amide, fluoroalkyl, fluoroaryl, and polyalkalene (e.g., mehtoxyethoxyethoxy, ethoxyethoxy, and —$(OCH_2CH_2)_n$OH, n=1-50), phenyl, alkyl-(alkoxy-, aryl-, fluoroalkyl-, fluoroaryl-) substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-) substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary aspects, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9, 9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl.

Figure 5:
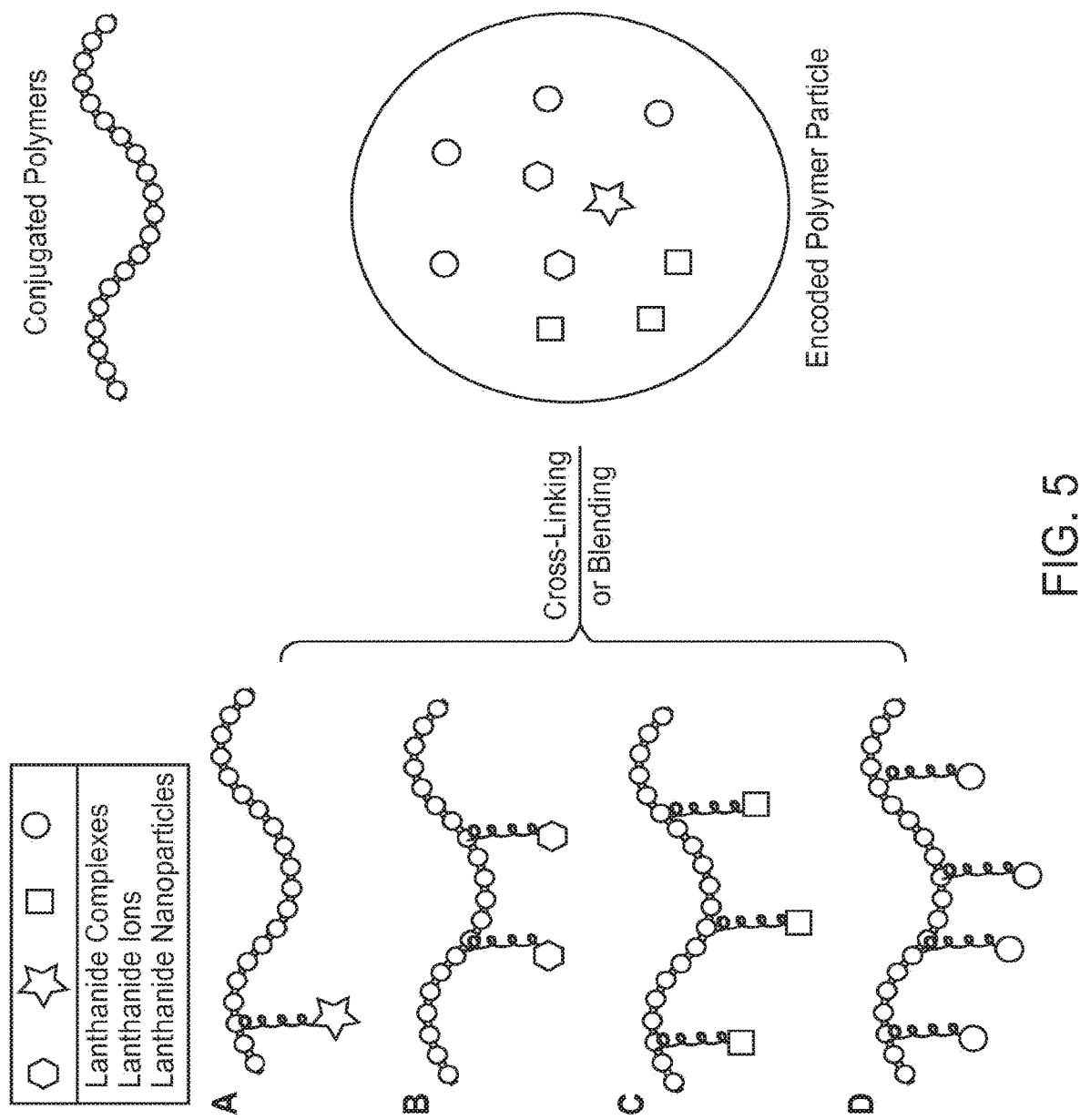
FIG. 5 depicts a schematic for preparing encoded chromophoric polymer particles from polymers with monodispersed chain length and a defined number of lanthanide species in the polymer side chains.

In some aspects, the present disclosure provides strategies to overcome Poisson statistics of fluorophore distribution in preparing the encoded chromophoric polymer particles. In one aspect, the encoded chromophoric polymer particles can be prepared from polymers with monodispersed chain length and defined number of lanthanide species in the polymer side chains. FIG. 5 shows a schematic for preparing encoded chromophoric polymer particles from polymers with monodispersed chain length and defined number of lanthanide species in the polymer side chains. In this strategy, for example, A, B, C, and D represent conjugated polymers with different types of lanthanide species. These polymers can be chemically cross-linked or physically blended to form the encoded chromophoric polymer particles. The lanthanide species can be lanthanide complexes, lanthanide ions, or lanthanide nanoparticles. The star, hexagon, square, and circle represent different lanthanide species selected from La(III), Ce(III), Pr(III), Nd(III), Pm(III), Sm(III), Sm(II) Eu(III), Eu(II), Gd(III), Tb(III), Dy(III), Ho(III), Er(III), Tm(III), Yb(III), or Yb(II) species. The structures and/or the compositions of the encoded chromophoric polymer particles can be adjusted and varied to tune the emission intensities of the conjugated polymer and each lanthanide species.

In some aspects, the encoded chromophoric polymer particles can be produced using a linear polymer, a branched polymer, or a dendrimer having a predefined and controlled number of chromophores per polymer (e.g., lanthanide complexes and/or chromophoric dyes). In certain aspects, the linear polymer, branched polymer, or dendrimer includes only a single end functional group that is used to control the fixed mass ratio between the various chromophores. The linear polymer, branched polymer, or dendrimer can comprise any suitable number and combination of chromophores (e.g., lanthanide chromophores) in a fixed mass ratio to each other, such as one or more chromophores, two or more chromophores, three or more chromophores, four or more chromophores, five or more chromophores, six or more chromophores, seven or more chromophores, eight or more chromophores, nine or more chromophores, or more chromophores.

In certain aspects, the conjugated polymer can be a dendrimer with a predefined and controlled number of chain terminus functional groups that are attached with chromophores, e.g., lanthanide complexes and/or chromophoric dyes. By adjusting the branched chains, the ratio (e.g., fixed mass ratio) of chromophore relative to the conjugated polymer can be controlled to form the encoded chromophoric polymer particles. For example, in some aspects, the encoded chromophoric polymer particles can be made from one type of conjugated polymer and lanthanide complex dendrimers. A lanthanide complex dendrimer can comprise any suitable number and combination of lanthanide chromophores in a fixed mass ratio to each other, such as one or more lanthanide chromophores, two or more lanthanide chromophores, three or more lanthanide chromophores, four or more lanthanide chromophores, five or more lanthanide chromophores, six or more lanthanide chromophores, seven or more lanthanide chromophores, eight or more lanthanide chromophores, nine or more lanthanide chromophores, or more lanthanide chromophores. At least some of the lanthanide chromophores in a dendrimer can be of different types (e.g., different structures, compositions, and/or properties).

Figure 6:
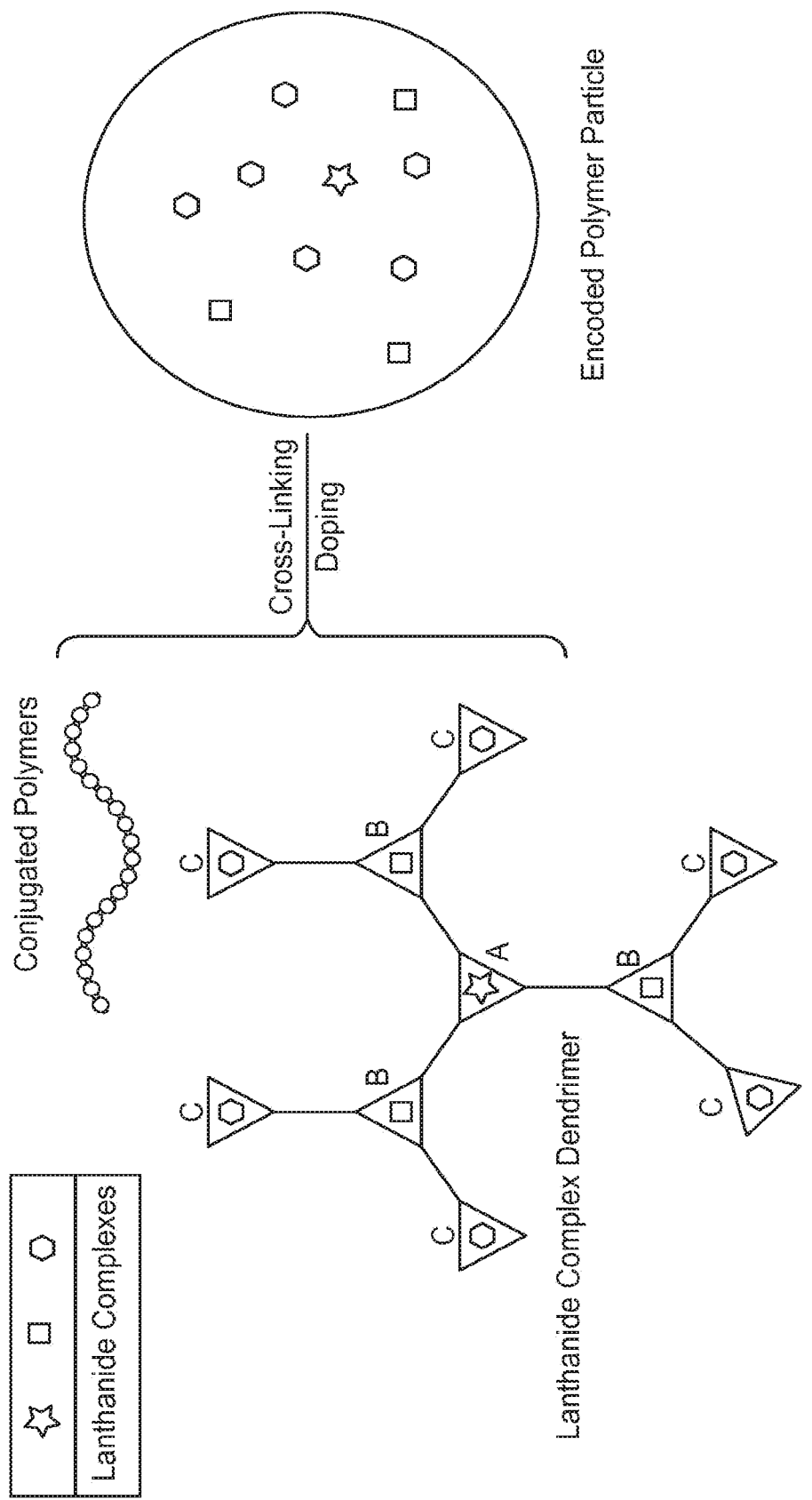
FIG. 6 depicts a schematic for preparing encoded chromophoric polymer particles from one type of conjugated polymer and lanthanide complex dendrimers.

FIG. 6 shows a schematic for preparing encoded chromophoric polymer particles from one type of conjugated polymer and lanthanide complex dendrimers. In one sample structure, the lanthanide complex dendrimer includes a center unit such as lanthanide complex A with three branches. The second generation of the dendrimer includes three lanthanide complexes (B), each of which also has three branches. The third generation of the dendrimer includes another three lanthanide complexes of another type (C). In some aspects, different ratios of LnA:LnB:LnC are created at the molecular level by varying the dendrimer structure and the generation number. The lanthanide complex dendrimers can be chemically cross-linked or physically blended with conjugated polymers to form the encoded chromophoric polymer particles. The star, hexagon, square, and circle represent different lanthanide species selected from La(III), Ce(III), Pr(III), Nd(III), Pm(III), Sm(III), Sm(II) Eu(III), Eu(II), Gd(III), Tb(III), Dy(III), Ho(III), Er(III), Tm(III), Yb(III), or Yb(II) species. The structures and/or the compositions of the encoded chromophoric polymer particles can be adjusted and varied to tune the optical properties (e.g., emission intensities, emission wavelengths, emission lifetimes) of the conjugated polymer and each lanthanide species.

Chromophoric Dye Compositions for Encoded Chromophoric Polymer Particles

In various aspects, the encoded chromophoric polymer particles of the present disclosure include one or more chromophoric dyes, such as fluorescent dyes, luminescent dyes, or combinations thereof. The chromophoric dye can be a small molecule dye. In certain aspects, the encoded chromophoric polymer particles of the present disclosure can include at least one type of chromophoric polymer as described herein and at least one type of chromophoric dye. The optical properties of the chromophoric polymer and/or chromophoric dye can be varied as desired. In some aspects, the chromophoric polymer is fluorescent so that both the polymer fluorescence and chromophoric dye luminescence can be used for encoding. In some aspects, the chromophoric polymer is weakly fluorescent or significantly quenched so that only the lanthanide materials are used for encoding. In certain aspects, the peak emission wavelength of the chromophoric dye is longer than the peak emission wavelength of the chromophoric polymer. In other aspects, the peak emission wavelength of the chromophoric dye is shorter than the peak emission wavelength of the chromophoric polymer.

In some aspects, the encoded chromophoric polymer particle provides a flexible polymer matrix (e.g., formed from one or more chromophoric polymers) that can accommodate the chromophoric dyes. Accordingly, in certain aspects, an encoded chromophoric polymer particle includes a polymer matrix and at least one chromophoric dye incorporated in the polymer matrix. Any suitable number and combination of chromophoric dye types can be incorporated in the polymer matrix, such at one or more chromophoric dyes, two or more chromophoric dyes, three or more chromophoric dyes, four or more chromophoric dyes, five or more chromophoric dyes, six or more chromophoric dyes, seven or more chromophoric dyes, eight or more chromophoric dyes, nine or more chromophoric dyes, ten or more chromophoric dyes, at fifty or more chromophoric dyes, or one hundred or more chromophoric dyes. The mass concentration of the chromophoric dyes relative to the entire encoded chromophoric polymer particle mass can be varied from 1% to 99%, more preferably between 10% and 99%, more preferably between 20% and 99%, more preferably between 30% and 99%, more preferably between 40% and 99%, and more preferably between 50% and 99%.

In certain aspects, at least some of the chromophoric dyes are distinct chromophoric dyes (e.g., having different structures, compositions, and/or properties). For example, some or all of the chromophoric dyes can have optical properties (e.g., emission spectra, emission wavelengths, emission intensities, emission lifetimes) that are distinguishable from one another. The concentrations of the chromophoric dyes in the encoded chromophoric polymer particle can be varied as desired. In some aspects, the encoded chromophoric polymer particle comprises a first concentration of a first chromophoric dye and a second concentration of a second chromophoric dye. In certain aspects, the encoded chromophoric polymer particle comprises two or more chromophoric dyes in a fixed ratio (e.g., fixed mass ratio) to each other.

In various aspects, the optical properties of the polymer matrix and one or more chromophoric dyes incorporated in the polymer matrix are designed to generate the desired optical encoding for the chromophoric polymer particle. In some aspects, the optical properties (e.g., emission spectra) of the polymer matrix and the one or more chromophoric dyes are distinguishable from one another. For example, in certain aspects, the emission peak(s) of the one or more chromophoric dyes have longer wavelengths than the emission peak(s) of the polymer matrix. In other aspects, the emission peak(s) of the one or more chromophoric dyes have shorter wavelengths than the emission peak(s) of the polymer matrix. In various aspects, the intensities of the emission peaks of the one or more chromophoric dyes and the polymer matrix are independently or semi-independently controllable. In certain aspects, there is energy transfer between the polymer matrix and the one or more chromophoric dyes. In alternative aspects, there is substantially no energy transfer between the polymer matrix and the one or more lanthanide chromophores.

In some aspects, the chromophoric dye incorporated in the polymer matrix is physically embedded or integrated into the polymer matrix. In some aspects, the chromophoric dye is chemically crosslinked and/or physically blended with the polymer matrix. In some aspects, a first chromophoric dye is crosslinked to the polymer matrix at a first concentration and a second chromophoric dye is crosslinked to the polymer matrix at a second concentration that is different from the first concentration. In some aspects, a first chromophoric dye is physically blended with the polymer matrix at a first concentration and a second chromophoric dye is physically blended with the polymer matrix at a second concentration that is different from the first concentration. In certain aspects, the chromophoric dye is chemically crosslinked and/or physically blended with a chromophoric polymer (e.g., a chromophoric polymer forming the polymer matrix).

A wide variety of chromophoric dyes are suitable for use with the encoded chromophoric polymer particles described herein. In certain aspects, the chromophoric dye is a fluorescent dye. In various aspects, the chromophoric dye is a small molecule organic dye. Examples of fluorescent dyes include but are not limited to: BODIPY and/or BODIPY derivatives, a squaraine and/or squaraine derivatives, a metal complex and/or metal complex derivatives, a porphyrin and/or porphyrin derivatives, a metalloporphyrin and/or metalloporphyrin derivatives, a phthalocyanine and/or phthalocyanine derivatives, a metal phthalocyanine and/or metal phthalocyanine derivatives, a lanthanide complex and/or lanthanide complex derivatives, a perylene and/or perylene derivatives, a cyanine and/or cyanine derivatives, a rhodamine and/or rhodamine derivatives, a coumarin and/or coumarin derivatives, and/or a xanthene and/or xanthene derivatives. In some aspects, the derivatives are selected from an alkyl derivative, aryl derivative, alkyne derivative, aromatic derivative, alkoxide derivative, aza derivative, or analogue thereof Methods for Preparing Encoded Chromophoric Polymer Particles In some aspects, methods of preparing encoded chromophoric polymer particles are disclosed. In some aspects, the chromophoric polymer particles can be formed using nanoprecipitation. The nanoprecipitation method involves the introduction of a solution of a polymer in a good solvent into a poor solvent, where the change in solubility collapses the polymer into a particle form. In certain aspects, the chromophoric polymer particles can be prepared using the mini-emulsion method.

In some aspects, the encoded chromophoric polymer particle can be prepared by using the solvent mixing method. The solvent mixing method comprises mixing a solution of the chromophoric polymer in a good solvent such as THF (tetrahydrofuran) with a miscible solvent (such as water) to fold the polymer into a nanoparticle form, simultaneously entrapping chromophores (e.g., lanthanide chromophores, chromophoric dyes) inside the particle. The encoded chromophoric polymer particles can be obtained after removal of the good solvent. In some aspects, the encoded chromophoric polymer particles are prepared by an emulsion or miniemulsion method, based on shearing a mixture comprising two immiscible liquid phases (such as water and another immiscible organic solvent) with the presence of a surfactant.

In some aspects, encoded chromophoric polymer particles can be formed by precipitation. This technique involves the rapid addition (e.g., facilitated by sonication or vigorous stirring) of a dilute chromophoric polymer solution (e.g., chromophoric polymer dissolved in an organic solvent) into an excess volume of non-solvent (but miscible with the organic solvent), such as water or another physiologically relevant aqueous solution. For example, in some of the procedures described herein, the chromophoric polymer can be first dissolved into an organic solvent where the solubility is good (good solvent), such as THF, after which the dissolved polymer in THF is added to an excess volume of water or buffer solution, which is a poor solvent for the hydrophobic chromophoric polymers but which is miscible with the good solvent (THF). The resulting mixture is sonicated or vigorously stirred to assist the formation of chromophoric polymer particles, then the organic solvent is removed to leave behind well dispersed chromophoric nanoparticles. In using this procedure, the chromophoric polymer should be sufficiently hydrophobic to dissolve into the organic solvent (e.g., THF). The introduction of a high density of hydrophilic functional groups on side chains for coupling to biomolecules or high density of hydrophilic side chains will make the resulting polymer, in a fashion similar or identical to the behavior of polyelectrolytes, insoluble or poorly soluble in an organic solvent (e.g., THF).

In some aspects, encoded chromophoric polymer particles are formed by other methods, including but not limited to various methods based on emulsions (e.g., mini or micro emulsion) or precipitations or condensations. Other polymers having hydrophobic functional groups can also be employed, in which the hydrophobic functional groups do not affect the collapse and stability of the chromophoric polymer particle. The hydrophobic functional groups on the surface of the nanoparticles can then be converted to hydrophilic functional groups (e.g., by post-functionalization) for bioconjugation or directly link the hydrophobic functional groups to biomolecules. This latter approach can work particularly well using functional groups that are both hydrophobic and clickable (i.e., chemical reactions that fall within the framework of click chemistry), including but not limited to alkyne, strained alkyne, azide, diene, alkene, cyclooctyne, and phosphine groups.

In certain aspects, a method of preparing an encoded chromophoric polymer particle comprises providing a solution comprising a polymer (e.g., a chromophoric polymer) and one or more chromophores (e.g., lanthanide chromophores, chromophoric dyes) in a non-polar solvent. The solution can then be introduced into a polar solvent to produce an encoded chromophoric polymer particle. In some aspects, the one or more chromophores are associated with the polymer at a fixed ratio. In various aspects, multiple chromophores associated with a polymer each have distinguishable optical properties (e.g., emission spectra) and are each at a fixed ratio with respect to one another. In certain aspects, the solution can include a plurality of polymers each associated with a respective set of one or more chromophores at respective fixed ratios, e.g., two, three, four, five, six, or more pluralities.

Polyelectrolyte-Coated Encoded Chromophoric Polymer Particles

In some aspects, the encoded chromophoric polymer particles provided herein can have a polyelectrolyte coating. Advantageously, a polyelectrolyte coating can, e.g., improve the colloidal stability of polymer particles in solutions that have high ionic strength, contain bivalent metal ions, or both. The improved colloidal stability as compared to some polymer particles without the polyelectrolyte coating, e.g., can allow polymer particles to be used in an assay without losing their functionality. In certain aspects, the compositional makeup of the polyelectrolyte coating can be tailored to reduce or eliminate aggregation of the polymer particles in solution, e.g., high ionic strength solutions. In addition, under certain conditions, ions (e.g., bivalent ions) in a solution can chelate groups on the surface of polymer particles, thereby affecting aggregation properties. In some aspects, polyelectrolyte coatings are used to reduce or eliminate aggregation of the polymer particles in solution.

The polyelectrolyte coatings can have a layer thickness ranging from about two to four nanometers, thereby adding about four to eight nanometers to the diameter of the nanoparticle including the polymer particle and the polyelectrolyte coating.

The polyelectrolytes in the coating can form on the surface of the polymer particles in a variety of ways. For example, if one type of polyelectrolyte is used, the polyelectrolyte polymer molecules can physically blend together to form the coating. If two or more types of polyelectrolytes are used, the polyelectrolyte polymer molecules can physically blend together to form the coating or, in some aspects, the different polyelectrolytes may form regions (or rafts) on the surface of the nanoparticle. In some aspects, the polyelectrolytes can be chemically crosslinked. For example, some or all of the polyelectrolytes in the coating can be chemically crosslinked using any crosslinking reaction generally well known in the art. The polyelectrolytes may also be chemically crosslinked with the condensed polymer(s) forming the polymer particle. In some aspects, the coating can include more than one layer of polyelectrolytes. For example, the coating can include two layers of polyelectrolytes, three layers of polyelectrolytes, or more layers of polyelectrolytes. The polyelectrolytes in the layers can include the same or different types of polyelectrolytes.

In some aspects, "polyelectrolytes" can include, e.g., polymers whose repeating units bear an electrolyte group having a charge. In some aspects, the polyelectrolytes can include polymers in which all the repeating units along the polymer bear an electrolyte group. In certain aspects, some of the repeating units of the polymer bear an electrolyte group. For example, polyelectrolytes of the present disclosure can include polymers in which at least 99%, 95%, 90%>, 85%, 80%, 75%, 70%, 65%, 60%, 55%, 50%, 45%, 40%, 35%, 30%, 25%, 20%, 15%, 10%, 5%, or 1% of the repeating units in the polymer bear an electrolyte group. In some aspects, polyelectrolytes of the present disclosure can include polymers in which at least 99%, 95%, 90%, 85%, or 80% of the repeating units in the polymer bear an electrolyte group.

In some aspects, the polyelectrolytes can include at least one type of electrolyte group. For example, the polyelectrolytes can include only one type of electrolyte group, or two or more types of electrolyte groups. The various electrolyte groups described herein can be included in a variety of different types of polyelectrolytes. Example polyelectrolytes in the present disclosure can include, but are not limited to, poly(styrene sulfonate), polyphosphate, polyacrylate, polymethacrylate, polyacrylate-co-maleate, polyacrylamide, chitosan, polysaccharide, polylysine, polyhistidine, and polypeptide. The electrolyte group described herein can be included in the polymer backbone, included in side chains attached to the polymer backbone, and/or included in a group that is attached to a side chain of a polymer.

A wide variety of electrolyte groups can be used in the present disclosure. Generally, any group that generates a charge under certain conditions can be used for the polyelectrolytes. For example, the electrolyte group can include an anion or a cation. In some aspects, the electrolyte group can include one anion or one cation. Alternatively, the electrolyte group can include more than one anion and/or cation such that the electrolyte group includes an overall negative or positive charge. The charge on the electrolyte groups can be a permanent charge or a charge generated according to a specific pH of a solution (e.g., a hydrogen can dissociate to form the charged electrolyte group). In some aspects, the electrolyte group can be a salt (e.g., neutralized with a counterion) prior to being dissolved in an aqueous solution. In some aspects, the electrolyte groups can include, but are not limited to, a carboxyl group, a sulfonate group, a phosphate group, an amino, a hydroxyl group, and a mercapto group. In some aspects, the charges of the electrolyte groups can be generated depending on acidic or basic solution characteristics. For example, a carboxyl group, sulfonate group, phosphate group, hydroxyl group, or mercapto group can be negatively charged, e.g., according to a pH of the solution and the pKa of the respective electrolyte group. In aqueous solutions, the electrolyte groups on polymers can dissociate to form charged groups and thereby making the polymers charged, forming the polyelectrolyte. In some aspects, the electrolyte groups can be substituted with substituents to place a permanent charge on the electrolyte group. For example, an amino group can include a quaternary ammonium cation that has a permanent positive charge. Substituents for the electrolyte groups can be varied, such as alkyl, aryl, CN, amino, sulfide, aldehyde, ester, ether, acid, hydroxyl or halide. In certain aspects, the substituents on the electrolyte groups can provide the charge to the electrolyte.

One aspect of the present disclosure includes modifying the zeta potential of the polymer particles by providing a polyelectrolyte coating. This coating can be used to modify, e.g., the surface charge of the nanoparticles and prevent aggregation in solutions. Depending on the solution, the zeta potential can be tailored to prevent aggregation. In some aspects, zeta potential is a parameter to evaluate whether the particles dispersed in a solution can resist aggregation. For example, particles (e.g., polymer particles coated with polyelectrolytes) will be stable (e.g., resist aggregation) when the particles have a zeta potential more positive than +30 mV or more negative than −30 mV. Higher value zeta potentials can provide more stability against aggregation. For example, a dispersion of particles with +/−60 mV can provide excellent stability. Depending on the selected polyelectrolyte(s) described herein, the present disclosure includes particle dispersions (e.g., polymer particles having a polyelectrolyte coating) having zeta potentials that are more positive than about +30 mV, more positive than about +40 mV, more positive than about +50 mV, or move positive than about +60 mV. The present disclosure includes particle dispersions (e.g., polymer particles having a polyelectrolyte coating) having zeta potentials that are more negative than about −30 mV, more negative than about −40 mV, more negative than about −50 mV, or move negative than about −60 mV. The particles having a polymer particle with a polyelectrolyte coating can be prepared using the methods described herein for the wide variety of polyelectrolytes. The zeta potential of particle dispersions can then be determined using a variety of techniques, such as by using instruments designed to measure zeta potential, e.g., by a Malvern Zetasizer.

In certain aspects, the present disclosure includes nanoparticles that include a polymer particle having a coating including more than one polyelectrolyte polymer. For example, the coatings can include two different polyelectrolytes, three different polyelectrolytes, four different polyelectrolytes, or more and at any desired ratio.

Functionalization and Bioconjugates of Encoded Chromophoric Polymer Particles

In some aspects, the present disclosure provides functionalized encoded chromophoric polymer particles for biomolecular encoding. The functionalized particle includes an encoded chromophoric polymer particle and a functional group that is physically or chemically attached to the particle.

In some aspects, this invention provides encoded chromophoric polymer particle functionalized with a functional group. In some aspects, the term "functional group" refers to any chemical unit that can be attached, such as by any stable physical or chemical association, to the encoded chromophoric polymer particle, thereby rendering the surface of the chromophoric polymer particle available for conjugation or bioconjugation. In some aspects, functional groups can be hydrophobic functional groups. Examples of hydrophobic functional groups include but not limited to alkyne, strained alkyne, azide, diene, alkene, cyclooctyne, and phosphine groups (for click chemistry). In some aspects, functional groups can be hydrophilic functional groups. Examples of hydrophilic functional groups include but not limited to carboxylic acid or salts thereof, amino, mercapto, azido, diazo, aldehyde, ester, hydroxyl, carbonyl, sulfate, sulfonate, phosphate, cyanate, succinimidyl ester, substituted derivatives thereof. Such functional groups can be found by one of ordinary skill in the art, for example in Bioconjugate Techniques (Academic Press, New York, 1996 or later versions) the content of which is herein incorporated by reference in its entirety for all purposes.

In some aspects, encoded chromophoric polymer particles are functionalized using functional groups including, without limitation, any of the following: an aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or combination thereof.

In some aspects, a functional group is created with covalent bonding to the backbone, side chain, or terminating unit of the chromophoric polymer. Therefore, the resulting encoded chromophoric polymer particles exhibit narrowband emission and simultaneously have functional groups for bioconjugation. Such functional groups could be found by one of ordinary skill in the art, for example in Bioconjugate Techniques (Academic Press, New York, 1996 or later versions) the content of which is herein incorporated by reference in its entirety for all purposes. In some aspects, each chromophoric polymer particle has only one functional group. In some aspects, each chromophoric polymer particle has only two functional groups. The two functional groups can be the same or different. In some aspects, each chromophoric polymer particle has three or more functional groups. The three or more functional groups can be the same or different.

In certain aspects of the present disclosure, the degree of functionalization of the encoded chromophoric polymer particle can be varied as desired. In some aspects, the encoded chromophoric polymer particles provided herein are modified to form a single-molecule polymer particle that can be monovalent, bivalent, or multivalent. The modification is to remove some polymer molecules from the particle, but leave only one molecule that can have just one functional group, two or more functional groups. In one aspect, an engineered surface can be used to facilitate the modification. The engineered surface can have certain functional groups such as aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, and combinations thereof. In general, any other functional groups that are suitable for bioconjugation can be used. Such functional groups could be found by one of ordinary skill in the art, for example in Bioconjugate Techniques (Academic Press, New York, 1996 or later versions). The surface can be a flat surface such as a coverslip or a curved surface from any particles. The surfaces can be silica, metal, semiconducting, silicon, and different polymer surfaces. The functionalized multi-molecule chromophoric polymer particle described above is attached to the surface by only one chromophoric polymer molecule via any stable physical or chemical association. All the free molecules (except the one associated with the surface) in the chromophoric polymer particle can be removed, such as by washing the surface with an organic solvent, so that only the molecule associated with the surface is retained. Then the single-molecule chromophoric particle can be released from the surface by any physical or chemical methods. The resulting single-molecule particle could be monovalent, bivalent, or multivalent, depending on the number of functional groups in the original polymer molecule.

In some aspects, advantages can arise from using encoded chromophoric polymer particles that include a single polymer molecule having at least one functional group at a terminal unit. For example, the attachment of only one functional group to a terminal unit of a chromophoric polymer can be well controlled in polymer synthesis. For example, a chemical unit comprising a functional group can serve as a polymerization initiator as well as a growth catalyst in polymer synthesis, and in this way each polymer molecule includes just one functional group at the terminus.

Attachment of functional groups only to the two terminal units of a linear chromophoric polymer can also be well controlled in polymer synthesis. For example, a chemical unit comprising a functional group can be used as a capping agent to terminate the polymer growth in polymer synthesis, thereby resulting in each linear polymer molecule including only two functional groups in the two terminal units. Similarly, the attachment of functional groups for multivalent polymer particles can be well controlled in polymer synthesis, e.g., functional groups can only be added to the three terminal units of a three-arm branched polymer.

In some aspects, the present disclosure discloses a bioconjugate of the encoded chromophroic polymer particle for biomolecular encoding. The bioconjugates also include chromophoric polymer particle as described above associated with biological particles such as viruses, bacteria, cells, biological or synthetic vesicles such as liposomes, or combinations thereof. In some aspects, the term "biomolecule" is used to describe a synthetic or naturally occurring protein, glycoprotein, peptide, amino acid, metabolite, drug, toxin, nuclear acid, nucleotide, carbohydrate, sugar, lipid, fatty acid, and the like, or combinations thereof. In some aspects, the biomolecule is a polypeptide or a polynucleotide. In some aspects, the biomolecule is an antibody, an avidin, a biotin, or a combination thereof. In some aspects, the bioconjugate is formed by the attachment of a biomolecule to one or more functional groups of the encoded chromophoric polymer particle. The attachment may be direct or indirect. Optionally, the biomolecule is attached to the functional group of the chromophoric polymer particle via a covalent bond. For example, if the functional group of the polymer particle is a carboxyl group, a protein biomolecule can be directly attached to the polymer particle by cross-linking the carboxyl group with an amine group of the protein molecule. In some aspects, each polymer particle has only one type of biomolecule attached. In some aspects, the biomolecular conjugation does not change substantively the emissive properties of the chromophoric particle. For example, the bioconjugation does not change the emission spectra, does not reduce fluorescence or luminescence quantum yield, does not change the photostability, etc.

In various aspects of the present disclosure cross-linking agents can be utilized to facilitate bioconjugation of encoded chromophoric polymer particles. In some aspects, the term "cross-linking agent" is used to describe a compound or moiety that is capable of forming a chemical bond between molecular groups on similar or dissimilar molecules so as to covalently bond together the molecules. Examples of common cross-linking agents are known in the art. See, for example, Bioconjugate Techniques (Academic Press, New York, 1996 or later versions). Indirect attachment of the biomolecule to monovalent chromophoric polymer particles can occur through the use of "linker" molecules, for example, avidin, streptavidin, neutravidin, biotin or a like molecule.

In some aspects, analysis of a target analyte molecule (e.g., a protein) is achieved using encoded chromophoric polymer particles conjugated to biomolecules that specifically bind to the target analyte.

In some aspects, fluorescent and/or luminescent encoded chromophoric polymer particles are conjugated to one or more molecules that provide a function or other benefit, including without limitation, binding affinity for a target analyte.

In some aspects, the analyte is a polypeptide, a polynucleotide, a cell, a virus, a small molecule, a drug, a toxin, a carbohydrate, a sugar, a lipid, or a fatty acid.

In some aspects, the target analyte molecule is a polypeptide, such as a protein, and the biomolecule conjugated to a encoded chromophoric polymer particle is a primary antibody that specifically binds to the target analyte protein.

In other aspects, the target analyte molecule is a protein of interest bound to a primary antibody for said protein, and the biomolecule conjugated to an encoded chromophoric polymer particle is a secondary antibody that specifically binds to the primary antibody.

In other aspects, the target analyte molecule is a biotinylated protein of interest, and the biomolecule conjugated to an encoded chromophoric polymer particle is an avidin (e.g., streptavidin) that specifically binds to the biotinylated protein.

In some aspects, the term "biotin" refers to any one of a variety of biotin derivatives and analogs that are effective in avidin binding. Suitable biotin moieties include those moieties that enable the biotinylated peptide fragment to be isolated by avidin and related avidin proteins. Representative biotin moieties include biotin derivatives such as iminobiotin, biocytin, and caproylamidobiotin, and biotin analogs such as desthiobiotin and biotin sulfone.

In some aspects, the term "avidin" refers to any biotin-binding protein other than an immunoglobulin that binds biotin including both natural proteins and recombinant and genetically engineered proteins. The term includes the two common biotin-binding proteins known as "egg white" or "avian" avidin and "streptavidin." Egg white or avian avidin, commonly referred to simply as avidin, is a protein that is a constituent of egg white and forms a noncovalent complex with biotin. Streptavidin is an avidin protein isolated from the actinobacterium Streptomyces avidinii and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. The term also refers to avidin derivatives including succinyl avidin, ferritin avidin, enzyme avidin, and crosslinked avidin.

In some aspects, the target analyte molecule is a polynucleotide, such as DNA or RNA, and the biomolecule conjugated to an encoded chromophoric polymer particle is a complementary polynucleotide that specifically binds to the target analyte polynucleotide.

In some aspects, fluorescent and/or luminescent encoded chromophoric polymer particles may be conjugated to one or more molecules that alter other properties of the polymer particles, such as their size, fluorescence, hydrophobicity, non-specific binding or adsorption properties, and the like.

In some aspects, conjugation of biomolecules to encoded chromophoric polymer particles can include attachment of a functional group, including but not limited to attachment of carboxyl groups to polymer particles. In some aspects, carboxyl groups can be reacted to N-hydroxysuccinimide (NHS) in the presence of a carbodiimide such as 1-ethyl-3-[3-dimethylaminopropyl]carbodiimide hydrochloride (EDC) to produce amine-reactive esters of carboxylate groups for crosslinking with primary amine groups present on certain biomolecules.

In some aspects, carboxylated encoded chromophoric polymer particles are conjugated to a biomolecule, such as a protein, by mixing of the encoded chromophoric polymer particles and the biomolecules, e.g., in a HEPES buffer (20 mM, pH=7.4) solution containing 0.1 PEG (MW3350). Formation of a peptide bond between the carboxyl groups on polymer particles and the amine groups of the biomolecule can be catalyzed by EDC. However, in some aspects, due to the intrinsically hydrophobic nature of the polymer particles, biomolecules tend to nonspecifically adsorb onto the particle surface. In some aspects, Triton X-100 and/or bovine serum albumin (BSA) are introduced to reduce non-specific adsorption of a biomolecule onto the surface of a polymer particle.

In addition to the examples described herein, in some aspects other strategies and methods for conjugation of biomolecules to encoded chromophoric polymer particles can be used, including those disclosed, e.g., in PCT/US2010/056079 and PCT/US2012/071767. Other strategies and methods for conjugation of biomolecules to encoded chromophoric polymer particles can be found by one of ordinary skill in the art, for example in Bioconjugate Techniques (Academic Press, New York, 1996 or later versions).

Preparations of Encoded Chromophoric Polymer Particles

The encoded chromophoric polymer particles described herein can be prepared in a wide variety of formats. In some aspects of the present disclosure, a suspension of encoded chromophoric polymeric particles is provided. The suspension can include at least one plurality of encoded chromophoric polymeric particles and a continuous phase (e.g., a solvent such as a liquid). In another aspect, the present disclosure provides a suspension of encoded chromophoric polymer particles comprising: a continuous phase composed of a solvent; and a discontinuous phase composed of: a first plurality of encoded chromophoric polymer particles; a second plurality of encoded chromophoric polymer particles; wherein the optical properties (e.g., emission spectra) of the first plurality of encoded chromophoric polymer particles is distinct from the optical properties of the second plurality of encoded chromophoric polymer particles.

In some aspects, the present disclosure provides a suspension of chromophoric polymer particles comprising a plurality of chromophoric polymer particles and one or more additional pluralities of chromophoric polymer particles. In some aspects, the suspension includes 2 pluralities of encoded chromophoric polymer particles, 3 pluralities of encoded chromophoric polymer particles, 4 pluralities of encoded chromophoric polymer particles, 5 pluralities of encoded chromophoric polymer particles, 6 pluralities of encoded chromophoric polymer particles, 7 pluralities of encoded chromophoric polymer particles, 8 pluralities of encoded chromophoric polymer particles, 9 pluralities of encoded chromophoric polymer particles, 10 pluralities of encoded chromophoric polymer particles, 20 pluralities of encoded chromophoric polymer particles, 30 pluralities of encoded chromophoric polymer particles, 40 pluralities of encoded chromophoric polymer particles, 50 pluralities of encoded chromophoric polymer particles, 100 pluralities of encoded chromophoric polymer particles, 500 pluralities of encoded chromophoric polymer particles, 1000 pluralities of encoded chromophoric polymer particles, or 5000 pluralities of encoded chromophoric polymer particles. In some aspects, the suspension comprises at most 3 pluralities of encoded chromophoric polymer particles, at most 4 pluralities of encoded chromophoric polymer particles, at most 5 pluralities of encoded chromophoric polymer particles, at most 6 pluralities of encoded chromophoric polymer particles, at most 7 pluralities of encoded chromophoric polymer particles, at most 8 pluralities of encoded chromophoric polymer particles, at most 9 pluralities of encoded chromophoric polymer particles, at most 10 pluralities of encoded chromophoric polymer particles, at most 20 pluralities of encoded chromophoric polymer particles, at most 30 pluralities of encoded chromophoric polymer particles, at most 40 pluralities of encoded chromophoric polymer particles, at most 50 pluralities of encoded chromophoric polymer particles, at most 100 pluralities of encoded chromophoric polymer particles, at most 500 pluralities of encoded chromophoric polymer particles, at most 1000 pluralities of encoded chromophoric polymer particles, or at most 5000 pluralities of encoded chromophoric polymer particles.

In some aspects, at least some of the pluralities of encoded chromophoric polymer particles in a suspension are distinguishable from other pluralities, e.g., have different optical properties. In some aspects, an emission spectrum of at least one plurality is distinguishable from an emission spectrum of at least one other plurality. In some aspects, an emission lifetime of at least one plurality is distinguishable from an emission lifetime of at least one other plurality. In some aspects, an emission intensity of at least one plurality is distinguishable from an emission intensity of at least one other plurality. In some aspects, an emission wavelength of at least one plurality is distinguishable from an emission wavelength of at least one other plurality. In certain aspects, each of the pluralities of encoded chromophoric polymer particles (e.g., two, three, four, five, six, or more pluralities) have distinct emission spectra, emission lifetimes, emission intensities, and/or emission wavelengths.

In some aspects, at least one of the chromophores of a first plurality of encoded chromophoric polymer particles in a suspension is the same as at least one of the chromophores of a second plurality of encoded chromophoric particles. In certain aspects, the first plurality of encoded chromophoric polymer particles is at a different concentration in the suspension than the second plurality of encoded chromophoric polymer particles.

In some aspects, at least one plurality of encoded chromophoric polymer particles in a suspension comprises different chromophores than at least one other plurality. For example, in various aspects, at least two of the pluralities of encoded chromophoric polymer particles have different chromophores, e.g., different lanthanide chromophores. In various aspects, at least two of the pluralities of encoded chromophoric polymer particles have different lanthanide chromophore concentrations (e.g., by mass). As another example, in various aspects, at least two of the pluralities of encoded chromophoric polymer particles have different chromophoric polymers. In various aspects, at least two of the pluralities of encoded chromophoric polymer particles have different chromophoric polymer concentrations (e.g., by mass). In yet another example, in various aspects, at least two of the pluralities of encoded chromophoric polymer particles have different chromophoric dyes. In various aspects, at least two of the pluralities of encoded chromophoric polymer particles have different chromophoric dye concentrations (e.g., by mass).

In some aspects, at least one plurality of encoded chromophoric polymer particles in a suspension is polydisperse. In some aspects, each of the pluralities of encoded chromophoric polymer particles in a suspension is relatively polydisperse. In some aspects, at least one plurality is monodisperse. In some aspects, each of the pluralities is relatively monodisperse.

In some aspects, a functional group attached to at least one plurality is different from a functional group attached to at least one other plurality. In some aspects, a biomolecule attached to at least one plurality is different from a biomolecule attached to at least one other plurality. In some aspects, the biomolecules specifically associate with different analytes.

In some aspects, the present disclosure provides a kit for detecting analytes in a sample. In certain aspects, the kit includes a suspension of encoded chromophoric polymer particles containing two or more pluralities of encoded chromophoric polymer particles, as described above. In some aspects, the kit includes biomolecules conjugated to functional groups attached to encoded chromophoric polymer particles. In some aspects, the kit comprises biomolecules configured for an end-user to conjugate to functional groups attached to encoded chromophoric polymer particles. In some aspects, the biomolecule is a polypeptide such as a protein, a polynucleotide such as DNA and/or RNA, a metabolite such as a lipid, fatty acid, sugar, nucleotide or amino acid, or a cell, a virus or a viral particle.

In some aspects, the present disclosure provides an optical encoding system. In certain aspects, the optical encoding system includes a first encoded chromophoric polymer particle and a second encoded chromophoric polymer particle having optically detectable codes that are distinguishable from each other. In certain aspects, the system includes a plurality of encoded chromophoric polymer particles at least some of which have optically detectable codes that distinguishable from each other.

Methods of Using Encoded Chromophoric Polymer Particles

The present disclosure further provides methods of using the encoded chromophoric polymer particles described herein. For example, the present disclosure provides methods of fluorescence-based detection using the encoded chromophoric polymer particles as a novel class of fluorescent probe and their bioconjugates for a variety of applications. These include but are not limited to flow cytometry, fluorescence activated sorting, immunofluorescence, immunohistochemistry, fluorescence multiplexing, DNA and gene analysis, protein analysis, metabolite analysis, lipid analysis, Förster resonance energy transfer (FRET)-based sensors, high throughput screening, cell detection, bacteria detection, virus detection, biomarker detection, cellular imaging, in vivo imaging, bioorthogonal labeling, fluorescence-based biological assays such as immunoassays and enzyme-based assays, and a variety of fluorescence techniques in biological assays and measurements. In certain aspects, the encoded chromophoric polymer particles herein have a number of advantages for use as detection agents, e.g., for detection of proteins or peptides such as in the course of Western blot analysis. Encoded chromophoric polymer particles according to the present disclosure can comprise any suitable polymer subunit or subunits that enable the detection of proteins or peptides, and in particular, proteins.

In certain aspects, the encoded chromophoric polymer particles disclosed herein can be used for methods of detection that involve multiplexing over a variety of wavelength ranges, intensity ranges, lifetime ranges, or combinations thereof.

In some aspects, a method of detecting analytes is provided, the method comprising contacting a sample comprising an analyte with an encoded chromophoric polymer particle. In other aspects, the method comprises contacting a sample comprising an analyte with a suspension of encoded chromophoric polymer particles. In some aspects, the sample comprises blood, urine, stool, lymph, saliva, or cerebrospinal fluid. In some aspects, the sample is derived from a subject, such as an animal or a single-celled organism. In some aspects, the sample comprises a living animal or tissue. In some aspects, the analyte has a binding affinity for a biomolecule attached to an encoded chromophoric polymer particle. In some aspects, the analyte comprises a polypeptide, a polynucleotide, a cell, a cellular fraction, a virus, a drug, a toxin, a carbohydrate, a sugar, a lipid, or a fatty acid.

In some aspects, the method further comprises measuring a signal emitted from the sample, the suspension, and/or an encoded chromophoric polymer particle. In some aspects, the method further comprises detecting an optically detectable code emitted by an encoded chromophoric polymer particle in the sample. In various aspects, the detection of the optically detectable code indicates the presence of the analyte, the identity of the analyte, and/or the concentration of the analyte in the sample.

In some aspects, the method further comprises exciting the sample, the suspension, and/or an encoded chromophoric polymer particle with a source of electromagnetic radiation. In some aspects, the electromagnetic radiation passes through a spectral filter, a multichroic mirror, or a combination thereof. In some aspects, the peak wavelength of electromagnetic radiation exciting the sample is between about 200 nm and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm.

In some aspects, the method further comprises using a signal emitted from the sample and the suspension to measure the analyte. In some aspects, the method further comprises using the spectrum of a signal emitted from the sample and the suspension to measure the analyte. In some aspects, the method further comprises the lifetime of a signal emitted from the sample and the suspension to measure the analyte. In some aspects, the method further comprises using the intensity of a signal emitted from the sample and the suspension to measure the analyte. For example, the method can comprise using the optically detectable code emitted by an encoded chromophoric polymer particle to measure the analyte. In certain embodiments, the presence of the analyte in the sample, the identity of the analyte, and/or the concentration of the analyte is determined based on one or more optical properties of the optically detectable code, such as the spectrum, wavelength, intensity, and/or lifetime of the optically detectable code.

In some aspects, the method further comprises separating the analyte from the sample. In some aspects, separating the analyte from the sample comprises directing an encoded chromophoric polymer particle associated with the analyte to the flow cell of a flow cytometer or a microfluidic device. In some aspects, separating the analyte from the sample comprises attaching an encoded chromophoric polymer particle associated with the analyte to a solid support.

In another aspect, the present disclosure provides methods for detecting a plurality of analytes in a sample, such as 2 pluralities of analytes, 3 pluralities of analytes, 4 pluralities of analytes, 5 pluralities of analytes, 6 pluralities of analytes, 7 pluralities of analytes, 8 pluralities of analytes, 9 pluralities of analytes, 10 pluralities of analytes, 20 pluralities of analytes, 30 pluralities of analytes, 40 pluralities of analytes, 50 pluralities of analytes, 100 pluralities of analytes, 500 pluralities of analytes, 1000 pluralities of analytes, or 5000 pluralities of analytes. In certain aspects, the methods described herein are used to detect at most 3 pluralities of analytes, at most 4 pluralities of analytes, at most 5 pluralities of analytes, at most 6 pluralities of analytes, at most 7 pluralities of analytes, at most 8 pluralities of analytes, at most 9 pluralities of analytes, at most 10 pluralities of analytes, at most 20 pluralities of analytes, at most 30 pluralities of analytes, at most 40 pluralities of analytes, at most 50 pluralities of analytes, at most 100 pluralities of analytes, at most 500 pluralities of analytes, at most 1000 pluralities of analytes, or at most 5000 pluralities of analytes.

In certain aspects, the present disclosure provides a method for detecting a first set of analytes and a second set of analytes, e.g., based on distinguishable optical properties of the encoded chromophoric polymer particles used to detect the analytes. In some aspects, the first set of analytes binds a first set of biomolecules attached to a first set of encoded chromophoric polymer particles, and the second set of analytes binds a second set of biomolecules attached to a second set of encoded chromophoric polymer particles. In various aspects, the method further comprises determining the presence, identity, and/or concentration of the first set of analytes, and determining the presence, identity, and/or concentration of the second set of analytes. In various aspects, the first and second sets of encoded chromophoric polymer particles have respective first and second optically detectable codes that are distinguishable from one another, and the detection of the first and second optically detectable codes enables determination of the presence, identity, and/or concentration of the corresponding analytes. In various aspects, the first and second sets of encoded chromophoric polymer particles have emission spectra that are distinguishable from one another, and the detection of the emission spectra enables determination of the presence, identity, and/or concentration of the corresponding analytes. In various aspects, the first and second sets of encoded chromophoric polymer particles each have emission lifetimes that are distinguishable from one another, and the detection of the emission lifetimes enables determination of the presence, identity, and/or concentration of the corresponding analytes. In various aspects, the first and second sets of encoded chromophoric polymer particles each have emission intensities that are distinguishable from one another, and the detection of the emission intensities enables determination of the presence, identity, and/or concentration of the corresponding analytes.

In certain aspects, a method for detecting two or more analytes in a sample comprises: providing a suspension of encoded chromophoric polymer particles, as described herein, comprising a first plurality of encoded chromophoric polymer particles comprising a biomolecule configured to selectively associate with a first analyte in the sample; a second plurality of encoded chromophoric polymer particles comprising a biomolecule configured to selectively associate with a second analyte in the sample; contacting the suspension with a sample under conditions and for a time sufficient to permit the encoded chromophoric polymer particles to associate with the two or more analytes in the biological sample; contacting the suspension comprising the encoded chromophoric polymer particles associated with an analyte with at least one light source capable of exciting the one or more encoded chromophoric polymer particles; and measuring an optical property (e.g., emission spectrum) from the sample. In some aspects where the sample is an animal or is derived from an animal, the suspension is contacted with at least one light source in vivo, and the optical property is measured in vivo.

In some aspects, the method further comprises determining a ratio of emission intensities of two or more chromophores, such as a polymer matrix and one or more lanthanide chromophores. In certain aspects in which the pluralities of encoded chromophoric polymer particles are relatively monodisperse, the emission spectrum of the polymer matrix can be used as an internal standard.

In some aspects, the method comprises two, three, four, five, six, seven, eight, nine, ten or more different analytes. In some aspects, the method comprises two, three, four, five, six, seven, eight, nine, ten or more different encoded chromophoric polymer particles attached to two, three, four, five, six, seven, eight, nine, ten or more different biomolecules that each have a binding affinity for one of the two, three, four, five, six, seven, eight, nine, ten or more different analytes.

In some aspects, compositions, methods and systems of the present disclosure are used for flow cytometry and other fluorescence activated sorting methods. In some aspects, emission properties of chromophoric polymer particles are quantified and used to actively separate and isolate the particles and analytes attached directly or indirectly to the particles. In some aspects, an emission spectrum (wavelength), lifetime, and/or intensity of chromophoric polymer particles can be used to actively separate or otherwise isolate the particles and analytes attached directly or indirectly to the particles.

In some aspects, compositions, methods and systems of the present disclosure are used for immunoassays including, but not limited to, immunocytochemistry, immunohistochemistry and enzyme-based assays. In some aspects, the immunoassay is used to detect an analyte comprising a polypeptide such as a protein. In some aspects, an antibody is bound indirectly to a chromophoric polymer particle, e.g., by conjugation to a functional group that is attached to the particle. In some aspects, the antibody is a primary antibody. In some aspects the antibody is a secondary antibody. In some aspects both a primary antibody and a secondary antibody are bound indirectly to a chromophoric polymer particle. In some aspects, the assay is performed on cells that have been dissociated from a tissue. In other aspects, the assay is performed on intact (non-dissociated) tissue. In some aspects, encoded chromophoric polymer particles are used to perform enzyme-based assays, such as an enzyme-linked immunosorbent assay (ELISA).

In some aspects, compositions, methods and systems of the present disclosure are used for analysis of polynucleotides, including but not limited to polymerase chain reaction, reverse transcriptase PCR, ligase chain reaction, loop mediated amplification, reverse transcription loop mediated amplification, helicase dependent amplification, reverse transcription helicase dependent amplification, recombinase polymerase amplification, reverse transcription recombinase polymerase amplification, catalytic hairpin assembly reactions, hybridization chain reaction, entropy-driven catalysis, strand displacement amplification, reverse transcription strand displacement amplification, nucleic acid sequence based amplification, transcription mediated amplification, self-sustained sequence replication, single primer isothermal amplification, signal mediated amplification of RNA technology, rolling circle amplification, hyper branched rolling circle amplification, exponential amplification reaction, smart amplification, isothermal and chimeric primer-initiated amplification of nucleic acids, multiple displacement amplification, and/or in situ hybridization.

In some aspects, compositions, methods and systems of the present disclosure are used for analysis of metabolites including lipids, sugars, nucleotides, amino acids, fatty acids and other metabolites.

In some aspects, compositions, methods and systems of the present disclosure are used for detecting cells, including but not limited to eukaryotic cells in vitro, eukaryotic cells in vivo, and prokaryotic bacterial cells.

In some aspects, compositions, methods and systems of the present disclosure are used for detecting organelles and other subcellular fractions including but not limited to mitochondria, endoplasmic reticulum and/or synaptosomes.

In some aspects, compositions methods and systems of the present disclosure are used for detecting biomarkers in a bioassay. The biomarker can be, without limit, a polypeptide such as a protein, a polynucleotide such as DNA and/or RNA, a metabolite such as a lipid, fatty acid, sugar, nucleotide or amino acid, a cell, a virus or viral particle.

In some aspects, compositions methods and systems of the present disclosure are used for fluorescence multiplexing over a variety of wavelength, lifetime, and intensity ranges. In some aspects, fluorescence multiplexing with encoded chromophoric polymer particles provides for simultaneous and/or sequential analysis of multiple analytes in a sample, including but not limited to polypeptides such as proteins, polynucleotides such as DNA and/or RNA, metabolites such as lipids, fatty acids, sugars, nucleotides and/or amino acids, cells, viruses and/or viral particles. In some aspects, fluorescence multiplexing with encoded chromophoric polymer particles provides for sorting of multiple analytes using, e.g., flow cytometry and/or other fluorescence assisted sorting methods. In some aspects, fluorescence multiplexing with encoded chromophoric polymer particles provides for detection of multiple proteins of interest in a sample.

In some aspects, a method is provided for detecting analytes in a sample, comprising contacting a sample with a suspension of two or more pluralities of encoded chromophoric polymer particles, and measuring signals emitted from the sample and suspension. In some aspects, the sample comprises a biological fluid. In some aspects, the sample comprises blood, urine, stool, lymph, saliva, or cerebrospinal fluid. In some aspects, the sample comprises a living animal or tissue. In some aspects, the sample comprises one or more analytes that associate with biomolecules attached directly or indirectly to chromophoric polymer particles. In some aspects, the analytes comprise a polypeptide, a polynucleotide, a cell, a cellular fraction, a virus, a drug, a toxin, a carbohydrate, a sugar, a lipid, or a fatty acid.

In some aspects, the method further comprises exciting the sample and suspension with a source of electromagnetic radiation. In some aspects, the electromagnetic radiation passes through a spectral filter, a multichroic mirror, or a combination thereof. In some aspects, the peak wavelength of electromagnetic radiation exciting the sample is between about 200 nm and about 1200 nm. In some aspects, the method further comprises using a signal emitted from the sample and suspension to measure an analyte. In some aspects, the method further comprises using the spectrum of a signal emitted from the sample and suspension to measure an analyte. In some aspects, the method further comprises using the lifetime of a signal emitted from the sample and suspension to measure an analyte. In some aspects, the method further comprises using the intensity of a signal emitted from the sample and suspension to measure an analyte. In some aspects, the method further comprises separating one or more analytes from the sample. In some aspects, the method further comprises separating one or more analytes from the sample by directing particles associated with analytes to the flow cell of a flow cytometer or a microfluidic device. In some aspects, the method further comprises separating one or more analytes from the sample by attaching chromophoric polymer particles associated with analytes to a solid support.

Systems for Multiplex Analysis with Encoded Chromophoric Polymer Particles

In some aspects of the present disclosure, a system for performing multiplex analysis is provided, the system comprising a suspension of encoded chromophoric polymer particles, a sample comprising an analyte, a source of electromagnetic radiation, a detector; and a computer comprising a processor and a memory device with executable instructions stored thereon, the instructions when executed causing the processor to operate the detector to measure an emission property, store the measured emission property, and analyze the measured emission property.

In some aspects, the source of electromagnetic radiation comprises a laser, a lamp, an LED, or a combination thereof. In some aspects, the system further comprises a spectral filter, a multichroic mirror, or a combination thereof. In some aspects, the detector comprises a microscope. In some aspects, the detector comprises a camera. In some aspects, the detector comprises a flow cytometer. In some aspects, the processor can direct the analyte to the flow cell of a flow cytometer or microfluidic device based on the measured emission property.

In some aspects, the system comprises a plurality of different analytes, such as two, three, four, five, six, seven, eight, nine, ten or more different analytes. In some aspects, the system comprises a plurality of different encoded chromophoric polymer particles, such as two, three, four, five, six, seven, eight, nine, ten or more different encoded chromophoric polymer particles, e.g., attached to two, three, four, five, six, seven, eight, nine, ten or more different biomolecules that each have a binding affinity for one of the two, three, four, five, six, seven, eight, nine, ten or more different analytes.

In some aspects, the system provides a source of electromagnetic radiation configured to act as a source of excitation for the suspension and sample containing encoded chromophoric polymer particles. In some aspects, the source of electromagnetic radiation includes a laser. In some aspects, the peak wavelength emitted by the laser is between about 200 nm and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects, two or more lasers having distinct peak wavelengths can be used.

In some aspects, the source of electromagnetic radiation includes a light emitting diode (LED). An LED is a semiconducting light source. In some aspects, when an LED's anode lead has a voltage that is more positive than its cathode lead by at least the LED's forward voltage drop, current flows. Electrons are able to recombine with holes within the device, releasing energy in the form of photons. The color of the light (corresponding to the energy of the photon) is determined by the energy band gap of the semiconductor.

In some aspects, the peak wavelength emitted by an LED is between about 200 nanometers and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects, two or more LEDs having distinct peak wavelengths can be used.

In some aspects, the source of electromagnetic radiation includes a lamp, e.g., a mercury lamp, halogen lamp, metal halide lamp, or other suitable lamp. In some aspects, light emitted by the lamp is spectrally filtered by a light filtering apparatus. In some aspects, the light filtering apparatus includes a filter, e.g., a bandpass filter that only allows light wavelengths falling within a certain range to pass through it towards the suspension and sample containing chromophoric polymer particles. In some aspects, the light filtering apparatus includes a multichroic mirror that can separate light into distinct spectral components, such that it only allows light wavelengths falling within a certain range to be directed towards the suspension and sample containing encoded chromophoric polymer particles.

In some aspects, the longest wavelength that passes through a light filtering apparatus is less than 300 nm, less than 400 nm, less than 500 nm, less than 600 nm, less than 700 nm, less than 800 nm, less than 900 nm, or less than 1000 nm.

In some aspects, the shortest wavelength that passes through a light filtering apparatus is more than 200 nm, more than 300 nm, more than 400 nm, more than 500 nm, more than 600 nm, more than 700 nm, more than 800 nm, or more than 900 nm.

The systems of the present disclosure further include a detector and a computer configured to analyze the signal emitted by encoded chromophoric polymer particles.

The detector can include detectors for analyzing the signal intensity, signal-to-noise ratio, and/or other characteristics of interest. The methods described herein will be generally compatible with any known systems capable of detecting and analyzing optical information such as images.

In some aspects, the system provides a detector that detects one or more signals emitted by encoded chromophoric polymer particles. In some aspects, the detector includes a microscope, such as a confocal microscope, spinning disk microscope, multi-photon microscope, planar illumination microscope, Bessel beam microscope, differential interference contrast microscope, phase contrast microscope, epifluorescent microscope, or a combination thereof. In some aspects, the detector includes a camera, such as a charge-coupled device camera, that can integrate the signal into an image on a digital chip. In some aspects, the detector includes a photomultiplier tube. In some aspects, the detector includes a flow cytometer.

In some aspects, detectors and sources of electromagnetic radiation are optimized for performing multiplex analysis. In some aspects, the detectors and sources of electromagnetic radiation are configured to excite encoded chromophoric polymer particles and detect emitted signal (e.g., optically detectable codes) rapidly. In some aspects, the detectors and sources of electromagnetic radiation are configured to excite encoded chromophoric polymer particles and detect one or more emitted signals in less than 1 nanosecond, less than 10 nanoseconds, less than 100 nanoseconds, less than 1 microsecond, less than 10 microseconds, less than 100 microseconds, less than 1 millisecond, less than 10 milliseconds, less than 100 milliseconds, less than 1 second, less than 10 seconds, or less than 100 seconds. In some aspects, the detectors and sources of electromagnetic radiation are configured to excite encoded chromophoric polymer particles and detect two or more emitted signals simultaneously.

In some aspects, the system provides a computer comprising a processor and a memory device with executable instructions stored thereon. Examples of a processor include, but are not limited to, a personal computing device that stores information acquired by a detector, and software running on the personal computing device that processes the information. In other aspects, an information processor or component thereof can be embedded in a detector, such as in a chip embedded in a camera that stores optical information acquired by the camera either permanently or temporarily. In other aspects, an information processor and a detector can be components of a fully integrated device that both acquires and stores optical information emitted by chromophoric polymer particles.

In some aspects, the system provides a computer-readable storage medium for acquiring, storing, and analyzing a signal. The computer-readable storage medium has stored thereon instructions that, when executed by one or more processors of a computer, cause the computer to: operate the detector to acquire an optical signal, store the signal, and analyze the signal. In some aspects, the computer analyzes the emission spectrum, emission lifetime, and/or emission intensity of the signal. In some aspects, the computer analyzes the signal to detect and/or determine the concentration of a target analyte of interest in a sample. In some aspects, the computer analyzes signals emitted by one or more pluralities of encoded chromophoric polymer particles. In some aspects, the computer analyzes emission spectra, emission lifetimes, and/or emission intensities of signals emitted by one or more pluralities of encoded chromophoric polymer particles. In some aspects, the computer analyzes signals emitted by one or more pluralities of encoded chromophoric polymer particles to detect and/or determine the concentration of multiple analytes in a sample.

In some aspects, the system provides a computer comprising a processor that controls the directed transport of analytes based on emission properties measured from a sample. In some aspects, the processor can direct analytes to the flow cell of a flow cytometer or a microfluidic device based on the measured emission properties. In some aspects, the processor analyzes the emission spectra, emission lifetimes, and/or emission intensities of one or more signals emitted by one or more pluralities of encoded chromophoric polymer particles to control the directed transport of analytes, such as to the flow cell of a flow cytometer or a microfluidic device.

In some aspects, a computer can be used to perform the methods described herein. In various aspects, a computer can be used to implement any of the systems or methods illustrated and described above. In some aspect, a computer can include a processor that communicates with a number of peripheral subsystems via a bus subsystem. These peripheral subsystems can include a storage subsystem, comprising a memory subsystem and a file storage subsystem, user interface input devices, user interface output devices, and a network interface subsystem.

In some aspects, a bus subsystem provides a mechanism for enabling the various components and subsystems of the computer to communicate with each other as intended. The bus subsystem can include a single bus or multiple busses.

In some aspects, a network interface subsystem provides an interface to other computers and networks. The network interface subsystem can serve as an interface for receiving data from and transmitting data to other systems from a computer. For example, a network interface subsystem can enable a computer to connect to the Internet and facilitate communications using the Internet.

In some aspect, the computer includes user interface input devices such as a keyboard, pointing devices such as a mouse, trackball, touchpad, or graphics tablet, a scanner, a barcode scanner, a touch screen incorporated into the display, audio input devices such as voice recognition systems, microphones, and other types of input devices. In general, use of the term "input device" is intended to include all possible types of devices and mechanisms for inputting information to a computer.

In some aspect, the computer includes user interface output devices such as a display subsystem, a printer, a fax machine, or non-visual displays such as audio output devices, etc. The display subsystem can be a cathode ray tube (CRT), a flat-panel device such as a liquid crystal display (LCD), or a projection device. In general, use of the term "output device" is intended to include all possible types of devices and mechanisms for outputting information from a computer.

In some aspects, the computer includes a storage subsystem that provides a computer-readable storage medium for storing the basic programming and data constructs. In some aspects, the storage subsystem stores software (programs, code modules, instructions) that when executed by a processor provides the functionality of the methods and systems described herein. These software modules or instructions can be executed by one or more processors. A storage subsystem can also provide a repository for storing data used in accordance with the present disclosure. The storage subsystem can include a memory subsystem and a file/disk storage subsystem.

In some aspects, the computer includes a memory subsystem that can include a number of memories including a main random access memory (RAM) for storage of instructions and data during program execution and a read only memory (ROM) in which fixed instructions are stored. A file storage subsystem provides a non-transitory persistent (non-volatile) storage for program and data files, and can include a hard disk drive, a floppy disk drive along with associated removable media, a Compact Disk Read Only Memory (CD-ROM) drive, an optical drive, removable media cartridges, and other like storage media.

The computer can be of various types including a personal computer, a portable computer, a workstation, a network computer, a mainframe, a kiosk, a server or any other data processing system. Due to the ever-changing nature of computers and networks, the description of computer contained herein is intended only as a specific example for purposes of illustrating the aspect of the computer. Many other configurations having more or fewer components than the system described herein are possible.

All publications, patents, and patent applications mentioned in this specification are herein incorporated by reference to the same extent as if each individual publication, patent, or patent application is specifically and individually indicated to be incorporated by reference.

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof may be suggested to persons skilled in the art and are included within the spirit and purview of this application and scope of the appended claims. Numerous different combinations of aspects described herein are possible, and such combinations are considered part of the present disclosure.

As used herein A and/or B encompasses one or more of A or B, and combinations thereof such as A and B.

All features discussed in connection with any aspect or aspect herein can be readily adapted for use in other aspects and aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Unless otherwise specified, the presently described methods and processes can be performed in any order. For example, a method describing steps (a), (b), and (c) can be performed with step (a) first, followed by step (b), and then step (c). Or, the method can be performed in a different order such as, for example, with step (b) first followed by step (c) and then step (a). Furthermore, those steps can be performed simultaneously or separately unless otherwise specified with particularity.

The particulars shown herein are by way of example and for purposes of illustrative discussion of the preferred aspects of the present disclosure only and are presented in the cause of providing what is believed to be the most useful and readily understood description of the principles and conceptual aspects of various aspects of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

While preferred aspects of the present disclosure have been shown and described herein, it is to be understood that the disclosure is not limited to the particular aspects of the disclosure described, as variations of the particular aspects can be made and still fall within the scope of the appended claims. It is also to be understood that the terminology employed is for the purpose of describing particular aspects of the disclosure, and is not intended to be limiting. Instead, the scope of the present disclosure is established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the disclosure provided herein.

All features discussed in connection with an aspect or aspect herein can be readily adapted for use in other aspects and aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

EXAMPLES

The following examples are included to further describe some aspects of the present disclosure, and should not be used to limit the scope of the invention.

Example 1

Analysis of Strategies to Overcome Poisson Statistics of Fluorophore Distribution This example describes analysis verifying strategies to overcome Poisson statistics of fluorophore distribution in encoded chromophoric polymer particles.

Figure 7B:
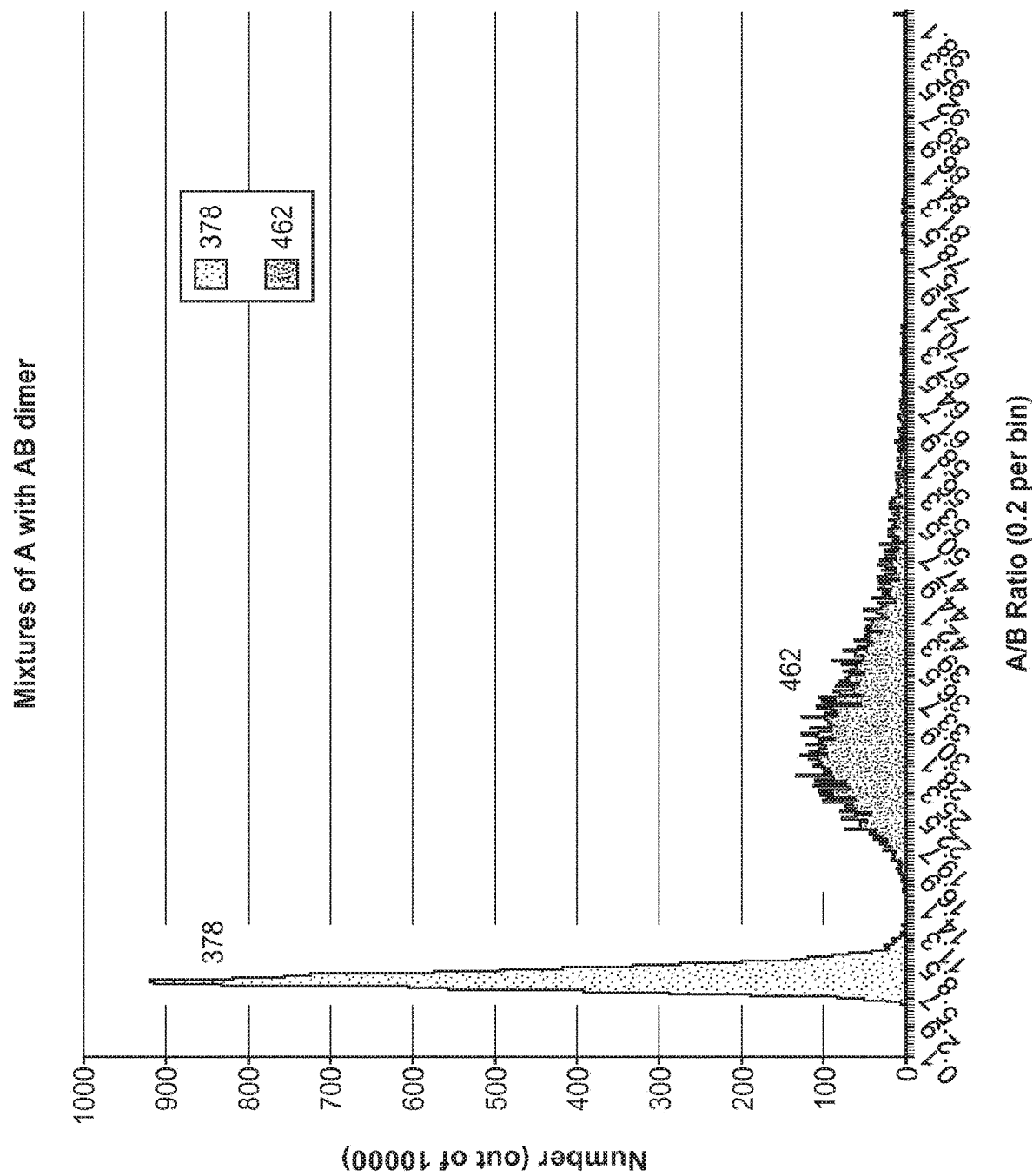

FIGS. 7A and 7B show population distributions of fluorophore A in encoded chromophoric polymer particles, where the encoded chromophoric polymer particles are made from monomer A and dimer AB. This strategy is employed to overcome Poisson statistics of fluorophore distribution in encoded chromophoric polymer particles preparation. Each series in these histograms is labeled with the expected number of A monomers in the encoded chromophoric polymer particles. The expected number of AB dimers in each encoded chromophoric polymer particles is 0.5×(492−[number of A monomers]). Five distributions are shown in FIG. 7A; two distributions are shown in FIG. 7B, and distribution for A=378 in both histograms. Each distribution is performed with 10000 encoded chromophoric polymer particles. In addition, there are distributions with pure dimer (A/B=1) and pure monomer (A/B=∞). The distributions formed from mixtures of B monomer with AB dimer are similar to those from A monomer with AB dimer, just reflected across A/B=1 (FIG. 7A). Therefore, distinct distributions include six mixtures of A with AB, six mixtures of B with AB, pure A, pure AB and pure B for 15 possible intensity levels. Analysis with mixtures of monomer A and monomer B yielded wide distributions as compared to analysis with mixtures of monomer A and dimer AB. Using the heterodimer results in narrow distributions for mixtures with approximately equal amounts of A and B and so more possible levels can be obtained with the strategy. In this way more intensity levels can be generated when using other short polymers of fixed composition (ABBB, AAAB, ABBBBBBB, etc.).

Example 2

Two-Color Encoded Lanthanide Chromophoric Polymer Particles

This example describes some aspects of the synthesis, properties, and uses of several two-color encoded chromophoric polymer particles composed of a blue-emissive polymer; a red Eu complex or an orange Sm complex; and a functional, non-emissive polymer at different mass ratios.

The encoded chromophoric polymer particles are prepared by physical blending. All polymers and lanthanide complexes are dissolved in THF to make 1 mg/mL stock solutions. The stock solutions of lanthanide complexes and polymers are mixed in different mass ratios to provide a set of encoded chromophoric polymer particles. Usually the highest injected concentration of the composite is around 0.1 mg/mL, and totally 2×1 mL mixed THF solution were injected into 10 mL DI $H_2O$ under sonication.

The chemical structures of Eu- and Sm-based lanthanide complexes, functional polymer PS-PEG-COOH, and general emissive polymers PFO and PFO-COOH that were used to produce these two-color encoded chromophoric polymer particles are given below:

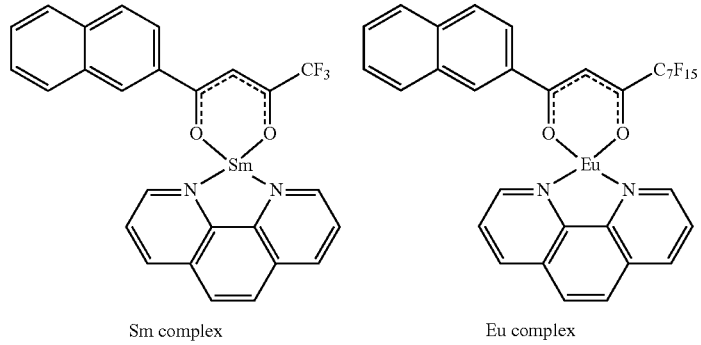

Sm complex                Eu complex

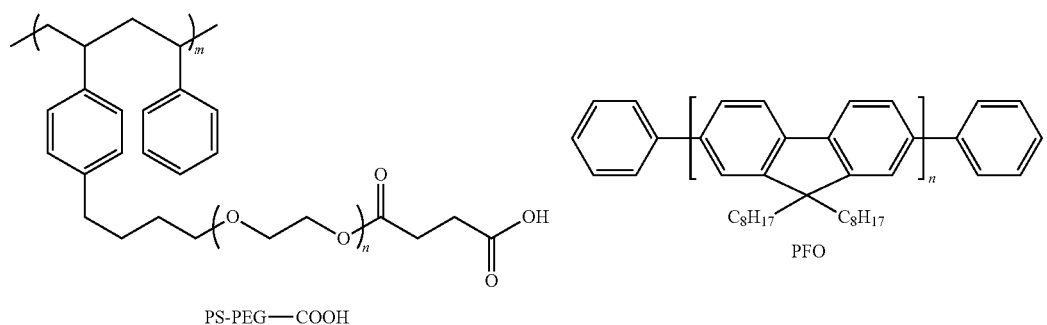

PS-PEG—COOH                    PFO

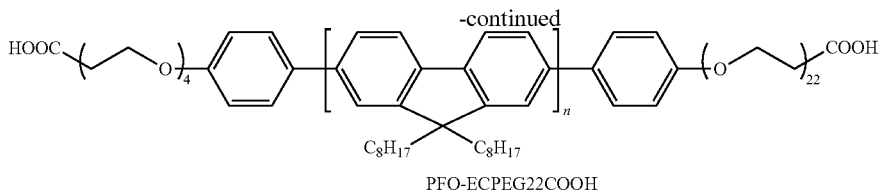

PFO-ECPEG22COOH

Example lanthanide complexes include Eu complexes and Sm complexes. The polymers included polyfluorene polymers with and without functional group endcaps. These functional group endcaps can include PEG$_{22}$COOH, polystyrene polymer conjugated with polyethylene glycol having a COOH terminus (PS-PEG-COOH), and polystyrene (PS). The length of the various polymers can be denominated by m and n as shown above. The number of repeating units, m and n, can be any desired length. For example, in poly-(9-vinyl carbazole) (PVK), n can range from 5 to 10,000; in PS-PEG-COOH, m can range from 10 to1000, and n can range from 1 to 100; and in polystyrene (PS), n can range from 5 to 10,000. In this example, PVK has an average MW=75,000, polydispersity=2. PS-PEG-COOH has a main chain MW=8,500, graft chain MW=1,200, and total chain MW=21,700, polydispersity=1.25. Polystyrene has an average MW=41,000.

The synthesis of polymer PFO-ECPEG$_{22}$COOH is given below:

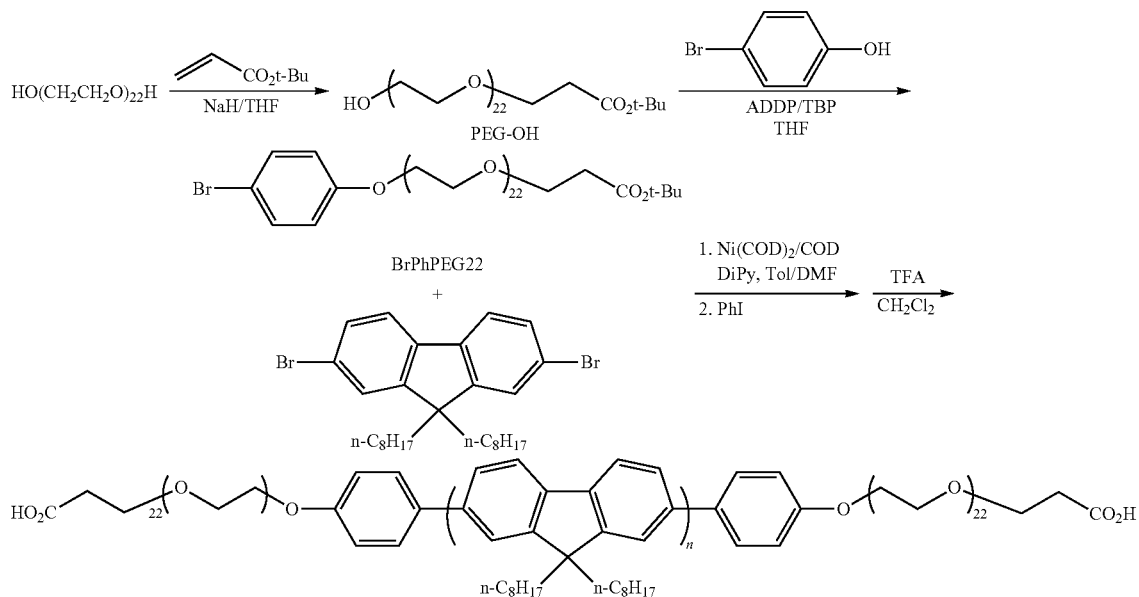

*ADDP: 1,1'-(Azodicarbonyl)dipiperidine; TBP: Tri-n-butylphosphine

Synthesis of monomer PEG-OH: NaH (dry, 95%, 50 mg, 2.1 mmol) was added to a solution of poly(ethylene glycol) (average MW=1000) (50.0 g, 50 mmol) in anhydrous THF (50.0 mL). After the reaction mixture turned clear, tert-butyl acrylate (7.3 mL, 50.0 mmol) was added. The resulting solution was stirred for 20 h at room temperature. The reaction mixture was then poured into saturated brine solution, and extracted with ethyl acetate. The combined organic extracts were dried over anhydrous Na$_2$SO$_4$. After fully removal of the solvent, the desired product was obtained as waxy solid (45.0 g, 80%) without further purification. Proton nuclear magnetic resonance spectroscopy (1H NMR) (CDCl$_3$, 300 MHz, ppm): 3.74-3.60 (m, 80H), 2.50 (t, J=6.6 Hz, 2H), 1.45 (s, 9H).

Synthesis of monomer BrPhPEG$_{22}$: Under nitrogen atmosphere, the mixture of 4-bromophenol (0.86 g, 5.0 mmol), PEG-OH (4.5 g, 4.0 mmol), and 1,1'-(azodicarbonyl)dipiperidine (1.26 g, 5.0 mmol) was dissolved in dry THF (30 mL), and liquid tri-n-butylphosphine (1.3 mL, 5.0 mmol) was added dropwise to the solution at 0° C. After 15 min., the reaction mixture was brought to room temperature and stirring was continued for 2 days. A white solid precipitate was filtered and washed with THF. After evaporation of the solvent from the collected filtrates, the product was then purified by column chromatography using gradient eluents (ethyl acetate to ethyl acetate/methanol mixture) and obtained as clear viscous liquid (2.82 g, 55%). 1H NMR (CDCl$_3$, 300 MHz, ppm): 7.36 (d, J=9.0 Hz, 2H), 6.80 (d, J=9.0 Hz, 2H), 4.11-4.08 (m, 2H), 3.86-3.83 (m, 2H), 3.73-3.62 (m, 80H), 2.50 (t, J=6.3 Hz, 2H), 1.45 (s, 9H).

Synthesis of polymer PFO-ECPEG$_{22}$COOH: bis(1,5-cyclooctadiene)-nickel(0) (316 mg, 1.15 mmol), 2,2-bipyridyl (180 mg, 1.15 mmol), 1,5-cyclooctadiene (125 mg, 1.15 mmol), and 3 mL of dimethylformamide (DMF)/toluene (v/v, 1:1) into a 25 mL flask was placed. The reaction mixture was heated to 60° C. for 0.5 h under nitrogen. A mixture of 9,9-dioctyl-2,7-dibromofluorene (274 mg, 0.5 mmol) and BrPhPEG$_{22}$ (25.6 mg, 0.02 mmol) dissolved in 3 mL of dimethylformamide (DMF)/toluene (v/v, 1:1) was added under nitrogen to the above DMF/toluene solution and the polymerization was maintained at 60° C. for 3 days in the dark. A few drops of iodobenzene were added and the reaction continued for 12 h. The reaction mixture was poured into stirred methanol to precipitate plenty of solids. The solid was collected by filtration and washed with methanol and water. The residue was dissolved in chloroform and de-doped by stirring in ammonium hydroxide solution for 24 h. The organic layer was isolated, and the concentrated solution was added dropwise into methanol to precipitate the polymer. The solids were isolated by filtration, washed with methanol again, and dried in vacuum oven. Afterwards the resultant polymer was dissolved in dichloromethane, and 1 mL of trifluoroacetate acid was added. The reaction mixture was stirred overnight at room temperature. The reaction solution was washed with water and brine, and the concentrated solution was added dropwise into methanol to precipitate the polymer. The solids were isolated by filtration, washed with methanol again, and dried in vacuum oven to get the desired polymer (160 mg, 70%). 1H NMR (CDCl$_3$, 300 MHz, ppm): 7.92-7.80 (m, 2H), 7.76-7.60 (m, 4H), 3.71-3.62 (m, 3.12H), 2.23-2.00 (b, 4H), 1.29-1.02 (m, 24H), 0.82 (t, J=6.3 Hz, 6H). GPC (THF, polystyrene standards): Mn=22.7×103 g/mol, PDI=1.62.

Figure 8A:
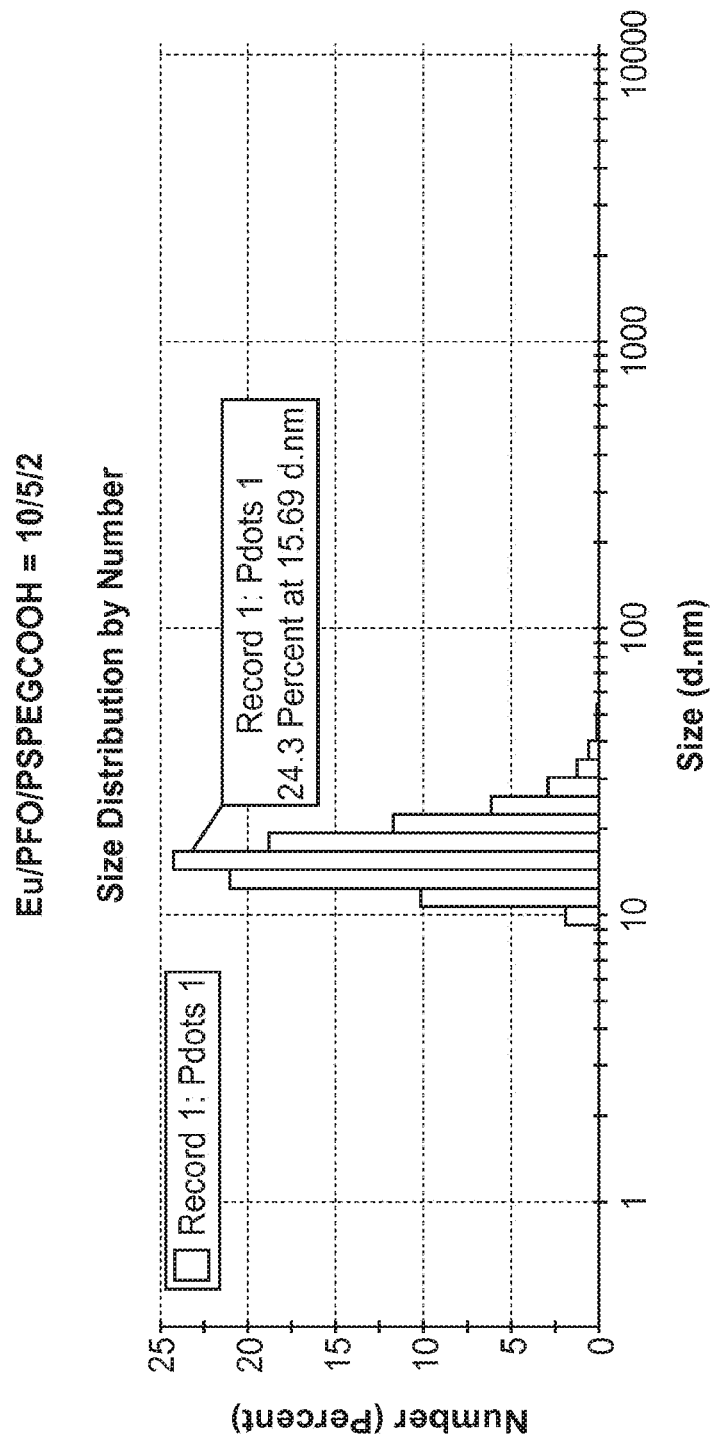
FIG. 8A shows the size distribution Eu/PFO/PS-PEG-COOH (10/5/2 mass ratio).
Figure 8B:
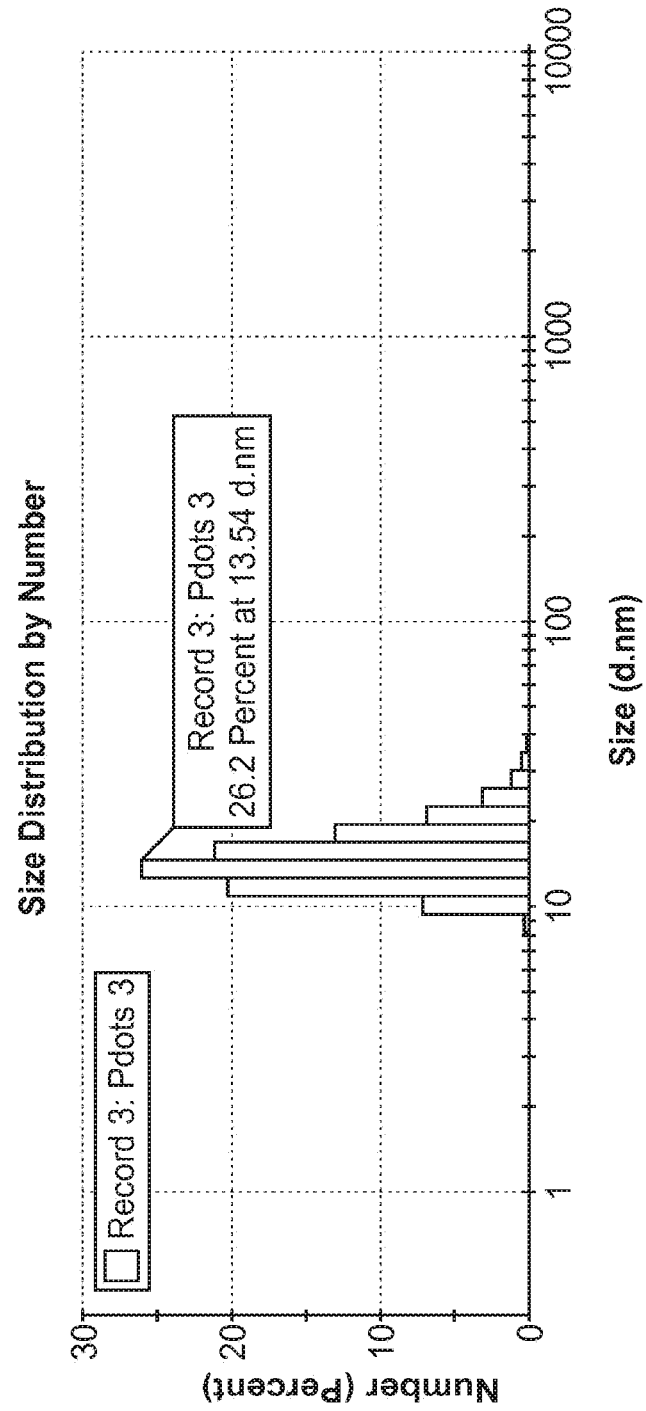
FIG. 8B shows the size distribution of Eu/PFO-ECPEG22COOH/PS-PEG-COOH (10/5/2 mass ratio).

FIG. 8A shows the size distribution measured by dynamic light scattering (DLS) of two-color encoded chromophoric polymer particles with the mass ratio as Eu/PFO/PS-PEG-COOH=10/5/2, and gives the mean size of these encoded chromophoric polymer particles to be approximately 15.7 nanometers, FIG. 8B shows the size distribution measured by DLS of two-color encoded chromophoric polymer particles with the mass ratio as Eu/PFO-ECPEG$_{22}$COOH)/PS-PEG-COOH=10/5/2 and gives the mean size around 13.5 nanometers.

Figure 9A:
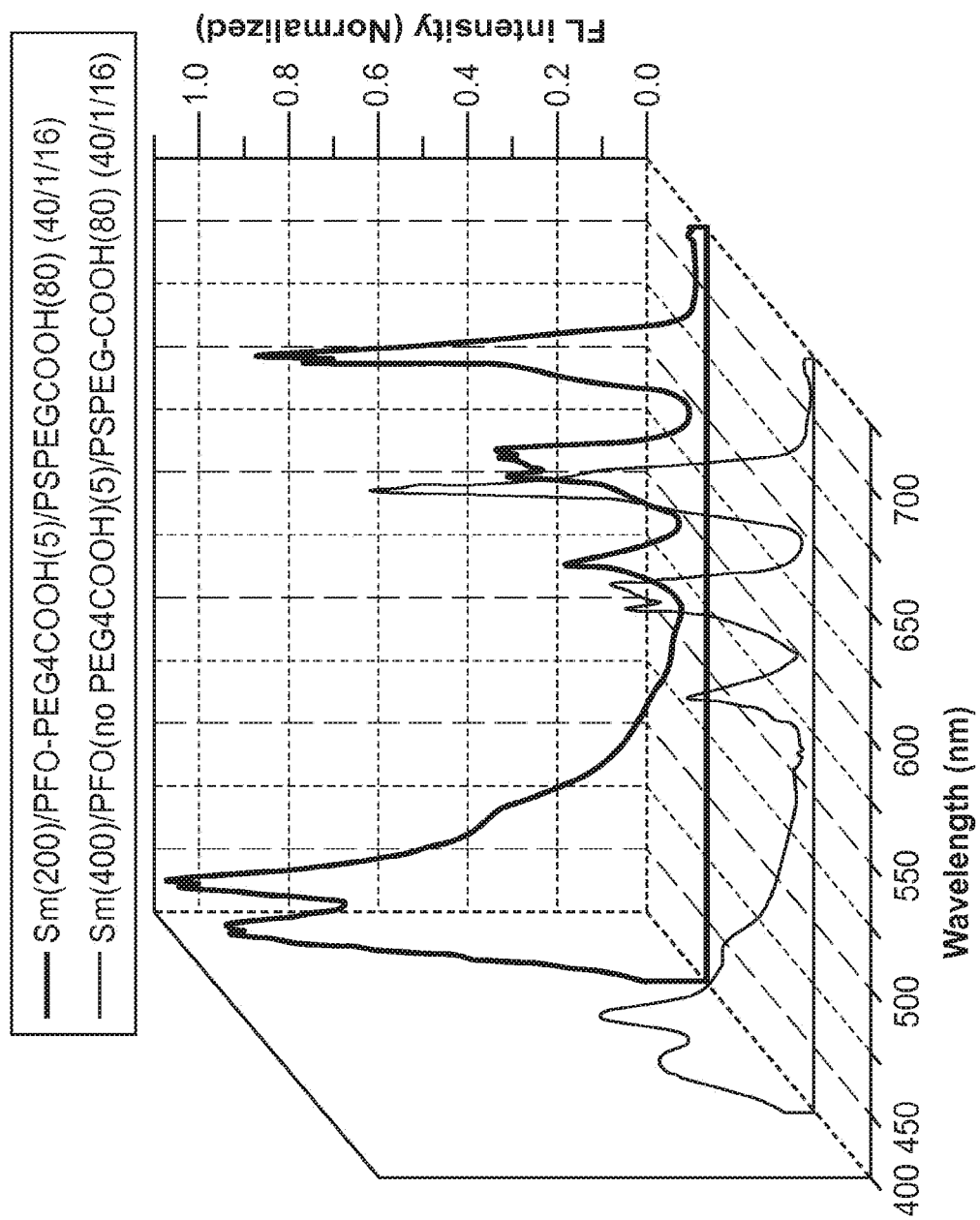
FIG. 9A shows the emission spectra of two-color encoded chromophoric polymer particles: Sm/PFO/PS-PEG-COOH (40/1/16 mass ratio) and Sm/PFO-ECPEG22COOH/PS-PEG-COOH (40/1/16 mass ratio).

FIG. 9A shows the emission spectra of two-color encoded chromophoric polymer particles: Sm/PFO/PS-PEG-COOH (40/1/16 mass ratio) and Sm/PFO-ECPEG$_{22}$COOH/PS-PEG-COOH (40/1/16 mass ratio). From the spectra, it is known that the different emission peaks from the PFO and Sm complexes can be clearly separated.

Figure 9B:
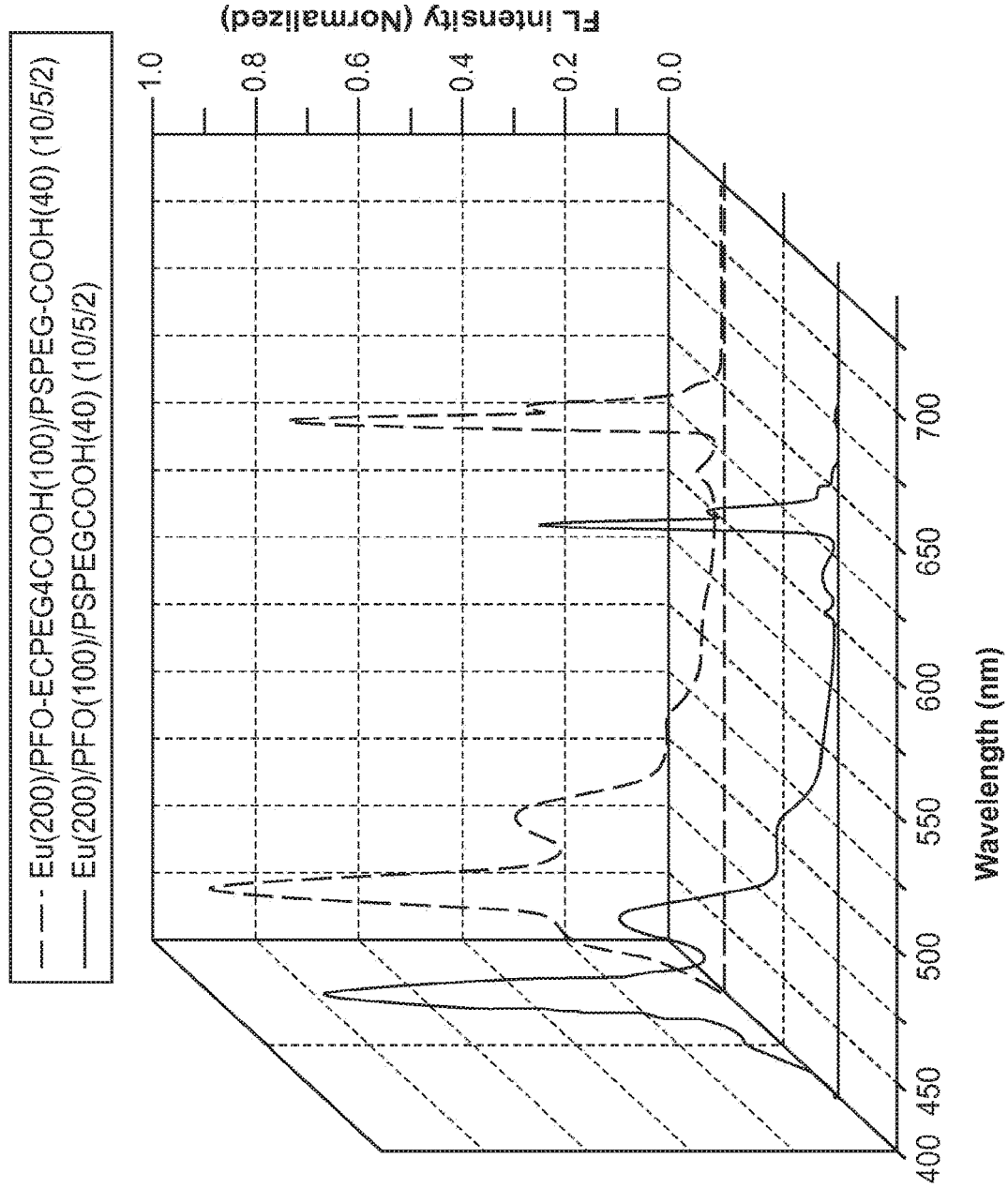
FIG. 9B shows the emission spectra of two-color encoded chromophoric polymer particles: Eu/PFO/PS-PEG-COOH (10/5/2 mass ratio) and Eu/PFO-ECPEG22COOH/PS-PEG-COOH (10/5/2 mass ratio).

FIG. 9B shows the emission spectra of two-color encoded chromophoric particles: Eu/PFO/PS-PEG-COOH (10/5/2 mass ratio) and Eu/PFO-ECPEG$_{22}$COOH/PS-PEG-COOH (10/5/2 mass ratio). From the spectra, it known that the different emission peaks from the PFO and Eu complexes can be clearly separated.

Example 3

Three-Color Encoded Lanthanide Chromophoric Polymer Particles

This example describes several three-color encoded chromophoric polymer particles that include a blue-emissive polymer; a red Eu complex or an orange Sm complex; and a functional, non-emissive polymer at different mass ratios.

The encoded chromophoric polymer particles are prepared by physical blending method: all polymers and lanthanide complexes are dissolved in THF to make 1 mg/mL stock solution. The different stock solutions of lanthanide complexes and polymers are mixed at different mass ratios to provide a set of encoded chromophoric polymer particles. Usually the highest injected concentration of the composite is around 0.1 mg/mL, and totally 2×1 mL mixed THF solution were injected into 10 mL DI H$_2$O under sonication.

Figure 10A:
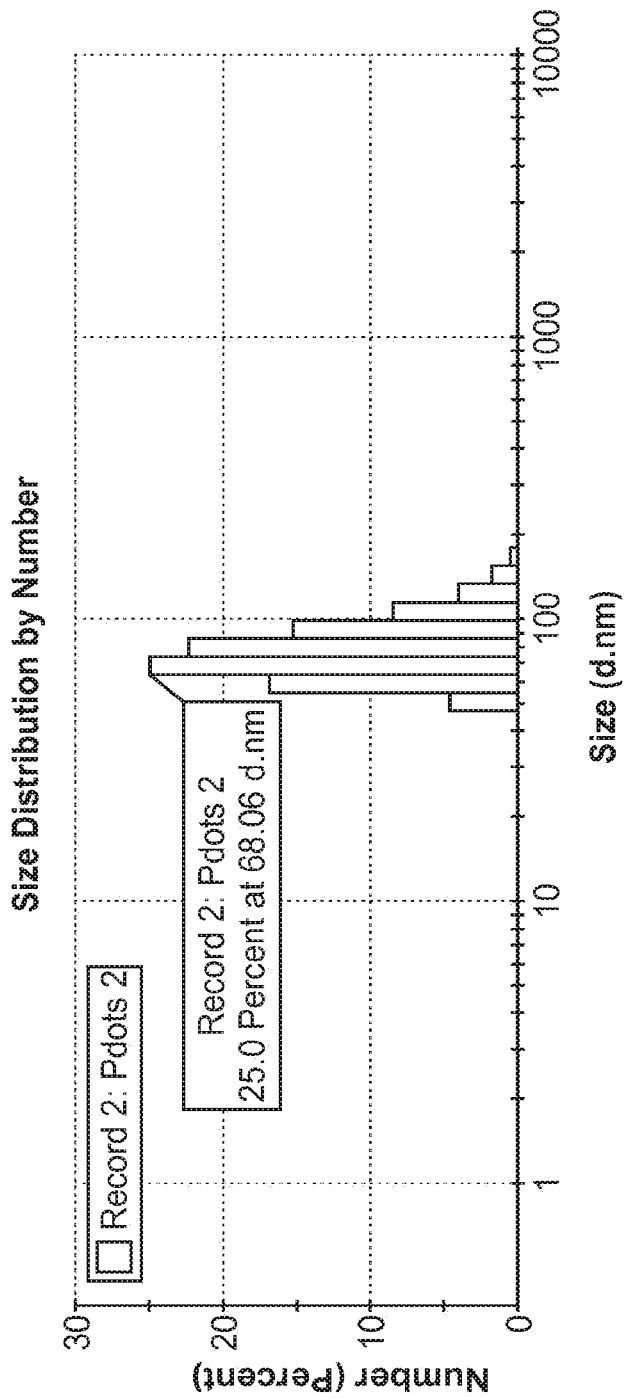
FIG. 10A shows size distribution of Sm/Eu/PFO-ECPEG22COOH/PS-PEG-COOH (40/2/1/8 mass ratio).

FIG. 10A shows the size distribution measured by DLS of three-color encoded chromophoric polymer particles with the mass ratio as Sm/Eu/PFO-ECPEG$_{22}$COOH/PS-PEG-COOH=40/2/1/8, and gives the mean size of these encoded chromophoric polymer particles to be approximately 68 nanometers.

Figure 10B:
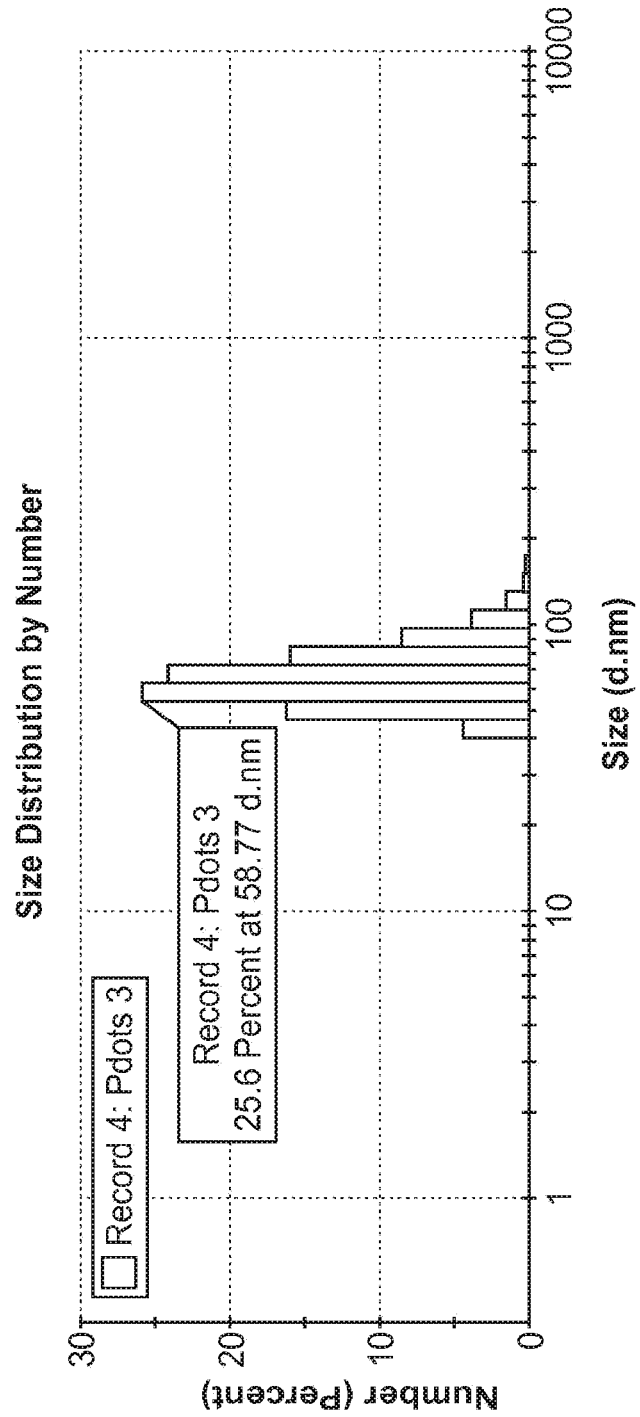
FIG. 10B shows size distribution of Sm/Eu/PFO-ECPEG22COOH/PS-PEG-COOH (80/2/1/16 mass ratio).

FIG. 10B shows the size distribution measured by DLS of three-color encoding polymer particles with the mass ratio as Sm/Eu/PFO-ECPEG$_{22}$COOH/PS-PEG-COOH=80/2/1/16 and gives the mean size of these encoded chromophoric polymer particles of approximately 59 nanometers.

Figure 11:
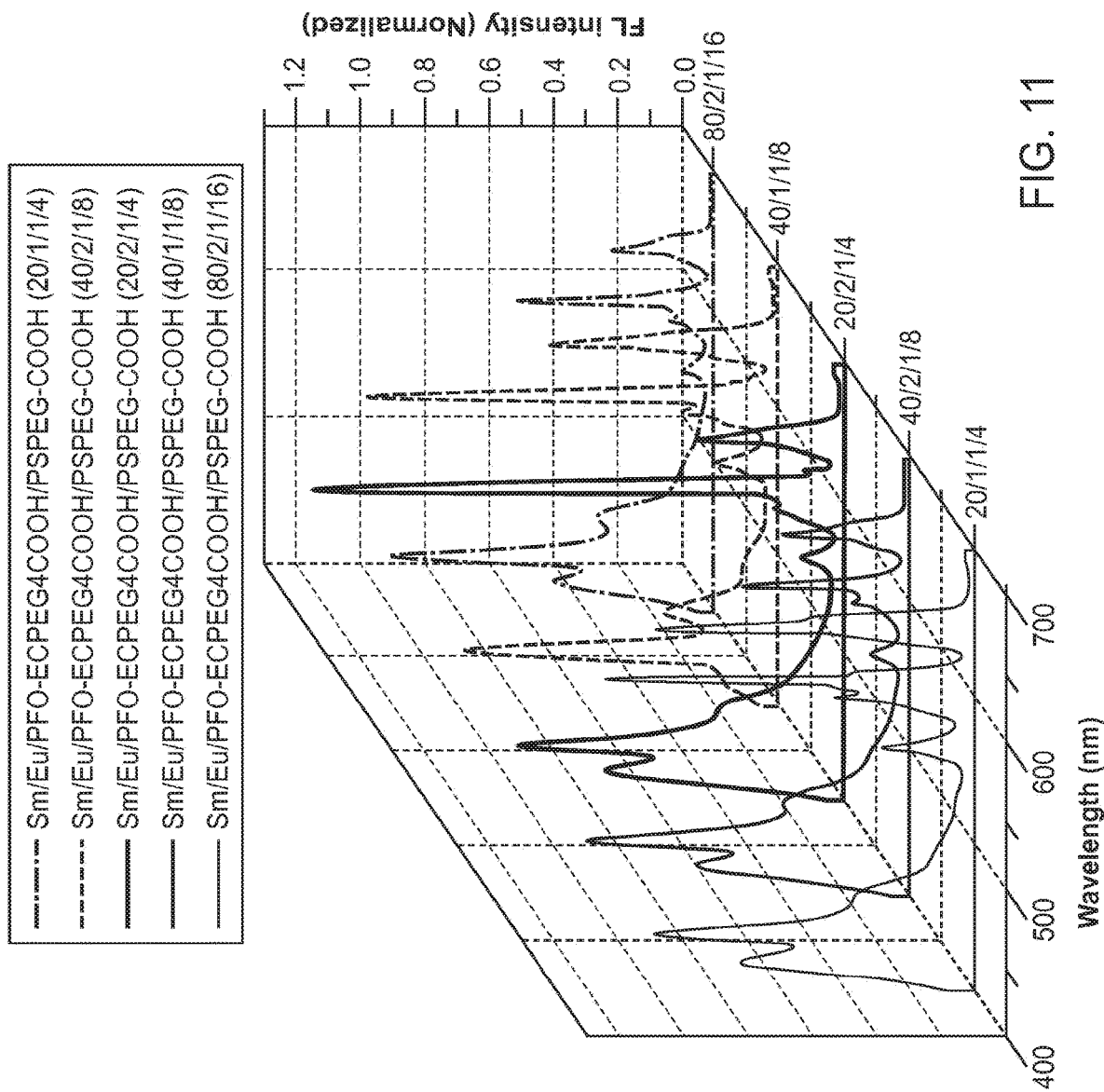
FIG. 11 shows the emission spectra of three-color encoded chromophoric polymer particles: Sm/Eu/PFO-ECPEG22COOH/PS-PEG-COOH with different mass ratios of each compound (20/1/1/4, 40/2/1/8, 20/2/1/4, 40/1/1/8, and 80/2/1/16 mass ratios).

FIG. 11 shows the emission spectra of three-color encoded chromophoric polymer particles Sm/PFO-ECPEG$_{22}$COOH/PS-PEG-COOH with five different mass ratios: 20/1/1/4, 40/2/1/8, 20/2/1/4, 40/1/1/8 and 80/2/1/16. From the spectra, we can observe that the different emission peaks from PFO-ECPEG$_{22}$COOH, Sm complex, and Eu complex can be clearly separated.

Example 4

Lanthanide-Complex-Grafted Polymer Particles with Improved Properties for Encoding This example describes the schematics and strategy that employ lanthanide-complexes grafted to the polymer matrix to prepare encoded chromophoric particles with improved quantum yield and colloidal stability.

Figure 12:
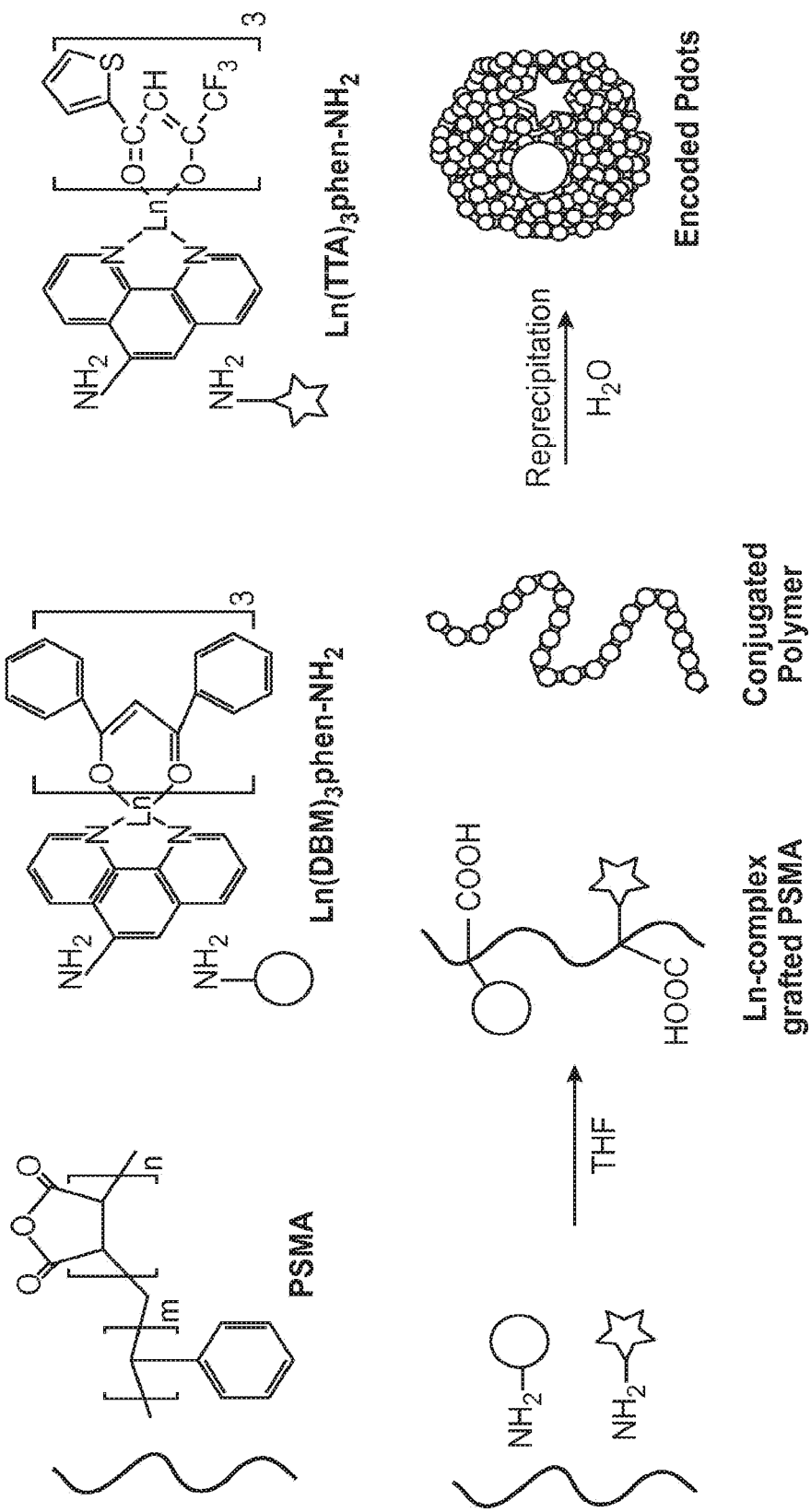
FIG. 12 is a schematic depiction of synthesis of encoded chromophoric polymer particles containing lanthanide-complex grafted polymers.

FIG. 12 shows the schematics to synthesize lanthanide-complex grafted polymer. Amine-containing lanthanide complex can react with poly(styrene-co-maleic anhydride) (PSMA) to form lanthanide-complex grafted PSMA polymers such as Ln(DBM)phen-NH-PSMA (DBM=dibenzoylmethane) and Ln(TTA)phen-NH-PSMA (TTA=thenoyltrifluoroacetone). These grafted polymers can be further blended with conjugated polymers to form encoded chromophoric polymer particles with improved colloidal stability and luminescence quantum yield. For example, we use Eu(TTA)phen-NH$_2$ to react with PSMA to form Eu(TTA) phen-grafted PSMA polymer. This polymer was further blended with PVK to prepare encoded chromophoric polymer particles by a reprecipitation method. The resulting Eu(TTA)phen-NH-PSMA/PVK encoded chromophoric polymer particles show increased quantum yield as compared to Eu(TTA)phen-NH-PSMA encoded chromophoric polymer particles alone. The Eu(TTA)phen-NH-PSMA/ PVK blended encoded chromophoric polymer particles also exhibited improved colloidal stability as compared to the encoded chromophoric polymer particles consisting of Eu(TTA)phen, PVK, and PSMA, which have the same composition but Eu(TTA)phen and PVK are not chemically linked.

Figure 13A:
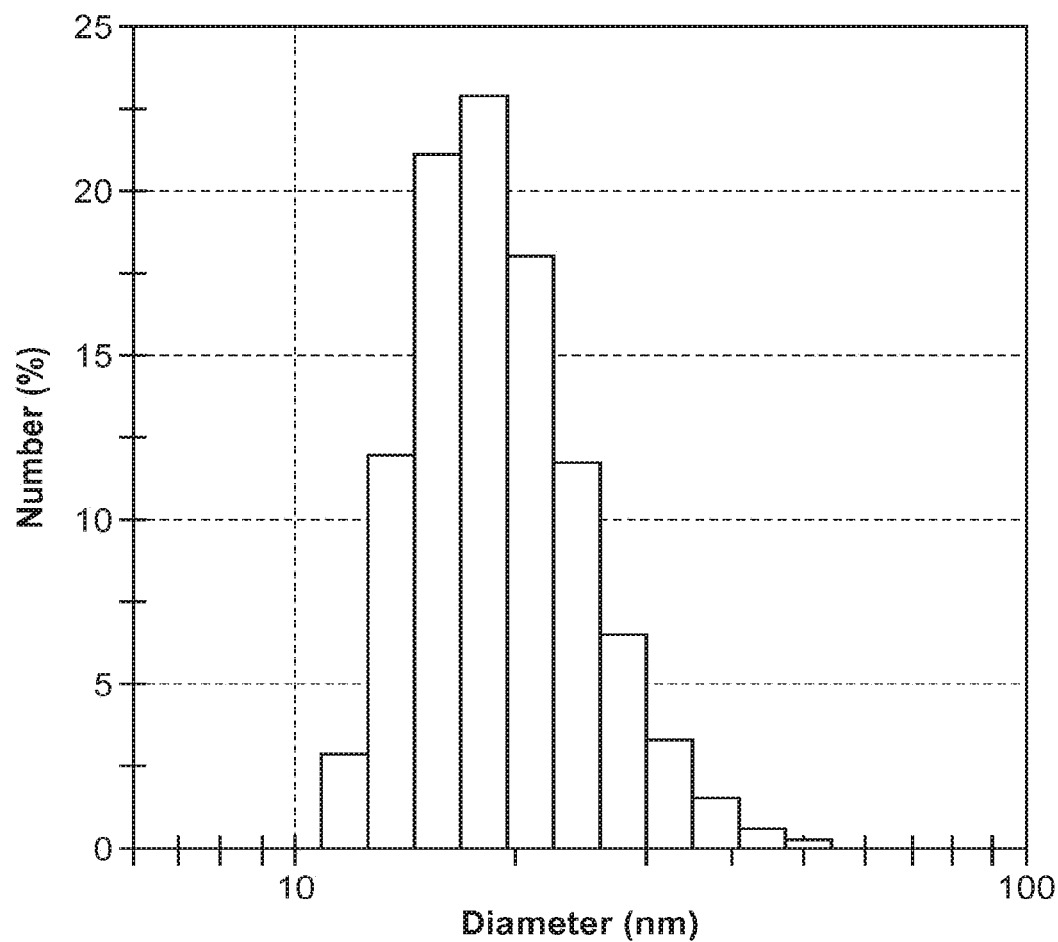
FIG. 13A shows the size distribution of polymer particles consisting of conjugated polymer PVK and Eu(TTA)phen-NH-PSMA polymer.
Figure 13B:
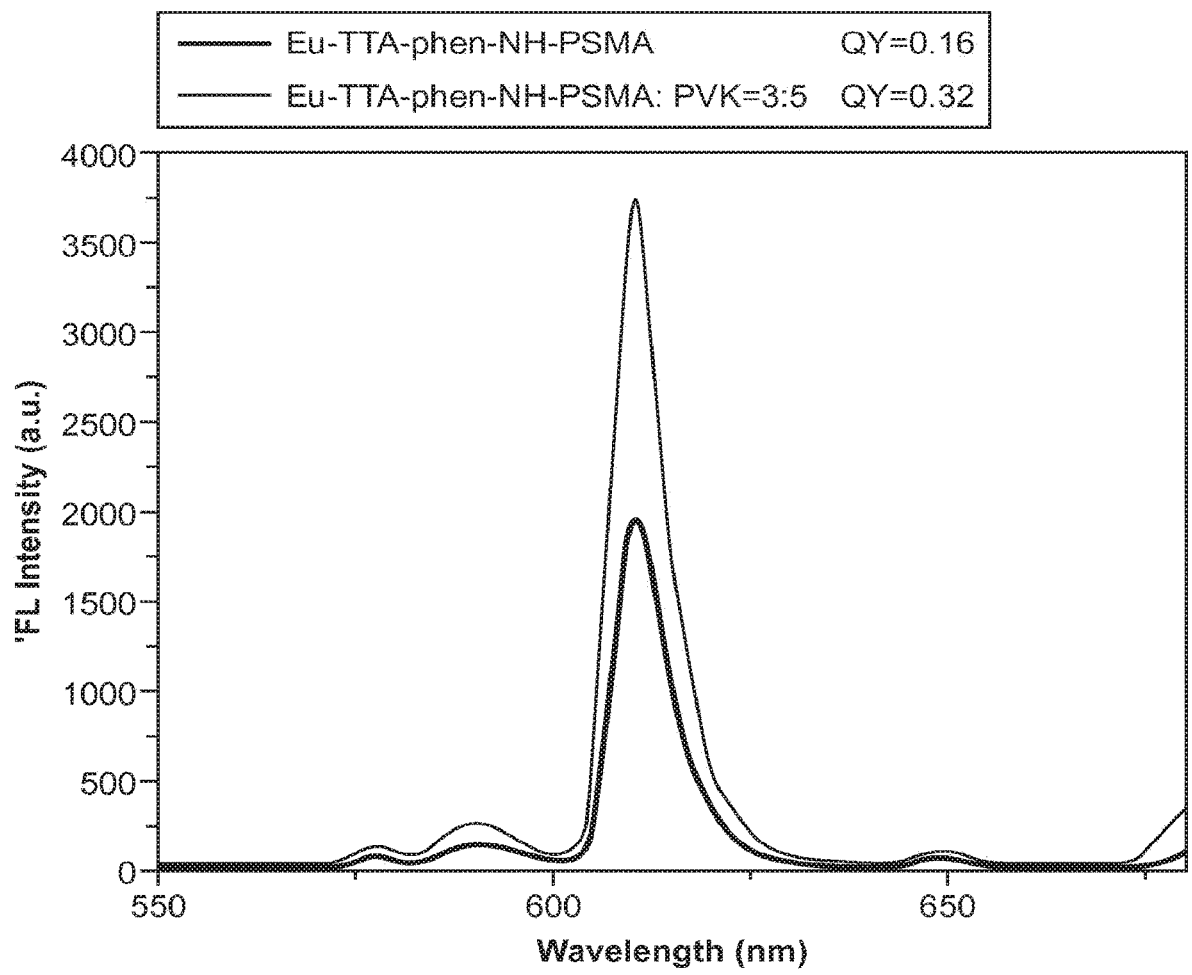
FIG. 13B shows the fluorescence spectra of Eu(TTA)phen-NH-PSMA polymer particles and blended encoded chromophoric polymer particles consisting of conjugated polymer poly-(9-vinyl carbazole) (PVK) and Eu(TTA)phen-NH-PSMA polymer.
Figure 13C:
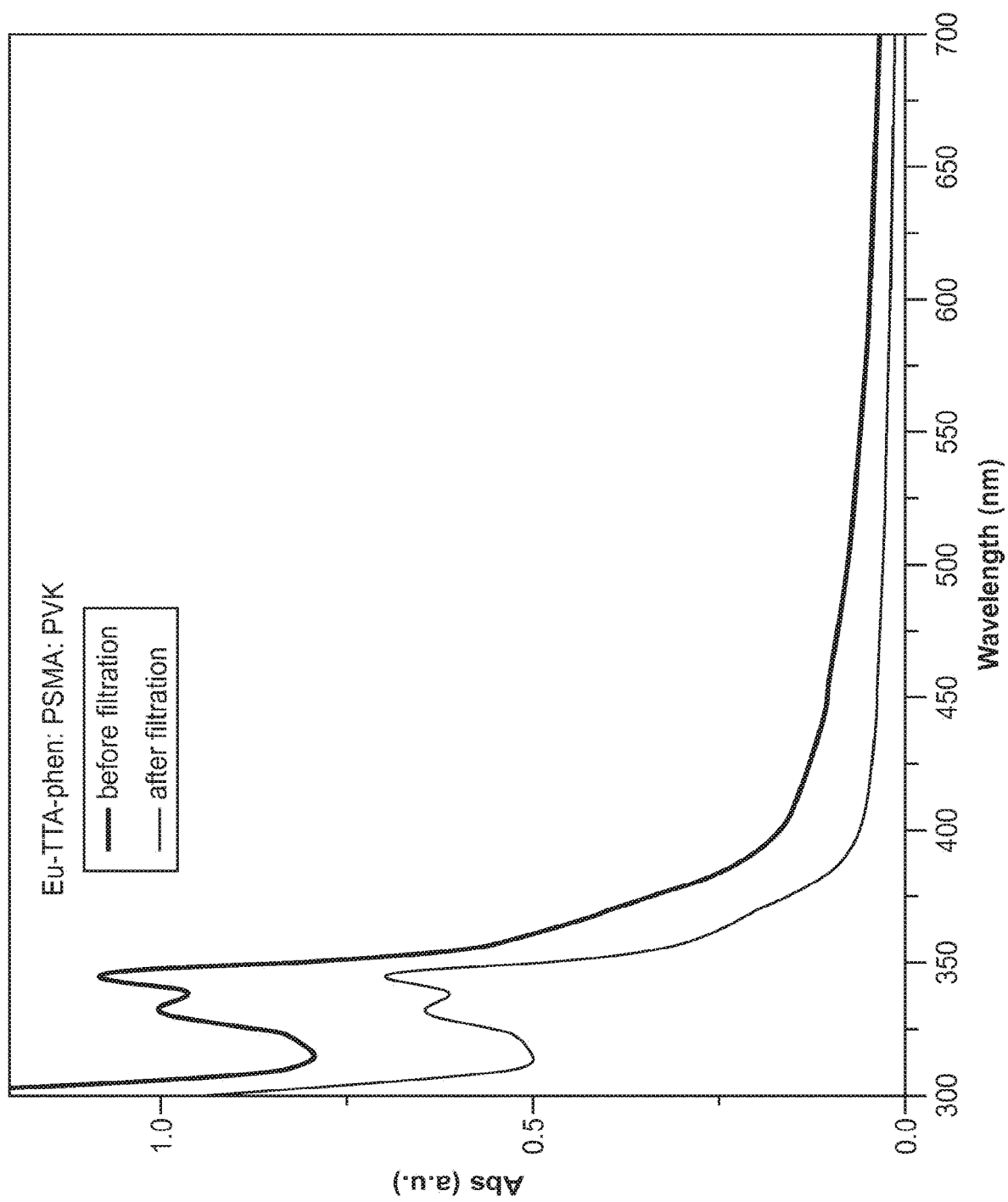
FIG. 13C shows the absorption spectra of Eu(TTA)phen doped PVK and PSMA polymer particles before and after filtration with a 220 nanometer membrane filter. PSMA was not chemically linked with Eu(TTA)phen in the polymer particles.
Figure 13D:
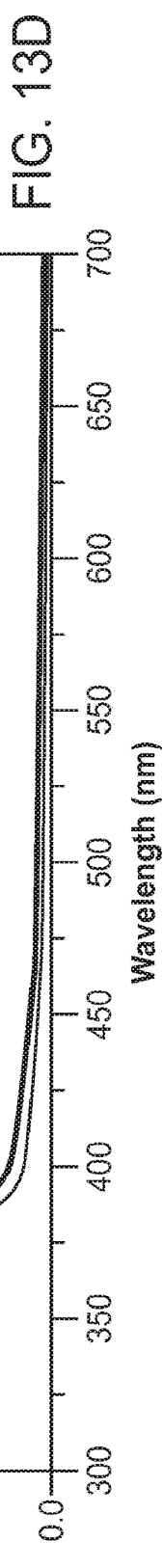
FIG. 13D shows the absorption spectra of Eu(TTA)phen doped PVK and PSMA polymer particles before and after filtration with a 220 nanometer membrane filter. PSMA was chemically linked with Eu(TTA)phen in the polymer particles.

FIG. 13A show the size distribution, measured by DLS, of encoded chromophoric polymer particles consisting of conjugated polymer PVK and Eu(TTA)phen-NH-PSMA polymer. FIG. 13B show the luminescence spectra of Eu(TTA) phen-NH-PSMA encoded chromophoric polymer particles and the blended encoded chromophoric polymer particles consisting conjugated polymer PVK and Eu(TTA)phen-NH-PSMA polymer, where the two types of encoded chromophoric polymer particles have the same absorbance. As indicated by the spectra, the luminescence quantum yield of the Eu(TTA)phen-NH-PSMA/PVK blended encoded chromophoric polymer particles was about two times higher than the pure Eu(TTA)phen-NH-PSMA encoded chromophoric polymer particles. FIG. 13C show the absorption spectra of Eu(TTA)phen doped PVK encoded chromophoric polymer particles. PSMA was also physically blended in the encoded chromophoric polymer particles, but not chemically linked with Eu(TTA)phen. The encoded chromophoric polymer particles solution was filtered by using a 220 nanometers membrane filter after two weeks. As shown in FIG. 13C, about 50 percent of the encoded chromophoric polymer particles were aggregated and removed by the filtration. FIG. 13D show the absorption spectra of Eu(TTA)phen-NH-PSMA blended PVK encoded chromophoric polymer particles. PSMA was chemically linked with Eu(TTA)phen in the encoded chromophoric polymer particles. The encoded chromophoric polymer particle solution was filtered by using a 220 nanometers membrane filter after two weeks. As indicated in FIG. 13D, the blended encoded chromophoric polymer particles were not aggregated and only a negligible amount was removed by the filtration.

Example 5

Chromophoric Polymer Particles Comprising Dye Molecules for Lifetime Encoding

This example describes preparation of dye doped encoded chromophoric polymer particles for lifetime encoding.

Dye doped encoded chromophoric polymer particles were prepared as follows: 10 mg of the semiconducting polymer, either poly(9,9-dioctylfluorenyl-2,7-diyl) end-capped with dimethyl phenyl (PFO, MW=120,000) or poly[(9,9-dioctylfluorenyl-2,7-diyl)-co-(1,4-benzo-{2,1',3}-thiadiazole)] (PFBT, MW=73,000, polydispersity=3.0) or poly[2-methoxy-5-(2-ethylhexyloxy)-1,4-(1-cyanovinylene-1,4-phenylene)] (CNPPV, MW=15,000, polydispersity=5.9), all from ADS Dyes, Inc. (Quebec, Canada) was dissolved in 10 mL THF by stirring overnight under inert atmosphere. The solution was then filtered through a 0.7 µm glass fiber filter to remove any insoluble material. Dye doped encoded chromophoric polymer particles were prepared by first mixing 200 µL of 1 mg/mL PFO, PFBT or CNPPV (in THF) with 2, 10 or 20 µL of 1 mg/mL comarin6, Tetraphenylporphyrin (TPP), or silicon 2,3-naphthalocyanine bis(trihexylsilyloxide) (NIR775) dye that had been dissolved in 5 mL THF. The mixture was injected into 10 mL of MilliQ water under sonication. The THF was removed by nitrogen stripping, and the solution was concentrated by continuous nitrogen stripping to 10 mL on a 90° C. hotplate, followed by filtration through a 0.2 µm filter. Free dye was removed by passing the solution through a Bio-Rad Econo-Pac® 10DG size exclusion column (Hercules, Calif., USA). Through this procedure, three types of dye doped encoded chromophoric polymer particles, PFO-comarin6, PFBT-TPP and CNPPV-NIR775, with three doping percentages, 1%, 5% or 10% (by mass), were made and their optical properties and lifetime were investigated. An additional 20% poly(styrene-co-maleic anhydride) (PSMA) polymer was added to the coumarin6-doped PFO encoded chromophoric polymer particles to make small size particles (approximately 20 nm).

Fluorescence lifetime data of dye doped encoded chromophoric polymer particles were obtained using a time-correlated single-photon counting instrument. PFO-coumarin6 encoded chromophoric polymer particles were excited at 375 nm, while PFBT-TPP and CNPPV-NIR encoded chromophoric polymer particles were excited at 470 nm. Both dye fluorescence decay and semiconducting polymer fluorescence decay were collected with appropriate filters. The data were analyzed using TAUFIT decay programming.

Table 1 (below) shows fluorescence emission lifetimes of the as-prepared dye doped encoded chromophoric polymer particles:

TABLE 1

Fluorescence lifetimes for different chromophoric particles doped with different dyes at three different doping percentages (1%, 5% and 10% by mass).

| | PFO + coumarin6 | | | PFBT + TPP | | | CNPPV + NIR775 | | |
|---|---|---|---|---|---|---|---|---|---|
| | \multicolumn{9}{c}{Dye % (by mass)} | | | | | | | | |
| | 1% | 5% | 10% | 1% | 5% | 10% | 1% | 5% | 10% |
| Polymer emission lifetime (nanoseconds) | 0.19 | 0.10 | 0.09 | 0.13 | 0.13 | 0.13 | 0.24 | 0.17 | 0.14 |
| Dye emission lifetime (nanoseconds) | 2.75 | 1.98 | 1.91 | 8.40 | 7.02 | 5.61 | 3.14 | 3.08 | 3.06 |

As shown in Table 1 (above), the of coumarin6 in coumarin6 doped PFO encoded chromophoric polymer particles was 2.75 nanoseconds, 1.98 nanoseconds and 1.91 nanoseconds for 1%, 5% and 10% doping (by mass), respectively. The lifetime of dye decreased as the dye doping percentage increased. The same phenomenon was also found in the TPP doped PFBT encoded chromophoric polymer particles and NIR775 doped CNPPV encoded chromophoric polymer particles. The TPP lifetimes were 8.40 nanoseconds, 7.02 nanoseconds and 5.61 nanoseconds for 1%, 5% and 10% doping percentages, respectively. The NIR775 lifetimes were 3.14 nanoseconds, 3.08 nanoseconds and 3.06 nanoseconds for 1%, 5% and 10% doping percentages, respectively. Among these three types of dye doped encoded chromophoric polymer particles, TPP shows the largest change of the lifetime versus doping percentage, showing about 30% lifetime decrease from 1% to 10% doping percentage.

The lifetimes for semiconducting polymer in the coumarin6 doped PFO and NIR775 doped CNPPV encoded chromophoric polymer particles were also found to decrease as the doping percentage increase. For example, PFO lifetimes were 0.19 nanoseconds, 0.10 nanoseconds and 0.09 nanoseconds for 1%, 5% and 10% doping percentage, respectively. CNPPV lifetimes were 0.24 nanoseconds, 0.17 nanoseconds and 0.14 nanoseconds for 1%, 5% and 10% doping percentage, respectively. The only exception was PFBT lifetime, showing an equivalent lifetime of 0.13 nanoseconds independent of the doping percentage of TPP. Fluorescence emission lifetimes of all semiconducting polymers in the dye doped encoded chromophoric polymer particles were dramatically decreased (approximately 0.09-0.24 ns) when compared to their pure (no dye doped) encoded chromophoric polymer particles (approximately 1-2 ns), which is consistent with the emission profiles shown in FIG. 15. The emission of semiconducting polymer was highly quenched by the doped dyes due to the presence of FRET taking place between semiconducting polymer and dyes.

Figure 14:
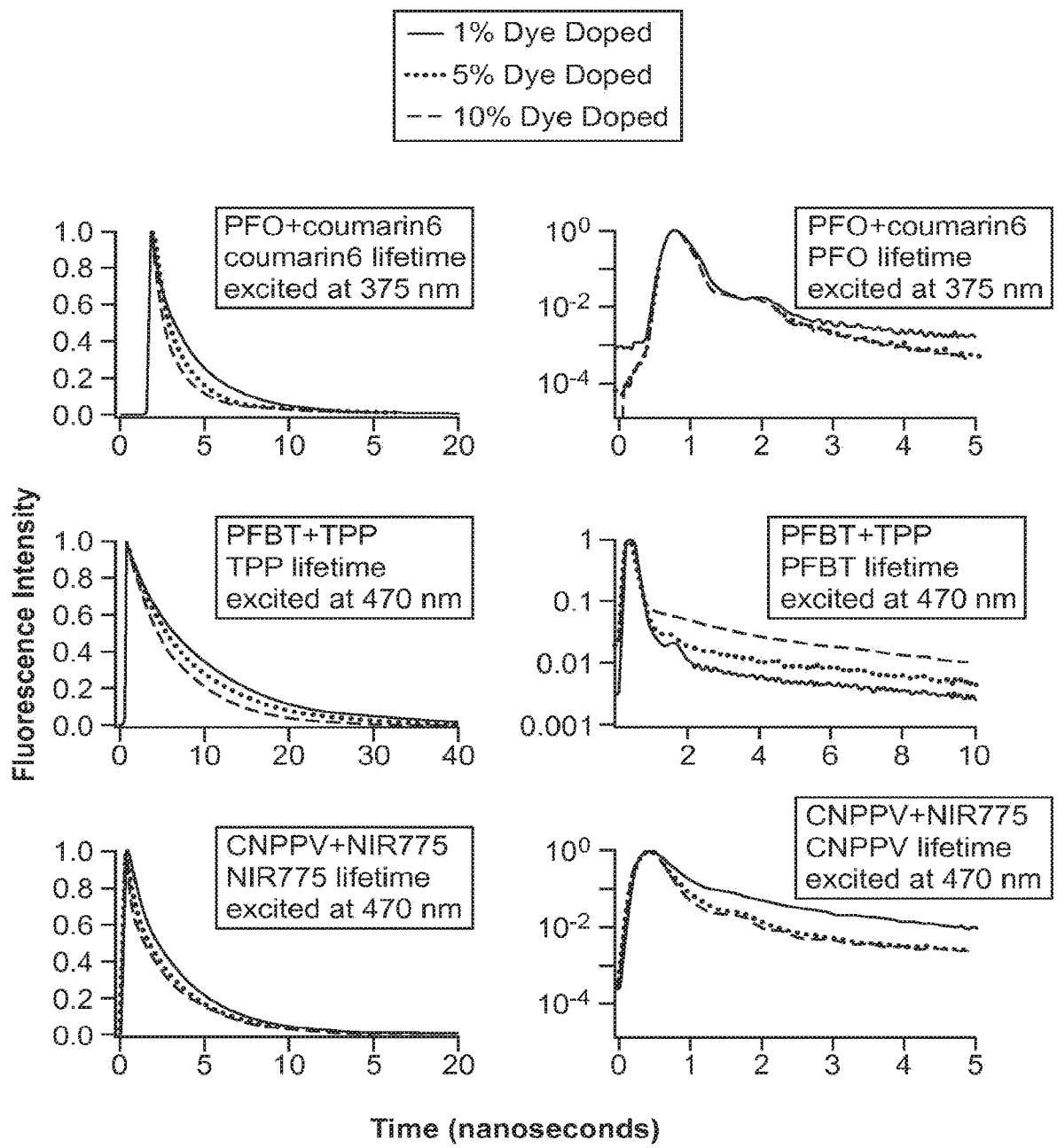
FIG. 14 shows time-decay curves of emitted fluorescence for a variety of dye doped chromophoric particles. Solid line, dotted line, and dashed line represent 1%, 5% and 10% (by mass) dye doped polymer particles, respectively.

FIG. 14 shows time-decay curves of emitted fluorescence for a variety of dye doped chromophoric particles. Solid line, dotted line, and dashed line represent 1%, 5% and 10% (by mass) dye doped encoded chromophoric polymer particles, respectively. The broad range of fluorescence emission lifetimes (from picoseconds to nanoseconds) obtained demonstrates the use of fluorescence lifetime-based coding strategies with chromophoric polymer particles, including chromophoric polymer particles doped with dye molecules. Lifetime encoding may be used alone or in combination with other encoding strategies described herein.

Figure 15:
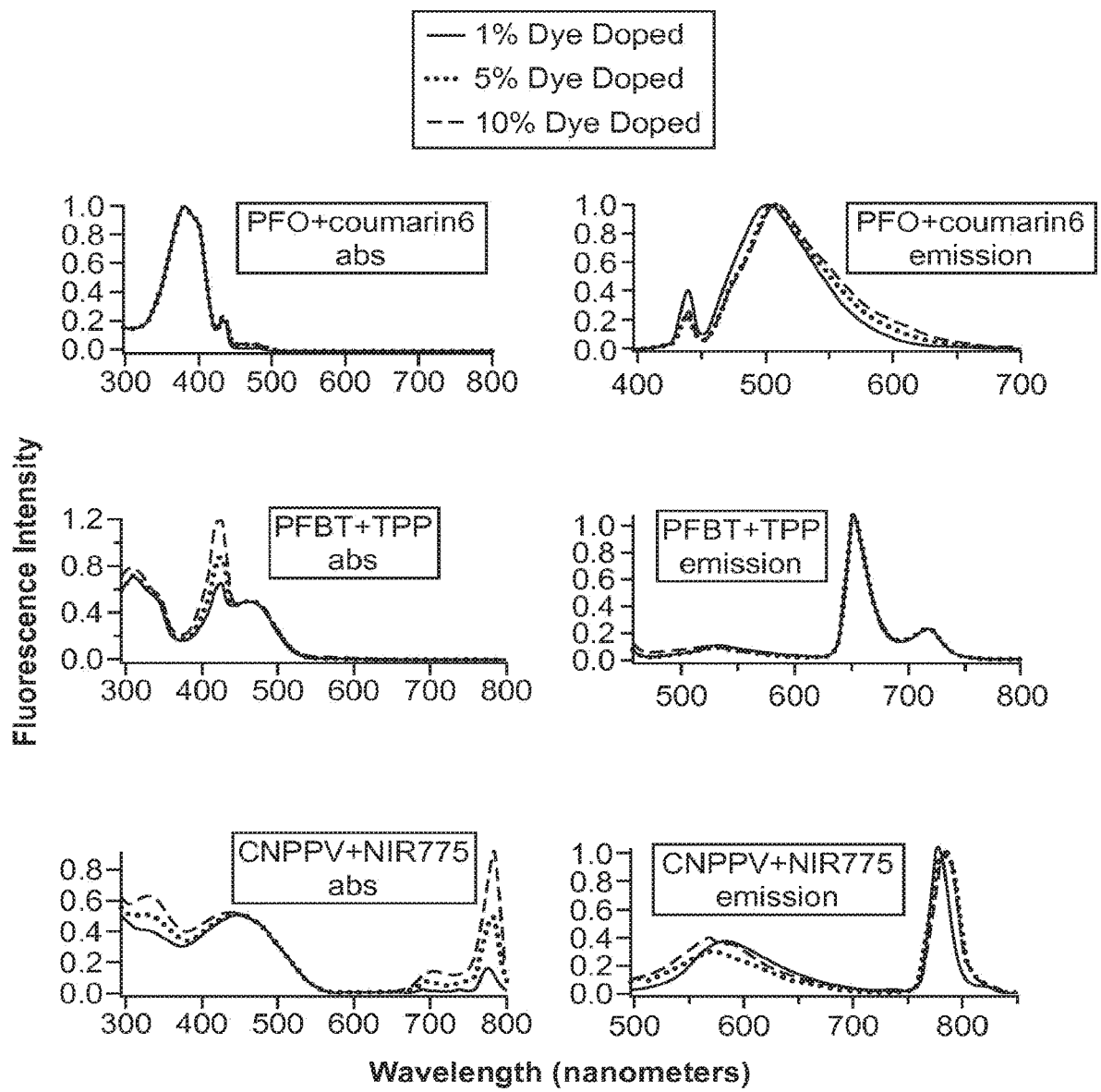
FIG. 15 shows spectral profiles of absorbed and emitted fluorescence for a variety of dye doped chromophoric particles. Solid line, dotted line, and dashed line represent 1%, 5% and 10% (by mass) dye doped polymer particles, respectively.

FIG. 15 shows spectral profiles of absorbance (graphs on left) and emission (graphs on right) for a variety of dye doped chromophoric particles, derived from optical spectroscopy measurements of the dye doped chromophoric particles. Solid line, dotted line and dashed line represent 1%, 5%, and 10% (by mass) dye doped encoded chromophoric polymer particles, respectively. The emission of semiconducting polymers is quenched in the doped dyes due to the presence of FRET taking place between the semiconducting polymers and dyes.

Example 6

Chromophoric Polymer Particles Comprising Dye Molecules and Lanthanide Complexes Used for Lifetime Encoding This example provides an exemplary combination of dye molecules, lanthanide materials such as europium complexes, and chromophoric polymer particles to produce a number of lifetime codes.

First, Eu(TTA)$_3$phen-NH$_2$ (6 mg) and PSMA (9 mg) were dissolved in anhydrous tetrahydrofuran (THF) (50 mL). The mixture was kept stirring for 48 h under reflux and N$_2$ flow protection. The resultant solution was evaporated to remove solvent. Furthermore, the product was dried for 40 min under vacuum. Finally, the powder product was dissolved in THF and the concentration of the obtained solution was adjusted to 1 mg/mL for subsequent encoded chromophoric polymer particle preparation. The encoded chromophoric polymer particles containing europium complexes were prepared by using the nanoprecipitation method. The concentration of the stock solution obtained by reaction of europium complexes with PSMA was adjusted to 1 mg/mL. The stock solution was diluted with THF to produce a 50 µg/mL solution. The diluted solution was sonicated to form a homogeneous solution. A 5 mL quantity of the solution was added quickly to 10 mL of MilliQ water in a bath sonicator. THF was removed by nitrogen stripping at room temperature, followed by filtration through a 0.2 micron filter.

The resulting functionalized Eu-PSMA encoded chromophoric polymer particle dispersions are clear and stable for months without signs of aggregation. The Eu-PSMA/PVK particles were prepared by mixing PVK into the Eu-PSMA THF solution with 1:1 ratio of PVK to europium complexes. The mixture was quickly injected into water to form Eu-PSMA/PVK particles. The lifetimes of the two types of particles can be changed by introducing a dye molecule such as Nile blue. The fluorescence decay curves of the two types of chromophoric particles with Nile blue dyes was obtained by excitation with a third harmonic (355 nanometers) of a Nd:YAG laser pulse, and monitoring the signal with a photomultiplier tube together with a digital oscilloscope.

Figure 16A:
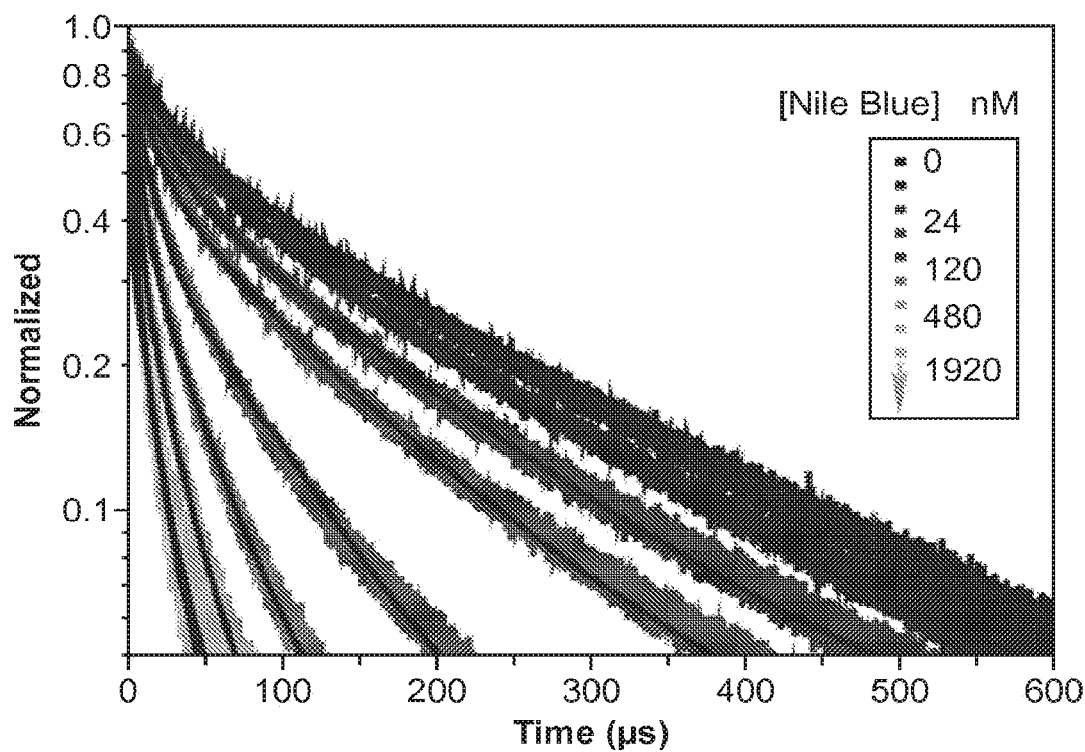
FIGS. 16A and 16B show time-decay curves of fluorescence for chromophoric particles comprising europium complexes and Nile blue dyes.
Figure 16B:
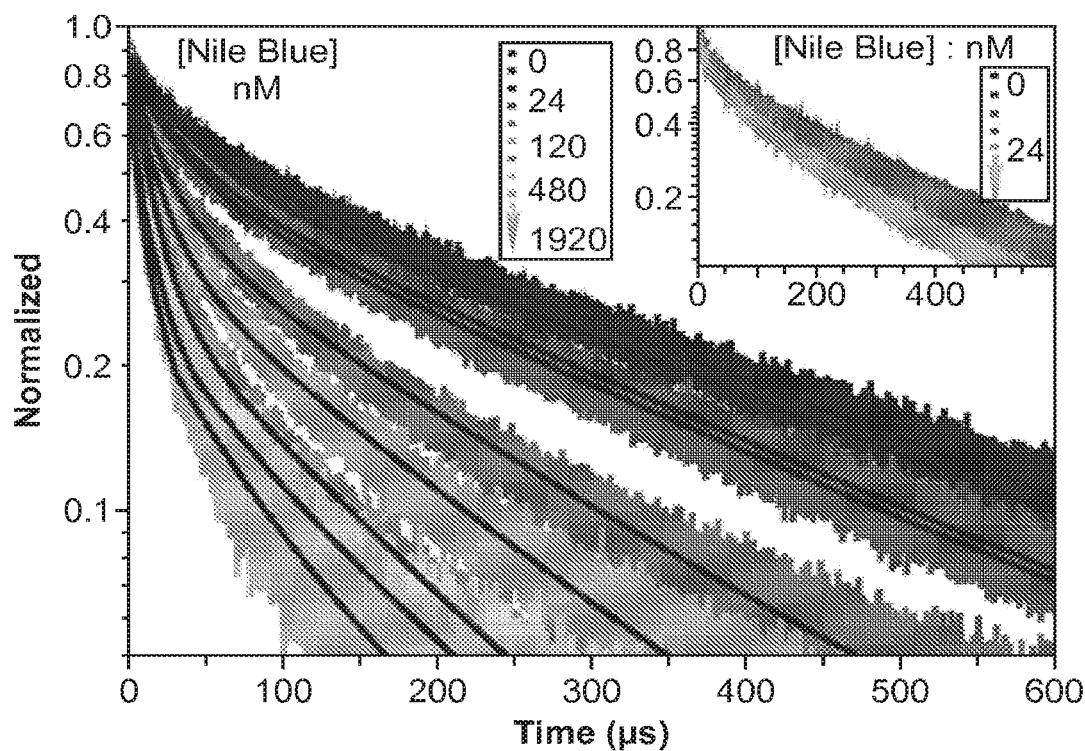

FIG. 16A shows time-decay curves of emitted fluorescence of chromophoric Eu-PSMA particles with increasing Nile blue concentration. FIG. 16B shows time-decay curves of emitted fluorescence of chromophoric Eu-PSMA/PVK particles with increasing Nile blue concentration. In both cases, the fluorescence lifetime of the europium complexes decreases with increasing dye concentration. The more rapidly decaying curves in FIGS. 16A and 16B correspond to particles comprising higher Nile blue concentrations. The broad range of fluorescence emission lifetimes obtained demonstrates that chromophoric polymer particles comprising dye molecules and lanthanide complexes can be used for fluorescence lifetime-based encoding strategies, either alone or in combination with other encoding strategies described herein.

Example 7

Chromophoric Polymer Particle-Based Color Codes Involving Energy Transfer to Tune the Emission Intensities Semi-Independently.

This example describes a strategy to employ energy transfer in chromophoric polymer particles to create color codes.

Five-color conjugated polymers with different emission wavelengths are used. B, G, O, R, and IR represent blue, green, orange, red, and infrared emissions, respectively. Energy transfer can occur in encoded chromophoric polymer particles comprising two different conjugated polymers. The emission intensity levels of these pure particles ranges from a minimum of 0 to a maximum of 100 (arbitrary units), and the emission intensity can be quenching by blending with a polymer having a red-shifted emission. Based on the five-color conjugated polymers, 25 color codes can be generated as in the examples below:

A color code generated by pure particles of one polymer: B100, G100, O100, R100, IR100.

A color code generated by particles of two polymers where the energy donor intensity is higher than the energy acceptor intensity, such as: B60G30, B60O30, B60R30, B60IR30, G60O30, G60R30, G60IR30, O60R30, O60IR30, R60IR30.

A color code generated by particles of two polymers where the energy donor intensity is lower than the energy acceptor intensity, such as: B30G60, B30O60, B30R60, B30IR60, G30O60, G30R60, G30IR60, O30R60, O30IR60, R30IR60

Other color codes can be generated using particles comprising donor-acceptor pairs with other intensity levels, including but not limited to B75G25, B50G50, B25G75 and the like.

Other color codes can be generated using particles comprising donor-acceptor pairs with intensity levels XMYN, where X and Y are selected independently from B, G, O, R, or IR, and M and N are selected independently from a range of values no less than 0 and no more than 100.

In addition, 100 color codes can be generated by adding to the nanoparticle a lanthanide complex having another emission color, the intensity of which can be independently tuned to four different intensity-levels.

While illustrative embodiments have been illustrated and described, it will be appreciated that various changes can be made therein without departing from the spirit and scope of the invention.

The embodiments of the invention in which an exclusive property or privilege is claimed are defined as follows:
1. A suspension comprising:
a first plurality of encoded chromophoric polymer particles wherein an encoded chromophoric polymer particle of the plurality of encoded chromophoric polymer particles comprises:
a polymer matrix; and
a plurality of distinct chromophores including a chromophoric polymer of the polymer matrix,
wherein each chromophore of the plurality of distinct chromophores comprises a set of tunable optical coding properties including an emission peak intensity, thereby defining a first optically detectable code for the encoded chromophoric polymer particle, and
wherein an emission spectrum of the encoded chromophoric polymer particle has multiple emission peaks under wavelength excitation;
a second plurality of encoded chromophoric polymer particles,
wherein:
the second plurality of encoded chromophoric polymer particles has a second optically detectable code; and
the first optically detectable code and the second optically detectable code are distinguishable from each other; and
a liquid.

2. The suspension of claim 1, wherein the first optically detectable code comprises an emission spectrum of the encoded chromophoric polymer particle, an emission lifetime of the encoded chromophoric polymer particle, or a combination thereof.

3. The suspension of claim 1, wherein each peak of the multiple emission peaks originates from one chromophore species.

4. The suspension of claim 1, wherein the plurality of distinct chromophores comprises more than one chromophore species, and two or more emission peaks of the emission spectrum originate from one chromophore species, and other emission peaks originate from another chromophore species.

5. The suspension of claim 1, wherein the set of tunable optical encoding properties of each chromophore of the plurality of distinct chromophores is further chosen from an emission peak intensity, an emission peak wavelength, an emission lifetime of the chromophore, and combinations thereof.

6. The suspension of claim 2, wherein each chromophore of the plurality of distinct chromophores has an emission spectrum, and wherein the set of tunable optical encoding properties of the chromophore comprises one or more characteristics of the emission spectrum.

7. The suspension of claim 1, wherein the set of tunable optical encoding properties of two or more distinct chromophores of the plurality of distinct chromophores are independently or semi-independently tunable or modulatable.

8. The suspension of claim 1, wherein the plurality of distinct chromophores comprises a fluorescent dye.

9. The suspension of claim 1, wherein the encoded chromophoric polymer particle shows a first set of emission peaks under a first excitation wavelength and a second set of emission peaks different from the first set of emission peaks under a second excitation wavelength different than the first excitation wavelength.

10. The suspension of claim 1, further comprising a biomolecule.

11. The suspension of claim 10, wherein the biomolecule is selected from the group consisting of a polypeptide, a polynucleotide, and combinations thereof.

12. The suspension of claim 1, wherein the first optically detectable code and the second optically detectable code each comprise a set of tunable optical encoding properties further chosen from an absorption peak wavelength, an emission peak wavelength, an emission peak intensity, and combinations thereof.

13. The suspension of claim 1, wherein an emission spectrum of the first plurality of plurality of encoded chromophoric polymer particles is distinguishable from an emission spectrum of the second plurality of plurality of encoded chromophoric polymer particles.

14. The suspension of claim 1, wherein the first plurality of plurality of encoded chromophoric polymer particles has emission spectra, emission lifetimes, emission intensities, and/or emission wavelengths that are distinct from emission spectra, emission lifetimes, emission intensities, and/or emission wavelengths of the second plurality of plurality of encoded chromophoric polymer particles.

15. The suspension of claim 1, wherein a concentration of the plurality of distinct chromophores and the chromophoric polymer in the first plurality of encoded chromophoric polymer particles is different than a concentration of a second plurality of distinct chromophores and a chromophoric polymer in the second plurality of encoded chromophoric polymer particles.

16. The suspension of claim 1, wherein the first plurality of encoded chromophoric polymer particles comprises a first biomolecule configured to selectively associate with a first analyte; and the second plurality of encoded chromophoric polymer particles comprises a second biomolecule configured to selectively associate with a second analyte different than the first analyte.

17. The suspension of claim 1, wherein the first plurality of encoded chromophoric polymer particles is configured to be excited at a first wavelength of light and the second plurality of encoded chromophoric polymer particles is configured to be excited at a second wavelength of light different than the first wavelength of light.

18. A kit for detecting analytes in a sample, comprising the suspension of claim 1.

19. A system for performing multiplex analysis, the system comprising:
the suspension of claim 1;
a source of electromagnetic radiation;
a detector; and
a computer comprising a processor and a memory device with executable instructions stored thereon, the instructions when executed causing the processor to:
operate the detector to measure an emission property;
store the measured emission property; and
analyze the measured emission property.

* * * * *